United States Patent
Chal et al.

(10) Patent No.: US 10,039,779 B2
(45) Date of Patent: Aug. 7, 2018

(54) COMBINATION FORMULATION OF TWO ANTIVIRAL COMPOUNDS

(71) Applicant: Gilead Pharmasset LLC, Foster City, CA (US)

(72) Inventors: Ben Chal, Millbrae, CA (US); Erik Mogalian, San Francisco, CA (US); Reza Oliyai, Burlingame, CA (US); Rowchanak Pakdaman, San Carlos, CA (US); Dimitrios Stefanidis, Mountain View, CA (US); Vahid Zia, San Carlos, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

(21) Appl. No.: 15/393,847

(22) Filed: Dec. 29, 2016

(65) Prior Publication Data

US 2017/0202865 A1  Jul. 20, 2017

Related U.S. Application Data

(63) Continuation of application No. 14/868,062, filed on Sep. 28, 2015, now abandoned, which is a continuation of application No. 14/168,264, filed on Jan. 30, 2014, now abandoned.

(60) Provisional application No. 61/907,332, filed on Nov. 21, 2013, provisional application No. 61/897,793, filed on Oct. 30, 2013, provisional application No. 61/870,729, filed on Aug. 27, 2013, provisional application No. 61/828,899, filed on May 30, 2013, provisional application No. 61/772,292, filed on Mar. 4, 2013, provisional application No. 61/759,320, filed on Jan. 31, 2013.

(51) Int. Cl.

| A61K 31/439 | (2006.01) |
|---|---|
| A61K 31/7072 | (2006.01) |
| A61K 31/4184 | (2006.01) |
| A61K 9/28 | (2006.01) |
| A61K 31/7056 | (2006.01) |
| A61K 31/4709 | (2006.01) |
| A61K 9/16 | (2006.01) |
| A61K 9/20 | (2006.01) |
| A61K 31/513 | (2006.01) |
| A61K 31/381 | (2006.01) |
| A61K 31/4025 | (2006.01) |
| A61K 31/497 | (2006.01) |
| A61K 31/4985 | (2006.01) |
| A61K 31/5025 | (2006.01) |
| A61K 31/5377 | (2006.01) |
| A61K 31/675 | (2006.01) |
| A61K 31/7076 | (2006.01) |
| A61K 31/4178 | (2006.01) |
| A61K 9/24 | (2006.01) |

(52) U.S. Cl.
CPC ........ *A61K 31/7072* (2013.01); *A61K 9/1623* (2013.01); *A61K 9/1635* (2013.01); *A61K 9/209* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/28* (2013.01); *A61K 31/381* (2013.01); *A61K 31/4025* (2013.01); *A61K 31/4178* (2013.01); *A61K 31/4184* (2013.01); *A61K 31/439* (2013.01); *A61K 31/4709* (2013.01); *A61K 31/497* (2013.01); *A61K 31/4985* (2013.01); *A61K 31/5025* (2013.01); *A61K 31/513* (2013.01); *A61K 31/5377* (2013.01); *A61K 31/675* (2013.01); *A61K 31/7056* (2013.01); *A61K 31/7076* (2013.01)

(58) Field of Classification Search
CPC .......................... A61K 31/439; A61K 31/7072
See application file for complete search history.

(56) References Cited

U.S. PATENT DOCUMENTS

| 3,798,209 A | 3/1974 | Robins et al. |
|---|---|---|
| RE29,835 E | 11/1978 | Witkowski et al. |
| 5,026,687 A | 6/1991 | Yarchoan et al. |
| 5,194,654 A | 3/1993 | Hostetler et al. |
| 5,210,015 A | 5/1993 | Gelfand et al. |
| 5,463,092 A | 10/1995 | Hostetler et al. |
| 5,538,848 A | 7/1996 | Livak et al. |
| 5,703,058 A | 12/1997 | Schinazi et al. |
| 5,858,389 A | 1/1999 | Elsherbini |
| 5,905,070 A | 5/1999 | Schinazi et al. |
| 6,232,300 B1 | 5/2001 | Schinazi et al. |
| 6,348,587 B1 | 2/2002 | Schinazi et al. |
| 6,391,859 B1 | 5/2002 | Schinazi et al. |
| 6,475,985 B1 | 11/2002 | Wagner et al. |
| 6,479,463 B1 | 11/2002 | Wang et al. |
| 6,495,677 B1 | 12/2002 | Ramasamy et al. |

(Continued)

FOREIGN PATENT DOCUMENTS

| CN | 101108870 | 1/2008 |
|---|---|---|
| DE | 102008057284 | 5/2010 |

(Continued)

OTHER PUBLICATIONS

U.S. Appl. No. 14/453,489, filed Aug. 6, 2014, Mogalian et al.

(Continued)

*Primary Examiner* — John Pak
*Assistant Examiner* — Nathan W Schlientz
(74) *Attorney, Agent, or Firm* — Sheppard Mullin Richter & Hampton LLP

(57) ABSTRACT

Disclosed are pharmaceutical compositions having an effective amount of substantially amorphous ledipasvir and an effective amount of substantially crystalline sofosbuvir.

16 Claims, 11 Drawing Sheets

(56) References Cited

U.S. PATENT DOCUMENTS

| | | |
|---|---|---|
| 6,509,320 B1 | 1/2003 | Wang et al. |
| 6,552,183 B1 | 4/2003 | Ramasamy et al. |
| 6,573,248 B2 | 6/2003 | Ramasamy et al. |
| 6,589,941 B1 | 7/2003 | Fahrig et al. |
| 6,642,206 B2 | 11/2003 | Ramasamy et al. |
| 6,660,721 B2 | 12/2003 | Devos et al. |
| 6,677,314 B2 | 1/2004 | Klecker et al. |
| 6,677,315 B2 | 1/2004 | Klecker et al. |
| 6,680,303 B2 | 1/2004 | Schinazi et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,763,607 B2 | 7/2004 | Beyerinck et al. |
| 6,777,395 B2 | 8/2004 | Bhat et al. |
| 6,784,166 B2 | 8/2004 | Devos et al. |
| 6,787,526 B1 | 9/2004 | Bryant et al. |
| 6,812,219 B2 | 11/2004 | Lacolla et al. |
| 6,815,542 B2 | 11/2004 | Hong et al. |
| 6,846,810 B2 | 1/2005 | Martin et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,148,206 B2 | 12/2006 | Sommadossi et al. |
| 7,163,929 B2 | 1/2007 | Sommadossi et al. |
| 7,202,224 B2 | 4/2007 | Eldrup et al. |
| 7,259,186 B2 | 8/2007 | Cink et al. |
| 7,268,119 B2 | 9/2007 | Cook et al. |
| 7,273,624 B2 | 9/2007 | Rosenberg et al. |
| 7,307,065 B2 | 12/2007 | Schinazi et al. |
| 7,323,453 B2 | 1/2008 | Olsen et al. |
| 7,365,057 B2 | 4/2008 | Lacolla et al. |
| 7,390,791 B2 | 6/2008 | Becker et al. |
| 7,429,572 B2 | 9/2008 | Clark |
| 7,601,820 B2 | 10/2009 | Wang et al. |
| 7,608,597 B2 | 10/2009 | Sommadossi et al. |
| 7,608,600 B2 | 10/2009 | Storer et al. |
| 7,635,689 B2 | 12/2009 | Lacolla et al. |
| 7,704,992 B2 | 4/2010 | Bachand et al. |
| 7,754,699 B2 | 7/2010 | Chun et al. |
| 7,780,988 B2 | 8/2010 | Beyerinck et al. |
| 7,820,380 B2 | 10/2010 | Huang |
| 7,879,815 B2 | 2/2011 | MacCoss et al. |
| 7,964,580 B2 | 6/2011 | Sofia et al. |
| 8,088,368 B2 | 1/2012 | Guo et al. |
| 8,148,349 B2 | 4/2012 | Meppen et al. |
| 8,173,621 B2 | 5/2012 | Du et al. |
| 8,178,491 B2 | 5/2012 | Cho et al. |
| 8,273,341 B2 | 9/2012 | Guo et al. |
| 8,334,270 B2 | 12/2012 | Sofia et al. |
| 8,362,068 B2 | 1/2013 | Dousson et al. |
| 8,415,322 B2 | 4/2013 | Clark |
| 8,466,159 B2 | 6/2013 | Bernstein et al. |
| 8,481,713 B2 | 7/2013 | Wang et al. |
| 8,492,386 B2 | 7/2013 | Bernstein et al. |
| 8,492,539 B2 | 7/2013 | Chun et al. |
| 8,513,298 B2 | 8/2013 | Canales et al. |
| 8,546,402 B2 | 10/2013 | Sokoloff et al. |
| 8,551,973 B2 | 10/2013 | Bao et al. |
| 8,563,530 B2 | 10/2013 | Chang et al. |
| 8,569,478 B2 | 10/2013 | Du et al. |
| 8,575,118 B2 | 11/2013 | Guo et al. |
| 8,580,765 B2 | 11/2013 | Sofia et al. |
| 8,618,076 B2 | 12/2013 | Ross et al. |
| 8,629,263 B2 | 1/2014 | Ross et al. |
| 8,633,309 B2 | 1/2014 | Ross et al. |
| 8,642,756 B2 | 2/2014 | Ross et al. |
| 8,680,106 B2 | 3/2014 | Bernstein et al. |
| 8,685,984 B2 | 4/2014 | Bernstein et al. |
| 8,691,938 B2 | 4/2014 | Degoey et al. |
| 8,669,234 B2 | 5/2014 | Guo et al. |
| 8,716,262 B2 | 5/2014 | Sofia et al. |
| 8,716,263 B2 | 5/2014 | Chun et al. |
| 8,735,372 B2 | 5/2014 | Du et al. |
| 8,735,569 B2 | 5/2014 | Ross et al. |
| 8,759,510 B2 | 6/2014 | Du et al. |
| 8,809,265 B2 | 8/2014 | Bernstein et al. |
| 8,815,858 B2 | 8/2014 | Bjornson et al. |
| 8,822,430 B2 | 9/2014 | Bacon et al. |
| 8,841,275 B2 | 9/2014 | Du et al. |
| 8,841,278 B2 | 9/2014 | Bacon et al. |
| 8,841,340 B2 | 9/2014 | Hashash et al. |
| 8,859,756 B2 | 10/2014 | Ross et al. |
| 8,889,159 B2 | 11/2014 | Cleary et al. |
| 8,906,880 B2 | 12/2014 | Du et al. |
| 8,937,150 B2 | 1/2015 | Degoey et al. |
| 8,957,045 B2 | 2/2015 | Sofia et al. |
| 8,957,046 B2 | 2/2015 | Du et al. |
| 8,969,357 B2 | 3/2015 | Bernstein et al. |
| 8,969,588 B2 | 3/2015 | Scott et al. |
| 8,993,578 B2 | 3/2015 | Bernstein et al. |
| 9,034,832 B2 | 5/2015 | Gao et al. |
| 9,045,520 B2 | 6/2015 | Chun et al. |
| 9,056,860 B2 | 6/2015 | Scott et al. |
| 9,084,730 B2 | 7/2015 | Bedos et al. |
| 9,085,573 B2 | 7/2015 | Du et al. |
| 9,511,056 B2 | 12/2016 | Bacon et al. |
| 2001/0034440 A1 | 10/2001 | Shepard et al. |
| 2001/0038833 A1 | 11/2001 | Rybak et al. |
| 2002/0008241 A1 | 1/2002 | Edmond et al. |
| 2002/0058635 A1 | 5/2002 | Averett |
| 2002/0147160 A1 | 10/2002 | Bhat et al. |
| 2002/0198173 A1 | 12/2002 | Schinazi et al. |
| 2003/0050229 A1 | 3/2003 | Sommadossi et al. |
| 2003/0060400 A1 | 3/2003 | Lacolla et al. |
| 2003/0119752 A1 | 6/2003 | Farmer et al. |
| 2003/0109697 A1 | 7/2003 | Shepard et al. |
| 2003/0144502 A1 | 7/2003 | Pietrzkowski et al. |
| 2003/0153744 A1 | 8/2003 | Mekouar et al. |
| 2003/0176433 A1 | 9/2003 | Beaulieu et al. |
| 2003/0187018 A1 | 10/2003 | Llinas-Brunet et al. |
| 2003/0207922 A1 | 11/2003 | Neuner et al. |
| 2004/0006007 A1 | 1/2004 | Gosselin et al. |
| 2004/0014108 A1 | 1/2004 | Eldrup et al. |
| 2004/0023901 A1 | 2/2004 | Cook et al. |
| 2004/0024190 A1 | 2/2004 | Beaulieu et al. |
| 2004/0059104 A1 | 3/2004 | Cook et al. |
| 2004/0063622 A1 | 4/2004 | Sommadossi et al. |
| 2004/0067901 A1 | 4/2004 | Bhat et al. |
| 2004/0072788 A1 | 4/2004 | Bhat et al. |
| 2004/0087541 A1 | 5/2004 | Jonaitis et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0142989 A1 | 7/2004 | Finzel et al. |
| 2004/0142993 A1 | 7/2004 | Battistini et al. |
| 2004/0167140 A1 | 8/2004 | Schinazi et al. |
| 2004/0171570 A1 | 9/2004 | Allerson et al. |
| 2004/0214844 A1 | 10/2004 | Otto et al. |
| 2004/0229839 A1 | 11/2004 | Babu et al. |
| 2004/0229840 A1 | 11/2004 | Bhat et al. |
| 2004/0254141 A1 | 12/2004 | Schinazi et al. |
| 2004/0259934 A1 | 12/2004 | Olsen et al. |
| 2004/0265969 A1 | 12/2004 | Li et al. |
| 2005/0009737 A1 | 1/2005 | Clark |
| 2005/0026160 A1 | 2/2005 | Allerson et al. |
| 2005/0026853 A1 | 2/2005 | Mekouar et al. |
| 2005/0031588 A1 | 2/2005 | Sommadassi et al. |
| 2005/0043390 A1 | 2/2005 | Bravi et al. |
| 2005/0069522 A1 | 3/2005 | Colonno et al. |
| 2005/0075309 A1 | 4/2005 | Storer et al. |
| 2005/0080034 A1 | 4/2005 | Standring et al. |
| 2005/0082144 A1 | 4/2005 | Maupin et al. |
| 2005/0090432 A1 | 4/2005 | McPhee et al. |
| 2005/0096364 A1 | 5/2005 | Romine et al. |
| 2005/0098125 A1 | 5/2005 | Hathaway et al. |
| 2005/0124532 A1 | 6/2005 | Sommadossi et al. |
| 2005/0130923 A1 | 6/2005 | Bhat et al. |
| 2005/0130931 A1 | 6/2005 | Boyer et al. |

(56) References Cited

U.S. PATENT DOCUMENTS

| | | |
|---|---|---|
| 2005/0137161 A1 | 6/2005 | Sommadossi et al. |
| 2005/0148534 A1 | 7/2005 | Castellino et al. |
| 2005/0154056 A1 | 7/2005 | Yang et al. |
| 2005/0164960 A1 | 7/2005 | Olsen et al. |
| 2005/0215513 A1 | 9/2005 | Boojamra et al. |
| 2005/0215614 A1 | 9/2005 | Singh et al. |
| 2005/0227947 A1 | 10/2005 | Chen et al. |
| 2005/0228013 A1 | 10/2005 | Thurkauf et al. |
| 2005/0261237 A1 | 11/2005 | Boojamra et al. |
| 2006/0003951 A1 | 1/2006 | Mekouar et al. |
| 2006/0004063 A1 | 1/2006 | Finzel et al. |
| 2006/0035866 A1 | 2/2006 | Cannizzaro et al. |
| 2006/0040890 A1 | 2/2006 | Martin et al. |
| 2006/0040927 A1 | 2/2006 | Blake et al. |
| 2006/0040944 A1 | 2/2006 | Gosselin et al. |
| 2006/0046983 A1 | 3/2006 | Hudyma et al. |
| 2006/0079478 A1 | 4/2006 | Boojamra et al. |
| 2006/0094706 A1 | 5/2006 | Paruch et al. |
| 2006/0110724 A1 | 5/2006 | Burkhardt et al. |
| 2006/0122154 A1 | 6/2006 | Olsen et al. |
| 2006/0166964 A1 | 7/2006 | Hudyma |
| 2006/0194749 A1 | 8/2006 | Keicher et al. |
| 2006/0234962 A1 | 10/2006 | Olsen et al. |
| 2006/0241064 A1 | 10/2006 | Roberts et al. |
| 2006/0276405 A1 | 12/2006 | Albrecht |
| 2006/0276511 A1 | 12/2006 | Serrano-Wu et al. |
| 2006/0287300 A1 | 12/2006 | Klein et al. |
| 2006/0293306 A1 | 12/2006 | Beaulieu et al. |
| 2007/0004669 A1 | 1/2007 | Carroll et al. |
| 2007/0015905 A1 | 1/2007 | Lacolla et al. |
| 2007/0024277 A1 | 2/2007 | Cech et al. |
| 2007/0037735 A1 | 2/2007 | Gosselin et al. |
| 2007/0037773 A1 | 2/2007 | Sommadossi et al. |
| 2007/0042939 A1 | 2/2007 | Lacolla et al. |
| 2007/0042988 A1 | 2/2007 | Klumpp et al. |
| 2007/0042990 A1 | 2/2007 | Gosselin et al. |
| 2007/0049754 A1 | 3/2007 | Boojamra et al. |
| 2007/0054842 A1 | 3/2007 | Blatt et al. |
| 2007/0060498 A1 | 3/2007 | Gosselin et al. |
| 2007/0060541 A1 | 3/2007 | Gosselin et al. |
| 2007/0087960 A1 | 4/2007 | Storer et al. |
| 2007/0123484 A1 | 5/2007 | Bhat et al. |
| 2007/0135363 A1 | 6/2007 | Cook et al. |
| 2007/0142380 A1 | 6/2007 | Beaulieu et al. |
| 2007/0155716 A1 | 7/2007 | Simmen et al. |
| 2007/0197463 A1 | 8/2007 | Chun et al. |
| 2007/0197478 A1 | 8/2007 | Jones et al. |
| 2007/0218138 A1 | 9/2007 | Bittorf et al. |
| 2007/0225249 A1 | 9/2007 | Shi |
| 2007/0231318 A1 | 10/2007 | Saha et al. |
| 2007/0232627 A1 | 10/2007 | Betebenner et al. |
| 2007/0232645 A1 | 10/2007 | Rockway et al. |
| 2007/0265222 A1 | 11/2007 | MacCoss et al. |
| 2007/0265262 A1 | 11/2007 | Schmitz et al. |
| 2007/0275912 A1 | 11/2007 | Bhat et al. |
| 2007/0275930 A1 | 11/2007 | Gentles et al. |
| 2007/0275947 A1 | 11/2007 | Bergstrom |
| 2008/0008682 A1 | 1/2008 | Chong et al. |
| 2008/0021047 A1 | 1/2008 | Butora et al. |
| 2008/0050336 A1 | 2/2008 | Bachand et al. |
| 2008/0057031 A1 | 3/2008 | Casarez et al. |
| 2008/0070861 A1 | 3/2008 | Clark et al. |
| 2008/0108617 A1 | 5/2008 | Desai et al. |
| 2008/0146788 A1 | 6/2008 | Bhat et al. |
| 2008/0182863 A1 | 7/2008 | Simmen et al. |
| 2008/0253995 A1 | 10/2008 | Clark et al. |
| 2008/0280842 A1 | 11/2008 | MacCoss et al. |
| 2009/0004135 A1 | 1/2009 | Clark |
| 2009/0036666 A1 | 2/2009 | Clark |
| 2009/0041716 A1 | 2/2009 | Kim et al. |
| 2009/0068140 A1 | 3/2009 | Bachand et al. |
| 2009/0105302 A1 | 4/2009 | Simmen et al. |
| 2009/0062311 A1 | 5/2009 | Simmen et al. |
| 2009/0137521 A1 | 5/2009 | Hamilton et al. |
| 2009/0156595 A1 | 6/2009 | Raboisson et al. |
| 2009/0202478 A1 | 8/2009 | Bachand et al. |
| 2009/0202483 A1 | 8/2009 | Bachand et al. |
| 2009/0233879 A1 | 9/2009 | Reddy et al. |
| 2009/0269305 A1 | 10/2009 | Seiwert et al. |
| 2009/0280084 A1 | 11/2009 | Schinazi et al. |
| 2009/0281140 A1 | 11/2009 | Simmen et al. |
| 2009/0281141 A1 | 11/2009 | Simmen et al. |
| 2009/0291902 A1 | 11/2009 | Cottrell et al. |
| 2009/0311414 A1 | 12/2009 | Kessler et al. |
| 2010/0015090 A1 | 1/2010 | Tung et al. |
| 2010/0022468 A1 | 1/2010 | Meppen et al. |
| 2010/0035835 A1 | 2/2010 | Narjes et al. |
| 2010/0048917 A1 | 2/2010 | Wang et al. |
| 2010/0080772 A1 | 4/2010 | Belema et al. |
| 2010/0137576 A1 | 6/2010 | Stec et al. |
| 2010/0152128 A1 | 6/2010 | Attenni et al. |
| 2010/0160335 A1 | 6/2010 | Kohno et al. |
| 2010/0173863 A1 | 7/2010 | Schinazi et al. |
| 2010/0226885 A1 | 9/2010 | Albrecht et al. |
| 2010/0227801 A1 | 9/2010 | Hopkins |
| 2010/0234316 A1 | 9/2010 | MacCoss et al. |
| 2010/0249068 A1 | 9/2010 | Beigelman et al. |
| 2010/0249190 A1 | 9/2010 | Lopez et al. |
| 2010/0267785 A1 | 10/2010 | Wu et al. |
| 2010/0298257 A1 | 11/2010 | Ross et al. |
| 2010/0310512 A1 | 12/2010 | Guo et al. |
| 2010/0316594 A1 | 12/2010 | Sommadossi et al. |
| 2010/0316607 A1 | 12/2010 | Or et al. |
| 2011/0020272 A1 | 1/2011 | Schubert et al. |
| 2011/0077280 A1 | 3/2011 | Bender et al. |
| 2011/0092415 A1 | 4/2011 | Degoey et al. |
| 2011/0137633 A1 | 6/2011 | Hutchins et al. |
| 2011/0142798 A1 | 6/2011 | Qiu et al. |
| 2011/0150827 A1 | 6/2011 | Dousson et al. |
| 2011/0178129 A1 | 7/2011 | Canales et al. |
| 2011/0207660 A1 | 8/2011 | Sheth et al. |
| 2011/0237621 A1 | 9/2011 | Simmen et al. |
| 2011/0306541 A1 | 12/2011 | Delaney, IV et al. |
| 2012/0094284 A1 | 4/2012 | Lopatin et al. |
| 2012/0107278 A1 | 5/2012 | Berrey et al. |
| 2012/0245335 A1 | 9/2012 | Clark |
| 2012/0246335 A1 | 9/2012 | Liu et al. |
| 2012/0251152 A1 | 10/2012 | Brewington et al. |
| 2012/0264711 A1 | 10/2012 | Guo et al. |
| 2013/0102526 A1 | 4/2013 | Bernstein et al. |
| 2013/0102557 A1 | 4/2013 | Bernstein et al. |
| 2013/0102558 A1 | 4/2013 | Bernstein et al. |
| 2013/0109647 A1 | 5/2013 | Berrey et al. |
| 2013/0136776 A1 | 5/2013 | Cleary et al. |
| 2013/0156732 A1 | 6/2013 | Bacon et al. |
| 2013/0164260 A1 | 6/2013 | Bacon et al. |
| 2013/0165401 A1 | 6/2013 | Ross et al. |
| 2013/0172239 A1 | 7/2013 | Gao et al. |
| 2013/0243726 A1 | 9/2013 | Ray et al. |
| 2013/0273005 A1 | 10/2013 | Delaney et al. |
| 2013/0288997 A1 | 10/2013 | Ross et al. |
| 2013/0315866 A1 | 11/2013 | Parsy et al. |
| 2013/0324496 A1 | 12/2013 | Scott et al. |
| 2013/0324740 A1 | 12/2013 | Scott et al. |
| 2013/0338349 A1 | 12/2013 | Chun et al. |
| 2014/0039021 A1 | 2/2014 | Bacon et al. |
| 2014/0045783 A1 | 2/2014 | Du et al. |
| 2014/0051656 A1 | 2/2014 | Guo et al. |
| 2014/0107016 A1 | 4/2014 | Bernstein et al. |
| 2014/0107017 A1 | 4/2014 | Bernstein et al. |
| 2014/0121366 A1 | 5/2014 | Chun et al. |
| 2014/0187511 A1 | 7/2014 | Du et al. |
| 2014/0212487 A1 | 7/2014 | Mogalian et al. |
| 2014/0212491 A1 | 7/2014 | Chal et al. |
| 2014/0249074 A1 | 9/2014 | Bacon et al. |
| 2014/0249101 A1 | 9/2014 | Ding et al. |
| 2014/0309187 A1 | 10/2014 | Hashash et al. |
| 2014/0323395 A1 | 10/2014 | Bernstein et al. |
| 2014/0343008 A1 | 11/2014 | Yang et al. |
| 2015/0018300 A1 | 1/2015 | Du et al. |
| 2015/0087045 A1 | 3/2015 | Edwards et al. |
| 2015/0141353 A1 | 5/2015 | Delaney et al. |
| 2015/0141659 A1 | 5/2015 | Mogalian et al. |
| 2015/0150896 A1 | 6/2015 | Cleary et al. |

(56) References Cited

U.S. PATENT DOCUMENTS

| | | | |
|---|---|---|---|
| 2015/0164976 A1 | 6/2015 | Awni et al. | |
| 2015/0196615 A1 | 7/2015 | Awni et al. | |
| 2015/0231166 A1 | 8/2015 | Du et al. | |
| 2015/0232453 A1 | 8/2015 | Scott et al. | |

FOREIGN PATENT DOCUMENTS

| | | |
|---|---|---|
| EP | 0901786 | 6/2007 |
| EP | 1027886 | 7/2008 |
| EP | 2583677 | 4/2013 |
| EP | 2583680 | 4/2013 |
| EP | 2797586 | 11/2014 |
| JP | 5238939 | 9/1993 |
| WO | WO 1990/000555 | 1/1990 |
| WO | WO 1993/000910 | 1/1993 |
| WO | WO 1996/029336 | 9/1996 |
| WO | WO 1996/032403 | 10/1996 |
| WO | WO 1998/016184 | 4/1998 |
| WO | WO 1999/015194 | 4/1999 |
| WO | WO 1999/037753 | 7/1999 |
| WO | WO 1999/043691 | 9/1999 |
| WO | WO 1999/059621 | 11/1999 |
| WO | WO 1999/064016 | 12/1999 |
| WO | WO 2000/009531 | 4/2000 |
| WO | WO 2000/018775 | 4/2000 |
| WO | WO 2000/037110 | 6/2000 |
| WO | WO 2001/007454 | 2/2001 |
| WO | WO 2001/032153 | 8/2001 |
| WO | WO 2001/079246 | 10/2001 |
| WO | WO 2001/081359 | 11/2001 |
| WO | WO 2001/090121 | 11/2001 |
| WO | WO 2001/091737 | 12/2001 |
| WO | WO 2001/092282 | 12/2001 |
| WO | WO 2001/096353 | 12/2001 |
| WO | WO 2002/008241 | 1/2002 |
| WO | WO 2002/008256 | 1/2002 |
| WO | WO 2002/018404 | 3/2002 |
| WO | WO 2002/032414 | 4/2002 |
| WO | WO 2002/032920 | 4/2002 |
| WO | WO 2002/057425 | 4/2002 |
| WO | WO 2002/048165 | 6/2002 |
| WO | WO 2002/057287 | 7/2002 |
| WO | WO 2002/100415 | 12/2002 |
| WO | WO 2003/000713 | 1/2003 |
| WO | WO 2003/006490 | 1/2003 |
| WO | WO 2003/010141 | 2/2003 |
| WO | WO 2003/024461 | 3/2003 |
| WO | WO 2003/026589 | 4/2003 |
| WO | WO 2003/051899 | 6/2003 |
| WO | WO 2003/061576 | 7/2003 |
| WO | WO 2003/062256 | 7/2003 |
| WO | WO 2003/068244 | 8/2003 |
| WO | WO 2003/105770 | 12/2003 |
| WO | WO 2003/106477 | 12/2003 |
| WO | WO 2004/000858 | 12/2003 |
| WO | WO 2004/002422 | 1/2004 |
| WO | WO 2004/002999 | 1/2004 |
| WO | WO 2004/003000 | 1/2004 |
| WO | WO 2004/003138 | 1/2004 |
| WO | WO 2004/007512 | 1/2004 |
| WO | WO 2004/009020 | 1/2004 |
| WO | WO 2004/009610 | 1/2004 |
| WO | WO 2004/014313 | 2/2004 |
| WO | WO 2004/046331 | 6/2004 |
| WO | WO 2004/080466 | 9/2004 |
| WO | WO 2004/096235 | 11/2004 |
| WO | WO 2004/096286 | 11/2004 |
| WO | WO 2005/002626 | 1/2005 |
| WO | WO 2005/003147 | 1/2005 |
| WO | WO 2005/009418 | 2/2005 |
| WO | WO 2005/012327 | 2/2005 |
| WO | WO 2005/020884 | 3/2005 |
| WO | WO 2005/021568 | 3/2005 |
| WO | WO 2005/082144 | 9/2005 |
| WO | WO 2005/121634 | 12/2005 |
| WO | WO 2005/123076 | 12/2005 |
| WO | WO 2005/123087 | 12/2005 |
| WO | WO 2006/000922 | 1/2006 |
| WO | WO 2006/012078 | 2/2006 |
| WO | WO 2006/012440 | 2/2006 |
| WO | WO 2006/029081 | 3/2006 |
| WO | WO 2006/031725 | 3/2006 |
| WO | WO 2006/037028 | 4/2006 |
| WO | WO 2006/050161 | 5/2006 |
| WO | WO 2006/065335 | 6/2006 |
| WO | WO 2006/067606 | 6/2006 |
| WO | WO 2006/116557 | 11/2006 |
| WO | WO 2006/121820 | 11/2006 |
| WO | WO 2006/133326 | 12/2006 |
| WO | WO 2007/002602 | 1/2007 |
| WO | WO 2007/020193 | 2/2007 |
| WO | WO 2007/065829 | 6/2007 |
| WO | WO 2007/095269 | 8/2007 |
| WO | WO 2007/109604 | 9/2007 |
| WO | WO 2008/005519 | 1/2008 |
| WO | WO 2008/005565 | 1/2008 |
| WO | WO 2008/010921 | 1/2008 |
| WO | WO 2008/021927 | 2/2008 |
| WO | WO 2008/021928 | 2/2008 |
| WO | WO 2008/021936 | 2/2008 |
| WO | WO 2008/045419 | 4/2008 |
| WO | WO 2008/079206 | 7/2008 |
| WO | WO 2008/082601 | 7/2008 |
| WO | WO 2008/085508 | 7/2008 |
| WO | WO 2008/121634 | 10/2008 |
| WO | WO 2008/142055 | 11/2008 |
| WO | WO 2008/144380 | 11/2008 |
| WO | WO 2009/005676 | 1/2009 |
| WO | WO 2009/005677 | 1/2009 |
| WO | WO 2009/005687 | 1/2009 |
| WO | WO 2009/009001 | 1/2009 |
| WO | WO 2009/020825 | 2/2009 |
| WO | WO 2009/020828 | 2/2009 |
| WO | WO 2009/038663 | 3/2009 |
| WO | WO 2009/050289 | 4/2009 |
| WO | WO 2009/052287 | 4/2009 |
| WO | WO 2009/089523 | 7/2009 |
| WO | WO 2009/102318 | 8/2009 |
| WO | WO 2009/102325 | 8/2009 |
| WO | WO 2009/102568 | 8/2009 |
| WO | WO 2009/102633 | 8/2009 |
| WO | WO 2009/115893 | 9/2009 |
| WO | WO 2009/120878 | 10/2009 |
| WO | WO 2009/129120 | 10/2009 |
| WO | WO 2009/132123 | 10/2009 |
| WO | WO 2009/152095 | 12/2009 |
| WO | WO 2010/004343 | 1/2010 |
| WO | WO 2010/017401 | 2/2010 |
| WO | WO 2010/017432 | 2/2010 |
| WO | WO 2010/062821 | 6/2010 |
| WO | WO 2010/065668 | 6/2010 |
| WO | WO 2010/065674 | 6/2010 |
| WO | WO 2010/065681 | 6/2010 |
| WO | WO 2010/075517 | 7/2010 |
| WO | WO 2010/075549 | 7/2010 |
| WO | WO 2010/075554 | 7/2010 |
| WO | WO 2010/077613 | 7/2010 |
| WO | WO 2010/080878 | 7/2010 |
| WO | WO 2010/081082 | 7/2010 |
| WO | WO 2010/091413 | 8/2010 |
| WO | WO 2010/094977 | 8/2010 |
| WO | WO 2010/096302 | 8/2010 |
| WO | WO 2010/096462 | 8/2010 |
| WO | WO 2010/096777 | 8/2010 |
| WO | WO 2010/097229 | 9/2010 |
| WO | WO 2010/099527 | 9/2010 |
| WO | WO 2010/111483 | 9/2010 |
| WO | WO 2010/111534 | 9/2010 |
| WO | WO 2010/111673 | 9/2010 |
| WO | WO 2010/112203 | 10/2010 |
| WO | WO 2010/117635 | 10/2010 |
| WO | WO 2010/117977 | 10/2010 |
| WO | WO 2010/120621 | 10/2010 |
| WO | WO 2010/120935 | 10/2010 |

(56) References Cited

FOREIGN PATENT DOCUMENTS

| | | |
|---|---|---|
| WO | WO 2010/122162 | 10/2010 |
| WO | WO 2010/132538 | 11/2010 |
| WO | WO 2010/132601 | 11/2010 |
| WO | WO 2010/135569 | 11/2010 |
| WO | WO 2010/138368 | 12/2010 |
| WO | WO 2010/138488 | 12/2010 |
| WO | WO 2010/138790 | 12/2010 |
| WO | WO 2010/138791 | 12/2010 |
| WO | WO 2010/144646 | 12/2010 |
| WO | WO 2010/148006 | 12/2010 |
| WO | WO 2011/004276 | 1/2011 |
| WO | WO 2011/007454 | 1/2011 |
| WO | WO 2011/009084 | 1/2011 |
| WO | WO 2001/060315 | 2/2011 |
| WO | WO 2011/015657 | 2/2011 |
| WO | WO 2011/015658 | 2/2011 |
| WO | WO 2011/026920 | 3/2011 |
| WO | WO 2011/028596 | 3/2011 |
| WO | WO 2011/031904 | 3/2011 |
| WO | WO 2011/031934 | 3/2011 |
| WO | WO 2011/035231 | 3/2011 |
| WO | WO 2011/046811 | 4/2011 |
| WO | WO 2011/050146 | 4/2011 |
| WO | WO 2011/054834 | 5/2011 |
| WO | WO 2011/059850 | 5/2011 |
| WO | WO 2011/059887 | 5/2011 |
| WO | WO 2011/060000 | 5/2011 |
| WO | WO 2011/066241 | 6/2011 |
| WO | WO 2011/075439 | 6/2011 |
| WO | WO 2011/075607 | 6/2011 |
| WO | WO 2011/075615 | 6/2011 |
| WO | WO 2011/079327 | 6/2011 |
| WO | WO 2011/082077 | 7/2011 |
| WO | WO 2011/087740 | 7/2011 |
| WO | WO 2011/088345 | 7/2011 |
| WO | WO 2011/091446 | 7/2011 |
| WO | WO 2011/112429 | 9/2011 |
| WO | WO 2011/123645 | 10/2011 |
| WO | WO 2011/123672 | 10/2011 |
| WO | WO 2011/146401 | 11/2011 |
| WO | WO 2011/150288 | 12/2011 |
| WO | WO 2011/156578 | 12/2011 |
| WO | WO 2011/156757 | 12/2011 |
| WO | WO 2012/012465 | 1/2012 |
| WO | WO 2012/027712 | 3/2012 |
| WO | WO 2012/039791 | 3/2012 |
| WO | WO 2012/041014 | 4/2012 |
| WO | WO 2012/048421 | 4/2012 |
| WO | WO 2012/068234 | 5/2012 |
| WO | WO 2012/087596 | 6/2012 |
| WO | WO 2012/087976 | 6/2012 |
| WO | WO 2012/130862 | 10/2012 |
| WO | WO 2013/000855 | 1/2013 |
| WO | WO 2013/030135 | 3/2013 |
| WO | WO 2013/040492 | 3/2013 |
| WO | WO 2013/075029 | 3/2013 |
| WO | WO 2013/059630 | 4/2013 |
| WO | WO 2013/059638 | 4/2013 |
| WO | WO 2013/066748 | 5/2013 |
| WO | WO 2013/082003 | 6/2013 |
| WO | WO 2013/101550 | 7/2013 |
| WO | WO 2013/184698 | 12/2013 |
| WO | WO 2014/120981 | 8/2014 |
| WO | WO 2014/120982 | 8/2014 |
| WO | WO 2014/137929 | 9/2014 |
| WO | WO 2014/185995 | 11/2014 |

OTHER PUBLICATIONS

U.S. Appl. No. 60/392,350, filed Jun. 28, 2002, Storer.
U.S. Appl. No. 60/392,351, filed Jun. 28, 2002, Gosselin.
U.S. Appl. No. 61/119,723, filed Dec. 3, 2008, Li et al.
U.S. Appl. No. 61/214,884, filed Sep. 30, 2010, Li et al.

Abonyi, et al., "Ribavirin in the Treatment of Hepatitis C", Anticancer Res, (2005) 25:1315-1320.
Adam, et al., "On the temperature dependence of cooperative relaxation properties in glass-forming liquids," *J. Chem. Phys.*, (1965), 43:139-146.
Adiwijaya, et al., "A Viral Dynamic Model for Treatment Regimens with Direct-acting Antivirals for Chronic Hepatitis C Infection," *PLoS Computational Biology*, (2012), 8(1): 1-11.
Afdhal, et al., "Hepatitis C pharmacogenetics: State of the art in 2010", Hepatology, (2011) 53(1 ): 336-345.
Angell, "Formation of Glasses from Liquids and Biopolymers," *Science*, Mar 31, 1995; 267(5206):1924-35.
Angell, "The old problems of glass and the glass transition, and the many new twists" *Proc Natl Acad Sci U S A.*, Jul 18, 1995; 92(15):6675-82.
Anonymous, "View of NCT01726517 on 2012_12_10: A Phase 2, Randomized, Open-Label Study of Sofosbuvir/Gs-5885 Fixed Does Combination +/– Ribavirin in Subjects with Chronic Genotype 1 HCV Infection", ClinicalTrials.gov Archive, http://clinicaltrials.gov/archive/NCT01726517/2012_12_10, retrieved on Mar. 14, 2014.
Anonymous, "View of NCT01726517 on 2013_05_13: A Phase 2, Randomized, Open-Label Study of Sofosbuvir/GS-5885 Fixed Dos Combination +/– Ribavirin in Subjects with Chronic Genotype 1 HCV Infection", Clinical Trials.gov Archive, http://clinicaltrials.giv/archive/NCT01726517/2013_05_13, retrieved on Mar. 14, 2014.
Appel, et al., "Mutational Analysis of Hepatitis C Virus Nonstructural Protein 5A Potential Role of Differential Phosphorylation in RNA Replication and Identification of a Genetically Flexible Domain", Journal of Virology, (2005), 79(5):3187-3194.
Artursson, et al., "Caco-2 monolayers in experimental and theoretical predictions of drug transports," *Adv Drug Deliv Rev.*, (1996), 22:67-84.
Asselah, et al., "New direct-acting antivirals' combination for the treatment of chronic hepatitis C", Liver International, (2011), 31:68-77.
Asselah, et al., "Daclatasvir plus sofosbuvir for HCV infection: An oral combination therapy with high antiviral efficacy," *Journal of Hepatology*, (2014), 61(2), 435-438.
Asselah, et al., "Gene expression and hepatitis C virus infection", Gut, (2009) 58: 846-858.
Asselah, et al., "IL28B polymorphism is associated with treatment response in patients with genotype 4 chronic hepatitis C", J Hepatology (2012) 56: 527-532.
Avdeef, "Absorption and drug development: solubility, permeability, and charge state," *Wiley-Interscience*, (2003), 277-351.
Bailey, et al., "The use of intestinal epithelial cell culture model, Caco-2, in pharmaceutical development," *Adv Drug Deliv Rev.*, (1996), 22:85-103.
Baird, et al., "A classification system to assess the crystallization tendency of organic molecules from undercooled melts," *J Pharm Sci.*, Sep. 2010;99(9):3787-806.
Balzarini, et al., "Mechanism of anti-HIV action of masked alaninyl d4t-MP derivatives" PNAS, (1996), 93:7295-7299.
BASF Pamphlet entitled "The right path to greater solubility and bioavailability. BASF excipients for solubilization," (2011) located at http://www.pharma-ingredients.basf.com/Documents/ENP/Brochure/EN/Brochure_Solubilizer.pdf.
Battaglia, et al., "Combination Therapy with Interferon and Ribavirin in the Treatment of Chronic Hepatitis C Infection", The Annals of Pharmacotherapy, (2000), 34(4):487-494.
Belema, et al., "Discovery and Development of Hepatitis C Virus NS5A Replication Complex Inhibitors", Journal of Medicinal Chemistry, ASAP, (2014), pp. 1-30.
Belema, et al., "Preparation of bi-1H-benzimidazoles end-capped with amino acid or peptide derivatives as hepatitis C virus inhibitors", CAPLUS an 2010: 175961, 2 pages.
Beten, et al., "Controlled-release coevaporates of dipyridamole prepared with acrylic polymers," *Intl J Pharmaceutics*, (1994), 103(3): 243-251.

(56) References Cited

OTHER PUBLICATIONS

Bhat, "Synthesis and Pharmacokinetic Properties of Nucleoside Analogues as Possible Inhibitors of HCV RNA Replication", Oral Session V: Hepatitis C Virus, Flaviviruses, 16th International Conference on Antiviral Research, (Apr. 27-May 1, 2003, Savannah, GA) Abstract # 120, p. A75.
BMS Press Release, "Bristol-Myers Squibb to Present New Data Demonstrating Company's Continuing Commitment to Research and Development in Liver Disease at the American Association for the Study of Liver Diseases (AASLD) Annual Meeting," Oct. 16, 2012, 7 pages.
BMS Press Release, "European Commission Approves Bristol-Myers Squibb's Daklinza (daclatasvir) Across Multiple Genotypes for the Treatment of Chronic Hepatitis C Infection," Aug. 27, 2014, 4 pages.
BMS Press Release, "Investigational Triple DAA Regimen of Daclatasvir, Asunaprevir and BMS-791325 Achieved SVR12 of 94% in Treatment-Naïve Patients with Genotype 1 Chronic Hepatitis C Infection in Phase II Trial," Nov. 12, 2012, 4 pages.
BMS Press Release, "New 12 Week, Interferon-Free Treatment Arms Added to All-Oral Combination Study of PSI-7977 and Daclatasvir (BMS-790052) for HCV Genotype 1," Nov. 4, 2011, 4 pages.
Bodenheimer, et al., "Tolerance and Efficacy of Oral Ribavirin Treatment of Chronic Hepatitis C: A Multicenter Trial", Hepatology, (1997), 26(2):473-477.
Bonkovsky, et al., "Comparative Effects of Different Doses of Ribavirin Plus Interferon-alpha2b for Therapy of Chronic Hepatitis C: Results of a Controlled, Randomized Trial", Digestive Dis & Sci, (2001), 46(10):2051-2059.
Borawski, et al., "Class III Phosphatidylinositol 4-Kinase Alpha and Beta Are Novel Host Factor Regulators of Hepatitis C Virus Replication", Journal of Virology, (2009), 83(19):10058-10074.
Bourliere, "Chronic hepatitis C: Treatments of the future", Clin Res Hepatology & Gastroenterology, (2011), 35: S84-S95.
Breitenbach, "Melt extrusion can bring new benefits to HIV therapy," *American Journal of Drug Delivery*, (2006), 4(2): 61-64.
Butler, et al., "The developability classification system: application of biopharmaceutics concepts to formulation development," *J Pharm Sci.*, Dec. 2010, 99(12):4940-54.
Cahard, et al., "Aryloxy Phosphoramidate Triesters as Pro-Tides," Mini-Reviews in Medicinal Chemisty, (2004), 4:371-381.
Caira, "Crystalline Polymorphism of Organic Compounds", Topics in Current Chemistry, (1998), 198:163-208.
Chang, et al., "Deoxycytidine-resistant Stereoisomer Is the Active Form of (+)-2',3'-Dideoxy-3'-thiacytidine in the Inhibition of Hepatitis B Virus Replication", J Bio Chem, (1992), 267(20):13938-13942.
Chemello, et al., "The Effect of Interferon Alfa and Ribavirin Combination Therapy in Naive Patients with Chronic Hepatitis C", J Hepatology, (1995), 23(Suppl. 2):8-12.
Chemical Abstracts Registry No. 1256391-55-5, indexed in the Registry file on STN CAS Online Dec. 13, 2010.
Cheng, et al., "Antiviral Activity and Resistance Profile of the Novel HCV NS5A Inhibitor GS-5885", presentation at EASL Barcelona, Spain, Apr. 18-22, 2012.
Chiou, et al., "Crystallization of Amorphous Components in Spray Dried Powders", Drying Technology, Taylor & Francis, Philadelphia, PA, US, (2007), 25:1427-1435.
Chiou, et al., "Pharmaceutical Applications of Solid Dispersion Systems," J Pharm Sci, (1971), 60(9):1281-1302.
Chung, et al., "Highlights of AASLD 2011, CCO Official Conference Coverage of the 2011 Annual Meeting of the American Association for the Study of Liver Diseases," Nov. 4-8, 2011, San Francisco, California.
Cihlar, et al., "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131", Antimicrobial Agents and Chemotherapy, (2008), 52(2):655-665.

Clark, et al., "Synthesis and antiviral activity of 2'-deoxy-2'-fluoro-2'-C-methyl purine nucleosides as inhibitors of hepatitis C virus RNA replication", Bioorg Med Chem Lett, (2006) 16: 1712-1715.
Clark, "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, (2005), 48(17): 5504-5508.
Clinical trial NCT01455090, BMS-650032, BMS-790052 and BMS-791325 for 12 weeks, Oct. 18, 2011.
Clinical trial NCT01466790, 7977+TMC-435 +/−ribavirin for 12 weeks, Nov. 7, 2011.
Clinical Trial NCT01826981, 5885+7977+GS-9669 and 5885+7977 for 12 weeks, HCV Genotype 1 patients, Aug. 14, 2014.
Clinical trial NCT02098616, Asunaprevir, daclatasvir and BMS-791325 +/− ribavirin for 8 weeks, Mar. 27, 2014.
Clinical Trial NCT02133131, MK-5172+MK-8742+sofosbuvir for 4-8 weeks, HCV Genotype 1 patients, Aug. 26, 2014.
Clinical Trial NCT02226549, 5885+7977+vedroprevir +/− ribavirin for 8 weeks, HCV Genotype 1 patients, Aug. 25, 2014.
Codington, et al., "Nucleosides XVIII Synthesis of 2'-Fluorothymidine, 2'-Fluorodeoxyuridine, and Other 2'-Halogeno-2'-deoxy Nucleosides-s 1'2", The Division of Nucleoprotein Chemistry, Sloan-Kettering Institute for Cancer Research, Sloan-Kettering Division of Cornell University Medical College, New York 21, New York, (1963), 29:558-564.
Cornpropst, et al., "The Effect of Renal Impairment and End Stage Renal Disease on the Single-Dose Pharmacokinetics of GS-7977", J Hepatology, (2012), 56:S433 (Abstract #1101).
Cotton, et al., "Reactivity of cytosine and thymine in single-base-pair mismatches with hydroxylamine and osmium tetroxide and its application to the study of mutations", Proc Natl Acad Sci USA, (1988), 85: 4397-4401.
Cotton, et al., "Current methods of mutation detection", Mutal Res, (1993), 285:125-144.
Crowley, et al., "The use of thermal methods for predicting glass-former fragility," *Thermochemica Acta*, (2001), 308:79-93.
Custodio, et al., "Predicting drug disposition, absorption/elimination/transporter interplay and the role of food on drug absorption," *Adv Drug Deliv Rev.*, Mar 17, 2008;60(6):717-33.
Dahan, et al., "Prediction of solubility and permeability class membership: provisional BCS classification of the world's top oral drugs," *AAPS J*, 11(4): 740-6.
Dahari, et al., "Triphasic Decline of Hepatitis C Virus RNA During Antiviral Therapy," *Hepatology*, (2007), 46(1) 16-21.
Das, et al., "Preparation of dialkyl, dialkenyl and dialkynyl arylene, heteroarylene, heterocyclylene and cycloalkylene linked benzimdazole-imidazoles and related compounds end capped with amino acids or peptide derivatives for treating and preventing flavivirus infections", CAPLUS an 2011: 1236910, 2 pages.
Davis, "Current Therapy for Chronic Hepatitis C", Gastroenterology, (2000), 118: SI04-SI14.
Defrancesco, et al., "New therapies on the horizon for hepatitis C: are we close?", Clin Liver Dis, (2003), 7:211-242.
Delaney, "HBV & HCV: Parallels, Contrasts and Future Directions for Therapy," slides for presentation in the 25th ICAR (International Conference on Antiviral Research) presented on Apr. 18, 2012.
Di Bisceglie, et al., "Ribavirin as Therapy for Chronic Hepatitis C", Annals of Internal Medicine, (1995), 123(12): 897-903.
Dienstag and McHutchison et al., "American Gastroenterological Association technical review on the management of hepatitis C", Gastroenterology, (2006), 130: 231-264.
Dixit, et al., "Modelling how ribavirin improves interferon response rates in hepatitis C virus infection," *Nature*, (2004) 432: 922-924.
Dressman, et al., "Mixing-tank model for predicting dissolution rate control or oral absorption." *J Pharm Sci.*, Feb. 1986;75(2):109-16.
Dusheiko, et al., "Ribavirin Treatment for Patients with Chronic Hepatitis C: Results of a Placebo-Controlled Study", J Hepatology, (1996), 25:591-598.
Earnings Call Transcript of Gilead Sciences Inc's Q1 2012 Results on Apr. 26, 2012.
Egan, et al., "Prediction of intestinal permeability," *Adv Drug Deliv Rev.*, Mar 31, 2002;54(3):273-289.

(56) References Cited

OTHER PUBLICATIONS

Elazar, et al., "Amphipathic Helix-Dependent Localization of NS5A Mediates Hepatitis C Virus RNA Replication", Journal of Virology, (2003), 77(10):6055-6061.
Evans, et al., "Phosphorylation of hepatitis C virus nonstructural protein 5A modulates its protein interactions and viral RNA replication", PNAS, (2004),101 (35), 13038-13043.
Flamm, "Chronic Hepatitis C Virus Infection", J Am Med Assoc, (2003), 289(18):2413-17.
FOURward Study (NCT02175966), Daclatasvir, Asunaprevir, BMS-791325 and Sofosbuvir for 4-12 weeks, HCV Genotype 1 treatment naïve patients, Jun. 25, 2014, 4 pages.
Franciscus, "Hepatitis C Treatments in Current Clinical Development", HCV Advocate, (Mar. 2010), pp. 1-26.
Freundt, et al., "Interfering with interferons: Hepatitis C virus counters innate immunity", PNAS, (2005), 102(49):17539-17540.
Fried, et al., "PegyinterferonAlfa-2a Plus Ribavirin for Chronic Hepatitis C Virus Infection", New England Journal of Medicine, (2002), 324(13):975-982.
Furman, et al., "The Anti-Hepatitis B Virus Activities, Cytoxicities, and Anabolic Profiles of the (−) and (+) Enantiomers of cis-5-Fluoro-1-[2-(Hydroxymenthyl)-1,3-Ozathiolan-5-yl]Cytosine", Antimicrobial Agents and Chemotherapy, (1992), 36(2):2686-2692.
Gane, et al., "Once Daily GS-7977 Plus Ribavirin in HGV Genotypes 1-3: The ELECTRON Trial", Presented at the 47th Annual Meeting of the European Association for the Study of the Liver (Apr. 18-22, 2012), Barcelona, Spain (Poster #1113).
Gane, et al., "Once Daily PSI-7977 Plus RBV: Pegylated Interferon-Alfa Not Required for Complete Rapid Viral Response in Treatment-Naive Patients with HGV GT2 or GT3", Hepatology, (2011), 54(4 Suppl): 377 A (Abstract #34 ).
Gane, "Future Hepatitis C Virus Treatment: Interferon-Sparing Combinations", Liver International, (2011), 31(S1 ): 62-67.
Gane, "Future Treatment for Chronic Hepatitis C: IFN or Ribavirin-Free Regimens", Hepatol Int, (2012), 6:16-17 (Abstract #TCS10-03).
Gane, et al. "Efficacy of nucleotide polymerase inhibitor sofosbuvir plus the NS5A inhibitor ledipasvir or the NS5B non-nucleoside inhibitor GS-9669 against HCV genotype 1 infection", Gastroenterology. Mar. 2014;146(3):736-743.e1. doi: 10.1053/j.gastro.2013. 11.007. Epub Nov. 18, 2013.
Gane, et al. "Once daily Sofosbuvir/Ledipasvir fixed dose combination with or without Ribavirin: the ELECTRON trial", Heptology. Oct. 2013; 58(4)(Suppl):243A.
Gane, et al., "Electron: Once Daily PSI-7977 Plus RBV in HGV GT1/2/3", J Hepatology, (2012), 56:S438-S439 (Abstract #1113).
Gane, et al., "Mericitabine and ritonavir-boosted danoprevir with or without ribavirin in treatment-naive HCV genotype 1 patients: INFORM-SVR study," Liver International, Jan. 2015; 35(1):79-89.
Gao, et al., "Chemical genetics strategy identifies an HCV NS5A inhibitor with a potent clinical effect", Nature, (2010), 465(6):96-102.
Gao, et al., "New BMSs HCV NS5A Inhibitor: From Screen Hit to Clinic", (2010), pp. 1-9 [http://www.natao.onz/2008/HCV/101408_01.htm].
Gastaminza, et al., "Antiviral Stilbene 1,2 Diamines Prevent Initiation of Hepatitis C Virus RNA Replication at the Outset of Infection", Journal of Virology, (2011 ), 85(11 ):5513-5523.
Ge, et al., "Genetic variation in IL28B predicts hepatitis C treatment-induced viral clearance", Nature (2009) 461 (17): 399-401.
German, et al., "Lack of Clinically Significant Pharmacokinetic Drug-Drug Interaction Between Sofosbuvir (GS-7977) and GS-5885 or GS-9669 in Health Volunteers", 63rd Annual Meeting of the American Association for the Study of Liver Diseases, Hepatology. vol. 56(4)(Suppl) Abstract 1072A-1073A, 2012.
Gilead announces interim results of ELECTRON and QUANTUM studies, showing that HCV RNA could no longer be detected 4 weeks after treatment completed, Apr. 19, 2012, 3 pages.
Gilead Sciences Press Release "European Medicines Agency Validates Gilead's Marketing Application for Ledipasvir/Sofosbuvir Fixed-Dose Combination Tablet for Genotype 1 Chronic Hepatitis C Infection", Mar. 27, 2014.
Gilead Sciences Press Release, "Gilead Announces U.S. FDA Priority Review Designation for Ledipasvir/Sofosbuvir Fixed-Dose Combination Tablet for Chronic Hepatitis C Genotype 1 Infection", Apr. 7, 2014.
Graeser, et al., "Applying thermodynamic and kineticparameters to predict the physical stability of two differently prepared amorphous forms of simvastatin," Curr Drug Deliv., Aug. 2009; 6(4):374-82.
Graeser, et al., "Correlating thermodynamic and kinetic parameters with amorphous stability," Eur J Pharm Sci, Jun. 28, 2009;37(3-4):492-8.
Graeser, et al., "The role of configurational entropy in amorphous systems," Pharmaceutics, (2010), 2:224-44.
Griffith, et al., "HCV Anti-viral Agents", Annual Reports in Medicinal Chemistry, (2004), 39:223-237.
GS-7977 Structure provided by Chembest Research Laboratories Ltd., (2013), 2 pages, [http://biochembest.com/product_detail.asp?m=2&id=1178&classid1=65&nclassid=195].
Guedj, et al., "Second-Phase Hepatitis C Virus RNA Decline During Telaprevir-Based Therapy Increases With Drug Effectiveness: Implications for Treatment Duration," Hepatology, (2011) 53(6):1801-08.
Guedj, et al., "Understanding hepatitis C viral dynamics with direct-acting antiviral agents due to the interplay between intracellular replication and cellular infection dynamics," J Theor Biol, (2010) 257:330-40.
Guillory, "Generation of Polymorphs, Hydrates, Solvates, and Amorphous Solids", Polymorphism in Pharmaceutical Solids, edited by Harry G. Brittain, Marcel Decker, Inc., Milford, New Jersey (1999), pp. 183-226.
Gunic, "6-Hydrazinopurine 2'-methyl ribonucleosides and their 5'-monophosphate prodrugs as potent hepatitis C virus inhibitors," Bioorg & Med Chem Letters, (2007), 17(9): 2456-2458.
Gunic, et al., " Cyclic monophosphate prodrugs of base=modified 2'-C-methyl ribonucleosides as potent inhibitors of hepatitis C virus RNA replication", Bioorg Med Chem Lett, (2007), 17(9):2456-2458.
Hancock, et al., "Molecular mobility of amorphous pharmaceuticals determined using differential scanning calorimetry," Thermochemica Acta, (2001), 3: 95-107.
Hayashi et al., "PCT-SSCP: a method for detection of mutations", Genet Anal Techn,(1992), 9: 73-79.
Hepatitis C, (2012), 1 pages, [http://en.wikipedia.org/wiki/Hepatitis C].
Hézode, et al., "Oral combination therapy: Future hepatitis C virus treatment?" Journal of Hepatology, (2011) 55:933-935.
Hijikata, et al., "Two Distinct Proteinase Activities Required for the Processing of a Putative Nonstructural Precursor Protein of Hepatitis C Virus", J Viral, (1993), 67(8):4665-4675.
Hilfiker, et al., "Relevance of Solid-state Properties for Pharmaceutical Products", Polymorphism in the Pharmaceutical Industry, edited by Rolf Hilfiker, (2006), pp. 1-19.
Hodge, "Adam-Gibbs formulation of enthalpy relaxation near the glass transition," J Res Natl Inst Stand Technol., (1997), 102: 195-205.
Hrebabecky, et al., "Synthesis of 1-(3-azido-2,3-dide-oxy-4-C-hydroxymethyl-alpha-L-threopentofuranosyl) thymine, 1-(2,3-dideoxy-4-C-hydroxy-methyl-alpha-L-glycero-pentofuranosyl)thymine and 1-(2,3-dideoxy-4-C-hydroxymethyl-alpha-L-glycero-pent-2-enofuranosyl)thymine", Collect Czech Chem Commun, (1992), 58: 409-420.
Hrebabecky, et al., "Synthesis of 1-(3-azido-2,3-dideoxy-β-D-allofuranosyl)thymine, 1-(2,3-dideoxy-β-Dallofuranosyl) thymine, and 1-(2,3-dideoxy-—-D-erythro-hex-2-enofuranosyl)thymine", Carbohydrate Research, (1991), 216:179-186.
Huang, et al., "Phosphorylation of hepatitis C virus NS5A nonstructural protein: a new paradigm for phosphorylation-dependent viral RNA replication?", Virology, (2007), 364:1-9.

(56) References Cited

OTHER PUBLICATIONS

Hughes, et al., "Domain III of NS5A contributes to both RNA replication and assembly of hepatitis C virus particles", Journal of General Virology, (2009), 90:1329-1334.
International Preliminary Report on Patentability and Written Opinion for PCT/US2011/064017 dated Jun. 25, 2013 (8 pages).
International Preliminary Report on Patentability and Written Opinion for PCT/US2012/055621 dated Mar. 27, 2014 (7 pages).
International Preliminary Report on Patentability and Written Opinion for PCT/US2014/013953 dated Apr. 15, 2015 (14 pages).
International Search Report and Written Opinion for PCT/US2011/060966 dated Sep. 19, 2012 (40 pages).
International Search Report and Written Opinion for PCT/US2014/013954 dated Apr. 28, 2014 (10 pages).
International Search Report and Written Opinion for PCT/US2010/034600 dated Sep. 9, 2010 (13 pages).
International Search Report for PCT/US2011/064017 dated Jun. 28, 2012 (13 pages).
International Search Report for PCT/US2012/055621 dated Apr. 26, 2013 (10 pages).
International Search Report and Written Opinion for PCT/US2012/065681 dated Jan. 25, 2013 (8 pages).
International Search Report and Written Opinion for PCT/US2013/044148 dated Aug. 16, 2013 (9 pages).
International Search Report and Written Opinion for PCT/US2013/044138, dated Oct. 15, 2013 (22 pages).
International Search Report for PCT/US2014/013953 dated Apr. 28, 2014 (9 pages).
ION Study (NCT01701401), 7977+5885 +/− ribavirin for 12-24 weeks, HCV genotype 1 patients, Oct. 4, 2012, 4 pages.
Ishi, et al., "Expression of Hepatitis C Virus NS5B Protein: Characterization of Its RNA Polymerase Activity and RNA Binding", Heptology, (1999), 29: 1227-1235.
Iyer, et al. "Synthesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)," Journal of Medicinal Chemistry, (2000), 43:2266-2274.
Jacobson, et al., "PSI-7977 400 mg OD Safety and Tolerability in the First 450 Patients Treated for 12 Weeks", J Hepatology,(2012), 56:S441 (Abstract #1120).
Jacobson, "GS-7977 400 mg OD Safety and Tolerability in the Over 500 Patients Treated for at Least 12 Weeks", Presented at the 47th Annual Meeting of the European Association for the Study of the Liver, (Apr. 18-22, 2012), Barcelona, Spain (Poster #1120).
Janssens, et al., "Evaluation of the formulation of solid dispersions by co-spray drying itraconazole with Inutec SP1, a polymeric surfactant, in combination with PVPVA 64." *Eur J Pharm Biopharm.*, Oct. 2008;70(2): 500-5.
Janssens, et al., "Formulation and characterization of ternary solid dispersions made up of Itraconazole and two excipients, TPGS 1000 and PVPVA 64, that were selected based on a supersaturation screening study," *Eur J Pharm Biopharm.*, May 2008; 69(1): 158-66.
Janssens, et al., "Review: physical chemistry of solid dispersions," *J Pharm Pharmacol.*, Dec. 2009;61(12):1571-86.
Jones, "Minireview: Nucleotide Prodrugs," Antiviral Research, (1995), 27:1-17.
Jones, et al., "In-cell click labeling of small molecules to determine subcellular localisation", J Chem Biol, (2011), 4:49-53.
Jorgensen, et al., "Prediction of drug solubility from structure." *Adv Drug Deliv Rev.*, Mar. 31, 2002;54(3):355-66.
Kanda, et al., "Inhibition of Intrahepatic Gamma Interferon Production by Hepatitis C Virus Nonstructural Protein 5A in Transgenic Mice", Journal of Virology, (2009), 83(17):8463-8469.
Karmwar, et al., "Investigation of properties and recrystallization behavior of amorphous indomethacin samples prepared by different methods," *Int J Pharm.*, Sep. 30, 2011;417(1-2):94-100.

Katze, et al., "Ser2194 Is a Highly Conserved Major Phosphorylation Site of the Hepatitis C Virus Nonstructural Protein NS5A", Virology, (2000), 278:501-513.
Kaul, et al., "Essential Role of Cyclophilin A for Hepatitis C Virus Replication and Virus Production and Possible Link to Polyprotein Cleavage Kinetics", PLoSPathogens, (2009), 5(8):1-18.
Kim, et al., "Direct Measurement of Nucleoside Monophosphate Delivery from a Phosphoramidate Pronucleotide by Stable Isotope Labeling and LC-ESI—MS/MS," Molecular Pharmaceutics, (2004), 1(2):102-111.
Klumpp, et al., "The Novel Nucleoside Analog R1479(4'-Azidocytidine) Is a Potent Inhibitor of NS5B-dependent RCA Synthesis and Hepatitis C Virus Replication in Cell Culture", J Bio Chem, (2006), 281:3793-3799.
Kowdley, et al., "Atomic: 97% RVR for PSI-7977 + PEG/RBV x 12 Week Regimen in HGV GT1: An End to Response-Guided Therapy?", J Hepatology (2012) 56:S1 (Abstract #1).
Krieger, et al., "Enhancement of Hepatitis C Virus RNA Replication by Cell Culture-Adaptive Mutations", Journal of Virology, (2001), 75(10):4614-4624.
Kriegs, et al., The Hepatitis C Virus Non-Structural NS5A Protein Impairs Both the Innate and Adaptive Hepatic Immune Response In Vivo, The Journal of Biological Chemistry, (2009), 284:28343-28351.
Kwo, et al., "Efficacy of boceprevir, an NS3 protease inhibitor, in combination with peginterferon alfa-2b and ribavirin in treatment-naive patients with genotype 1 hepatitis C infection (SPRINT-1): an open-label, randomised, multicentre phase 2 trial", Lancet, (2010), 376(9742):705-16.
Lalezari, et al., "Once Daily PSI-7977 Plus PegIFN/RBV in a Phase 28 Trial: Rapid Virologic Suppression in Treatment-Naive Patients with HGV GT2/GT3", J Hepatology, (2011), 54:S28 (Abstract #61).
Landowski, et al, "Targeted delivery to PEPT1-overexpressing cells: Acidic, basic, and secondary floxuridine amino acid ester prodrugs", MCT, (2005), 4(4):659-667.
Lawitz, et al, "The Effect of Hepatic Impairment on the Safety, Pharmacokinetics, and Antiviral Activity of GS-7977 in Hepatitis C Infected Subjects Treated for Seven Days", Presented at the 47th Annual Meeting of the European Association for the Study of the Liver, (Apr. 18-22, 2012), Barcelona, Spain (Poster #1130).
Lawitz, et al. Sofosbuvir and ledipasvir fixed-dose combination with and without ribavirin in treatment-naive and previously treated patients with genotype 1 hepatitis C virus infection (LONESTAR): an open-label, randomised, phase 2 trial. Lancet. Feb. 8, 2014;383(9916):515-23. doi: 10.1016/S0140-6736(13)62121-2. Epub Nov. 5, 2013.
Lawitz, et al., "2008: Dose-Ranging, Three-Day Monotherapy Study of the HCV NS3 Protease Inhibitor GS-9256", Journal of Heptology, (2010), 52:S466-S467.
Lawitz, et al., "Once Daily Dual-Nucleotide Combination of PSI-938 and PSI-7977 Provides 94% HGV RNA <LOD at Day 14: First Purine/Pyrimidine Clinical Combination Data (The Nuclear Study)", J Hepatology, (2011), 54:S543 (Abstract #1370).
Lawitz, et al., "Once-Daily PSI-7977 Plus PEG/RBV in Treatment-Naive Patients with HGV GT1: Robust End of Treatment Response Rates Are Sustained Post-Treatment", J Hepatology, (2011), 54(4 Suppl):472A-473A (Abstract #225).
Lawitz, et al., "PSI-7977 Proton and Electron: 100% Concordance of SVR4 with SVR24 in HGV GT1, GT2 & GT3", J Hepatology, (2012), 56:S4 (Abstract #7).
Lawitz, et al., "The Effect of Hepatic Impairment on the Pharmacokinetics and Antiviral Activity of PSI-7977 in Hepatitis C Infected Subjects Treated for Seven Days", J Hepatology, (2012), 56:S445-S446 (Abstract #1130).
Lawitz, et al., "A 12-Week Trial of Interferon-free Regimens Containing ABT-450/r and ABT-267 ± Ribavirin (RBV) in Treatment-naive Patients With HCV Genotypes 1-3," *National Aids Treatment Advocacy Project*, Jun. 9, 2013; located at http://www.natap.org/2013/APASL/APASL_01.htm.

(56) References Cited

OTHER PUBLICATIONS

Lawitz, et al., "A phase 1, randomized, placebo-controlled, 3-day, dose-ranging study of GS-5885, an NS5A inhibitor, in patients with genotype 1 hepatitis C," *Journal of Hepatology*, Feb. 5, 2012; 57(1):24-31, located at http://dx.doi.org/10.1016/j.jhep.2011.12.029.

Lawitz, et al., "Three-Day, Dose-Ranging Study of the HCV NS5A Inhibitor GS-5885," a poster for presentation in 46th EASL annual meeting held in Mar. 30 to Apr. 3, 2011.

Lawitz, et al., "Three-Day, Dose-Ranging Study of the HCV NS5A Inhibitor GS-5885," *National Aids Treatment Advocacy Project*, Apr. 6, 2011 located at http://www.natap.org/2011/EASL/EASL_68.htm.

Lee, et al., "Selective Intracellular Activation of a Novel Prodrug of the Human Immunodeficiency Virus reverse Transcriptase Inhibitor Tenofovir Leads to Preferential Distribution and Accumulation in Lymphatic Tissue," Antimicrobial Agents and Chemotherapy, (2005), 49(5):1898-1906.

Lee, et al., "The hepatitis C virus NS5A inhibitor (BMS-790052) alters the subcellular localization of the non-structural viral protein", Virology, (2011), 414:10-18.

Lemm, et al., "Discovery of Potent Hepatitis C Virus NS5A Inhibitors with Dimeric Structures", AAC Accepts, (2011) pp. 1-30.

Lemm, et al., "Identification of Hepatitis C Virus NS5A Inhibitors", Journal of Virology, (2010), 84(1):482-491.

Leuner, et al., "Improving drug solubility for oral delivery using solid dispersions," *European Journal of Pharmaceutics and Biopharmaceutics*, (2000) 50: 47-60.

Levin, "High Rate of Sustained Virologic Reponses with Response with All Oral Combination Daclatasvir (NS5A Inhibitor) Plus Sofosbuvir (Nucleotide NS5B Inhibitor), With or Without Ribavirin, in Treatment-Naïve Patients Chronically Infected with HCV GT 1, 2, or 3", Nov. 1, 2012, Retrieved from the Internet: http://www.natap.org/2012/AASLC/AASLD_06.htm [retrieved on Apr. 24, 2014].

Lewis, et al., "Second Generation Direct Antiviral and the Way to Interferon-Free Regimens in Chronic HGV", Best Practices & Research: Clinical Gastroenterology, (2012), 26:471-485.

Lin, et al., "A stereospecific synthesis of 2',3'-dideoxy-β-L-cytidine (β-L-ddC), a potent inhibitor against human hepatitis B virus (HBV) and human immunodeficiency virus (HIV)", Tetrahedron Letters, (1994), 35(21):3477-3480.

Lindh, et al., "Interleukin 28B Gene Variation at rs12979860 Determines Early Viral Kinetics During Treatment in Patients Carrying Genotypes 2 or 3 of Hepatitis C Virus", J Infect Dis, (2011) 203: 1748-1752.

Liu, et al., "Water-Insoluble Drug Formulation" 2nd ed, (CRC Press, 2008), Ch. 18 Development of Solid Dispersion for Poorly Water Soluble Drugs, p. 499-523.

Livercancer, 2011, http://www.mayoclinic.com/health/liver-cancer/DS00399/DSECTION=causes.

Lohmann, et al., "Mutations in Hepatitis C Virus RNAs Conferring Cell Culture Adaptation", Journal of Virology, (2001), 75(3):1437-1449.

Lok, et al., "Combination Therapy with BMS-790052 and BMS-650032 Alone or with PEGINF/RBV Results in Undetectable HCV RNA through 12 Weeks of Therapy in HCV Genotype 1 Null Responders," *Hepatology*, (2010), 55(4) 877A.

Lok, et al., "Combination Therapy with BMS-790052 and BMS-650032 Alone or with Pegylated Interferon and Ribavirin (pegIFN/RBV) Results in Undetectable HCV RNA Through 12 Weeks of Therapy in HCV Genotype 1 Null Responders", AASLD, The Liver Meeting in Boston, MA, Oct. 29-Nov. 2, 2010, poster.

Lonestar Study (NCT01726517), 7977+5885 +/− ribavirin for 8-12 weeks, HCV genotype 1 patients, Nov. 10, 2012.

Ma, "Characterization of the Metabolic Activation of Hepatitis C Virus Nucleoside Inhibitor B-D-2'-Deoxy-2-Fluro-2'-C-Methylcytidine (PSI-6130) and Identification of a Novel Active 5'-Triphosphate Species," The Journal of Biological Chemistry, (2007), 282(41): 29812-29820.

Ma, et al., "Characterization of the Intracellular Metabolism of β-d-2'-Deoxy-2'-Fluoro-2'-C-Methyl-Cytidine and the Inhibition of HCV Polymerase NS5B by its 5'-Triphosphate Species," Antiviral Research, (2007), 74(3): A36; Abstract 23.

MacDonald, et al., "Hepatitis C virus NS5A: tales of a promiscuous protein", Journal of General Virology, (2004), 85:2485-2502.

Mangia, et al., "An IL28B Polymorphism Determines Treatment Response of Hepatitis C Virus Genotype 2 or 3 Patients Who Do Not Achieve a Rapid Virologic Response", Gastroenterology, (2010), 139: 821-827.

Mao, et al., "Time-dependence of molecular mobility during structural relaxation and its impact on organic amorphous solids: an investigation based on a calorimetric approach," *Pharm Res.*, Aug. 2006;23(8):1906-17.

Marsac, et al., "A comparison of the physical stability of amorphous felodipine and nifedipine systems," *Pharm Res,*. Oct. 2006;23(10):2306-16.

Martel-Laferriere, et al., "GS-7977: a promising nucleotide analog NS5B polymerase inhibitor of HCV", Future Virol, (2012) 7(6):537-546.

McCarthy, et al., "Replicated Association Between an IL28B Gene Variant and a Sustained Response to Pegylated Interferon and Ribavirin", Gastroenterology, (2010) 138: 2307-2314.

McCormick, et al., "Tagging of NS5A expressed from a functional hepatitis C virus replicon", Journal of General Virology, (2006), 87:635-640.

McGuigan, "Phosphoramidate derivatives of d4T as inhibitors of HIV: The effect of amino acid variation," Antiviral Research, (1997), 35(3):95-204.

McGuigan, "Phosphoramidate derivatives of stavudine as inhibitors of HIV: unnatural amino acids may substitute for alanine", Antiviral Chemistry & Chemotherapy, (2000), 11:111-116.

McGuigan, et al. "Aryl Phosphoramidate Derivatives of d4T Have Improved Anti-HIV Efficacy in Tissue Culture and May Act by the Generation of a Novel Intracellular Metabolite," Journal of Medicinal Chemistry, (1996), 39:1748-1753.

McGuigan, et al. "Application of Phosphoramidate Pro Tide Technology Significantly Improves Antiviral Potency of Carbocyclic Adenosine Derivatives" Journal of Medicinal Chemistry, (2006), 49:7215-7726.

McGuigan, et al., "Certain Phosphoramidate Derivatives of Dideoxy Uridine (ddU) Are Active Against HIV and Successfully By-pass Thymidine Kinase," FEBS Letters, (1994), 351:11-14.

McGuigan, et al., "Sub Micromolar Inhibitors of HCV Generated from Inactive Nucleosides by Application of ProTide Technology," Antiviral Research, (2007), 74(3): A36; Abstract 24.

McHutchison, et al., "Telaprevir with Peginterferon and Ribavirin for Chronic HGV Genotype 1 Infection", N Engl J Med, (2009), 360(18):1827-1838.

Metatla, et al., "The Vogel-Fulcher-Tamman equation investigated by atomistic simulation with regard to the Adam-Gibbs model" Macromolecules 2007, 40(26):9680-9685.

Mills, World Health Organization "Pharmaceutical excipients—an overview including consideration for paefiatric dosing", Federation Internataional Pharm, (Jun. 2010), 44 pages.

Missiha, et al., "Disease Progression in Chronic Hepatitis C: Modifiable and Nonmodifiable Factors", Gastroenterology (2008), 134:1699-1714.

Miyanari, et al., "Hepatitis C Virus Non-structural Proteins in the Probable Membranous Compartment Function in Viral Genome Replication", The Journal of Biological Chemistry, (2003), 278(50):50301-50308.

Moghaddam, et al., "IL28B genetic variation and treatment response in patients with hepatitis C virus genotype 3 infection", Hepatology, (2011), 53(3): 746-754.

Moradpour, et al., "Replication of hepatitis C virus", Nature Reviews Microbiology, (2007),5:453-463.

Mourier, et al., "Enantioselective synthesis and biological evaluation of 5-o-carboranyl-pyrimidinenucleosides", Bioorganic & Medicinal Chemistry, (1999), 7:2759-2766.

Muhlberger, et al. HCV-related burden of disease in Europe: a systematic assessment of incidence, prevalence, morbidity, and

(56) References Cited

OTHER PUBLICATIONS mortality. Liver Cancer, 2011, BMC Public Health20099:34. http://www.biomedcentral.com/1471-2458/9/34.

Mukaizawa, et al., "Novel oral absorption system containing polyamines and bile salts enhances drug transport via both transcellular and paracellular pathways across Caco-2 cell monolayers." Int J Pharm., Feb. 9, 2009;367(1-2):103-8.

Murakami, et al. "Mechanism of activation of PSI-7851 and its diastereoisomer PSI-7977", J. Biol. Chem. 2010; 285:34337-34347.

Murakami, et al., "The Mechanism of Action of β-D-2'-Deoxy-2'-Fluoro-2'-C-Methylcytidine involves a second metabolic pathway leading to β-D-2'-Deoxy-2'-Fluoro-2'-C-Methylcytidine 5'-Triphosphate, a potent Inhibitor of the Hepatitis C Virus RNA-Dependent RNA Polymerase," Antimicrobial Agents and Chemotherapy, (2008), 52(2):458-464.

Murakami, et al., "The Mechanism of Action of β-D-2'-Deoxy-2'-Fluoro-2'-C-Methylcytidine Inhibition of Hepatitis C Virus NS5B RNA Polymerase," Antimicrobial Agents and Chemotherapy, (2007), 51(2):503-509.

Myers, et al., "Detection of Single Base Substitutions by Ribonuclease Cleavage at Mismatches in RNA:DNA Duplexes", Science, (1985), 230:1242-1246.

Myers, et al., "Detection of single base substitutions in total genomic DNA", Nature, (1985) 313: 495-498.

NATAP Report of Cheng, "Antiviral Activity and Resistance Profile of the Novel HCV NS5A Inhibitor GS-5885", presentation at EASL Barcelona, Spain, Apr. 18-22, 2012.

NATAP Report of Everson, "An Interferon-Free, Ribavirin-Free 12-Week Regimen of Daclatasvir (DCV), Asunaprevir (ASV) and BMS-791325 Yielded SVR4 of 94% in Treatment-Naïve Patients with Genotype (GT) 1 Chronic Hepatitis C Virus (HCV) Infection", presentation at AASLD, Boston, Nov. 9-12, 2012.

NATAP Report of Gane, "PSI-7977: ELECTRON Interferon is not required for Sustained Virologic Response in Treatment-Naïve Patients with HCV GT2 or GT3", AASLD, Nov. 6-9, 2011.

NATAP Report of Lawitz et al, "Once daily dual-nucleotide combination of PSI-938 and PSI-7977 provides 94% HCV RNA <LOD at day 14: First purine/pyrimidine clinical combination data (The Nuclear Study)" EASL Mar. 30-Apr. 3, 2011.

NATAP Report of M Sulkowski, "Potent Viral Suppression With the All-Oral Combination of Daclatasvir (NS5A Inhibitor) and GS-7977 (Nucleotide NS5B Inhibitor), +/− Ribavirin, in Treatment-Naive Patients With Chronic HCV GT1, 2, or 3", EASL Barcelona, Spain, Apr. 18-22, 2012.

Nelson, et al., "Once Daily PSI-7977 Plus PEF-IFN/RBV in HCV GT1: 98% Rapid Virologic Response, Complete Early Virologic Response: The Proton Study", J Hepatology, (2011 ), 54:S544 (Abstract #1372).

Neumann, et al., "Hepatitis C Viral Dynamics in Vivo and the Antiviral Efficacy of Interferon-α Therapy," Science, (1998) 282:103.

Newman, et al., "Assessing the Performance of Amorphous Solid Dispersions", J Pharm Sci., (2012), 101(4): 1355-1377.

Ochoa, et al., "Determination of cell membrane permeability in concentrated cell ensembles." Biophys J., Nov. 1987;52(5):763-74.

Office Action dated Apr. 3, 2015 for U.S. Appl. No. 14/168,264.

Office Action dated Jul. 1, 2016 for U.S. Appl. No. 14/868,062.

Orita, et al., "Detection of polymorphisms of DNA by gel electrophoresis as single-strand conformation polymorphisms", Proc. Natl Acad Sci, USA, (1989), 86:2766-2770.

Patterson, et al., "Melt extrusion and spray drying of carbamazepine and dipyridamole with polyvinylpyrrolidone/vinyl acetate copolymers," Drug Dev Ind Pharm., Jan. 2008;34(1): 95-106.

Pawlotsky, et al., "Antiviral Action of Ribavirin in Chronic Hepatitis C", Gastroenterology, (2004) 126:703-714.

Perrone, et al. "First Example of Phosphoramidate Approach Applied to a 4' Substituted Purine Nucleoside (4'-Azidoadenosine): Conversion of an Inactive Nucleoside to a Submicromolar Compound versus Hepatitis C Virus" Journal of Medicinal Chemistry, (2007), 50:5463-5470.

Perrone, et al., "Design Synthesis and Biological Evalyation of Novel Nucleoside Phorphoramidates as Potential Anti-HCV Agents", Antiviral Research, (2006), 70:Abstract 100, 6 pages.

Perrone, Thesis entitled "Design Synthesis and Biological Evaluation of Novel Nucleotide Prodrugs as Potential Anti-Hepatitis C Virus Agents", Welsh School of Pharmacy, Cardiff University, (Feb. 2007), 292 pages.

Pietschmann, et al., "Characterization of Cell Lines Carrying Self-Replicating Hepatitis C Virus RNAs", Journal of Virology, (2001), 75(3):1252-1264.

Piper Jaffray Report on Gilead Sciences Inc., Nov. 21, 2011, 9 pages.

Pockros, et al., "High relapse rate seen at week 72 for patients treated with R1626 combination therapy", Hepatology, (2008) 48(4): 1349-1350.

Pockros, et al., "R1626 Plus Peginterferon Alfa-2a Provides Potent Suppression of Hepatitis C Virus RNA and Significant Antiviral Synergy in Combination with Ribavirin", Hepatology, (2008), 48(2):385-397.

Poordad, et al., "Rapid Virologic Response: A New Milestone in the Management of Chronic Hepatitis C", Clin Infectious Diseases (2008), 46:78-84.

Poordad, et al., "A 12-Week Interferon-Free Regimen of ABT-450/r + ABT-333 + Ribavirin Achieved SVR12 in More Than 90% of Treatment-naïve HGV Genotype-1-Infected Subjects and 47% of Previous Non-Respoders", EASL 47th Annual Meeting, Barcelona, Spain (Apr. 18-22, 2012), 9 pages.

Press Release, Gilead Sciences, Inc., "Gilead Announces Early Sustained Virologic Response Rates for GS-7977 Plus Ribavin in Genotype 1 Hepatitis C Patients", (Apr. 19, 2012), 2 pages.

Press Release, Gilead Sciences, Inc., "Gilead Announces Sustained Virologic Response Data for 12-Week Regimen of GS-7977 Plus Pegylated Interferon and Ribavin in Genotype 1 Hepatitis C Patients", (Apr. 19, 2012), 2 pages.

Program of the $25^{th}$ ICAR, abstract of pp. 1 to 12.

Quaroni, et al., "Development of intestinal cell culture models for drug transport and metabolism studies." Adv Drug Deliv Rev., (1996), 22:3-52.

Rauch, et al., "Genetic variation in IL28B is associated with chronic hepatitis C and treatment failure: a genome-wide association study", Gastroenterology, (2010,) 138: 1338-1345.

Reed, et al., "The NS5A Proteins of Viruses from Three Genera of the Family Flaviviridae Are Phosphorylated by Associated Serine/Threonine Kinases", Journal of Virology, (2001), 75(3), 1252-1264.

Reichard, et al., "Therapy of Hepatitis C: Alpha Interferon and Ribavirin", Hepatology, (1997) 26(3, Suppl. 1):108S-111S.

Revised BMS/Pharmasset trial protocol for NCT01359644, May 24, 2011.

Revised BMS/Pharmasset trial protocol for NCT01359644, Jan. 5, 2012.

Revised ELECTRON protocol (NCT01260350), arms 21 and 22 added for 7977+5885 +/− ribavirin for 6 weeks in treatment-naïve, HCV genotype 1 patients, Nov. 20, 2012.

Revised ELECTRON trial protocol for NCT01260350, May 7, 2012.

Revised Protocol for NCT01260350 dated Jul. 9, 2012.

Revised Protocol for NCT01466790, Nov. 7, 2011.

Revised Protocol for NCT01701401 dated Oct. 4, 2012.

Reynolds, et al., "Thermodynamics of Ligand Binding and Efficiency", ACS Medicinal Chemistry Letters, (2011) pp. A-E.

Robins, et al., "Nucleic acid related compounds, 91, Biomimetic reactions are in harmony with loss of 2'-substituents as free radicals (not anions) during mechanism-based inactivation of ribonucleotide reductases, differential interactions of azide, halogen, and alkylthio groups with tributylstannane and triphenylsilane", Journal of the American Chemical Society, (1996), 118(46):11341-11348.

Rodriguez-Torres, et al., "Antiviral activity, pharmacokinetics, safety, and tolerability of PSI-7851, a novel nucleotide polymerase inhibitor for HCV, following single and 3 day multiple ascending oral doses in healthy volunteers and patients with chronic HCV infection", Hepatology, (2009), 50(6):11A (Abstract LB17).

(56) References Cited

OTHER PUBLICATIONS

Romine, et al., "Inhibitors of HCV NS5A: From Iminothiazolidinones to Symmetrical Stilbenes", ACS Med Chem Lett. Jan. 11, 2011;2(3):224-9. doi: 10.1021/ml1002647. eCollection 2011.
Rong, et al., "Rapid Emergence of Protease Inhibitor Resistance in Hepatitis C Virus," Science Translational Medicine, (2010), 30(2): 1-9.
Ruebsam, et al., "Pyrrol[1,2-b]pyridazin-2-ones as potent inhibitors of HCV NS5B polymerase", Bio Org Med Chem Lett, (2008), 18:3616-3621.
Saboulard, et al. "Characterization of the Activation Pathway of Phosphoramidate Triester Prodrugs of Stavudine and Zidovudine" American Society for Pharmacology and Experimental Therapeutics, (1999), 56, 693-704.
Sakurai, et al., "Polymer Combination Increased Both Physical Stability and Oral Absorption of Solid Dispersions Containing a Low Glass Transition Temperature Drug: Physicochemical Characterization and In Vivo Study," Chem Pharm Bull (Tokyo), (2012), 60(4): 459-64.
Saleeba, et al., "Chemical Cleavage of Mismatch to Detect Mutations", Methods of Enzymology, (1993), 217;286-295.
Sarrazin, et al., "Importance of IL28B gene polymorphisms in hepatitis C virus genotype 2 and 3 infected patients", J Hepatology, (2011), 54: 415-421.
Scheel, et al., "Recombinant HCV Variants with NS5A from Genotypes 1-7 Have Different Sensitivities to an NS5A Inhibitor but Not interferon-α", Gastroenterology, (2011 ), 140(3), 1032-1042.
Schlutter, et al., "New drugs hit the target" Nature, (2011), 474 S5.
Schmitz, et al., "NS5A—From Obscurity to New Target for HCV Therapy", Recent Patents on Anti-Infective Drug Discovery, (2008), 3:77-92.
Shamblin, et al., "Characterization of the time scales of molecular motion in pharmaceutically important glasses" J Phys Chem B, (1999), 103(20): 4113-21.
Sharp, "BMS-790052/BMS-650032 Combo Cures Hepatitis C without Interferon", HIV and Hepatitis.com Coverage of the 46th Annual Meeting of the European Association for the Study of the Liver, Mar. 30-Apr. 3, 2011, Berlin, Germany, 3 pages.
Shimakami, et al., "Hepatitis C: Recent Successes and Continuing Challenges in the Development of Improved Treatment Modalities", Curr Opin Pharmacol, (2009), 9(5):537-544.
Slide presentation shown during Gilead Sciences Inc's "Q4 2011 Earnings Call" on Feb. 2, 2012.
Snoeck, et al., "A Comprehensive Hepatitis C Viral Kinetic Model Explaining Cure", Clinical Pharmacology & Therapeutics, (2010), 87: 706-713.
Sofia, "Nucleotide prodrugs for HCV therapy", Antivir Chem.& Chemother, (2011), 22:23-49.
Sofia, et al., "Nucleoside, Nucleotide, and Non-Nucleoside Inhibitors of Hepatitis C Virus NS5B RNA-Dependent RNA-Polymerase", J Med Chem, (2012), 55:2481-2531.
Sofia, et al., "Discovery of a β-D-2'-Deoxy-α-fluoro-2'-β-C-methyluridine Nucleotide Prodrug (PSI-7977) for the Treatment of Hepatitis C Virus", Journal of Medicinal Chemistry, (2010), 53(19):7202-7218.
Sofia, et al., "β-D-2'-Deoxy-2;fluro-2'-C-methyluridine Phosphoramidates: Potent and Selective Inhibitors of HCV RNA Replication," (Sep. 2007), Poster P-259, 1 page.
Stephens, et al., "Haplotype Variation and Linkage Disequilibrium in 313 Human Genes", Science ,(2001), 293:489-493.
Sulkowski, et al., "High Sustained Virological Response Rate in Treatment-Naïve HCV Genotype 1A and 1B patients treated for 12 Weeks with an Interferon-Free All-Oral Quad Regimen: Interim Results" (2012) 56 Journal of Hepatology s560.
Sulkowski, et al., "Potent Viral Suppression With the All-Oral Combination of Daclatasvir (NS5A Inhibitor) and GS-7977 (Nucleotide NS5B Inhibitor), +/− Ribavirin, in Treatment-Naive Patients With Chronic HCV GT1, 2, or 3 (100% SVR gt1, 91% gt2)", EASL Barcelona, Spain, Apr. 18-22, 2012. Poster 1422.

Sulkowski, et al., "Potent Viral Suppression With the All-Oral Combination of Daclatasvir (NS5A Inhibitor) and GS-7977 (Nucleotide NS5B Inhibitor), +/− Ribavirin, in Treatment-Naive Patients With Chronic HCV GT1, 2, or 3," Journal of Hepatology, (2012), 56:S560 (Abstract #1422).
Suppiah, et al., "IL28B is associated with response to chronic hepatitis C interferon-αand ribavirin therapy ", Nature Genetics, (2009), 41 (10): 1100-1104.
Suzuki, et al., Sustained virological response in a patient with chronic hepatitis C treated by monotherapy with the NS3-4A protease inhibitor telaprevir, Journal of Clinical Virology, 2010, vol. 47, pp. 76-78.
Tan, "Hepatits C Therapeutics: Current Status and Emerging Strategies", Nature Rev Drug Discov, (2002), 1:867-881.
Tanabe, et al., "Synergistic Inhibition of Intracellular Hepatitis C Virus Replication by Combination of Ribavirin and Interferon-alpha", J Infect Dis, (2004), 189(7):1129-1139.
Tanaka, et al., "Genome-wide association of IL28B with response to pegylated interferon-alpha and ribavirin therapy for chronic hepatitis C", Nature Genetics, (2009,) 41 (10): 1105-1109.
Tellinghuisen, et al., "Regulation of Hepatitis C Virion Production via Phosphorylation of the NS5A Protein", PLoS Pathogens, (2008), 4(3):1-17.
Tellinghuisen, et al., "Structure of the Zinc-Binding Domain of an Essential Replicase Component of Hepatitis C Virus Reveals a Novel Fold", Nature, (2005), 435(19):374-379.
Tellinghuisen, et al., "The NS5A Protein of Hepatitis C Virus Is a Zinc Metalloprotein", Journal of Biological Chemistry, (2004), 279(47):48576-48587.
Transcript of Biotechnology Industry Organization (BIO) CEO and Investor Conference, Feb. 14, 2012.
Transcript of Gilead Sciences Inc's "Q4 2011 Earnings Call Transcript" on Feb. 2, 2012.
Trousdale, et al., "Activity of 1-(2'-Fluoro-2'-Deoxy-β-D-Arabinofuranosyl)Thymine Against Herpes Simplex Virus in Cell Cultures and Rabbit Eyes", Antimicrobial Agents and Chemotherapy, (1983), 23(6):808-813.
Tung, et al., "Formulation of solid dispersion of rebamipide evaluated in a rat model for improved bioavailability and efficacy." J Pharm Pharmacol., Dec. 2011;63(12):1539-47.
Understanding Hepatitis C—Prevention, (2014), 3 pages, [http://www.webmd.com/hepatitis/understanding-hepatitis-c-prevention].
Van Rompaey, et al., "Mycobacterium tuberculosis thymidine monophosphate kinase inhibitors; biological evaluation and conformational analysis of 2'-and 3'-modified thymidine analogues", Eur J Org Chem, (2003) pp. 2911-2918.
Vanheusden, et al., "Discovery of bicyclic thymidine analogues as selective and high-affinity inhibitors of Mycobacterium tuberculosis thymidine monophosphate kinase", J Med Chem, (2004), 47:6187-6194.
Vasconcelos, et al., "Solid dispersions as strategy to improve oral bioavailability of poor water soluble drugs," Drug Discov Today, (2007), 12:1068-1075.
Vitale, et al, "2-Arylbenzimidazoles as Antiviral and Antiproliferative Agents—Part 1", Medicinal Chemistry, 4: 605-615 (2008).
Volpe, "Application of method suitability for drug permeability classification." AAPS J., Dec. 2010;12(4):670-8.
Von Wagner, et al., "Peginterferon-alpha-2a (40KD) and ribavirin for 16 or 24 weeks in patients with genotype 2 or 3 chronic hepatitis C", Gastroenterology, (2005), 129:522-527.
Walter, et al., "Permeability of small nonelectrolytes through lipid bilayer membranes."J Membr Biol., (1986), 90(3):207-17.
Wang, et al., "Solid state characteristics of ternary solid dispersions composed of PVP VA64, Myrj 52 and itraconazole." Int J Pharm., Oct. 13, 2005;303(1-2):54-61.
Wyles, et al., "Synergy of Small Molecular Inhibitors of Hepatitis C Virus Replication Directed at Multiple Viral Targets," J. Virol., (2007), 81(6):3005-3008.
Xu, et al., "Preparation and evaluation of Ibuprofen solid dispersion systems with kollidon particles using a pulse combustion dryer system," Chem Pharm Bull (Tokyo), Nov. 2007;55(11): 1545-50.
Yakuji Shinso Kenkyukai, "Iyakuhin Seizo Shishi 2001," Sep. 30, 2013, Jiho Inc., cover page, pp. 283 to 284, colophon.

(56) References Cited

OTHER PUBLICATIONS

Yoshioka, et al., "Crystallization of indomethacin from the amorphous state below and above its glass transition temperature," *J Pharm Sci.*, Dec. 1994;83(12):1700-5.

Yu, "Amorphous pharmaceutical solids: preparation, characterization and stabilization," *Adv Drug Deliv Rev.*, May 16, 2001;48(1):27-42.

Yu, et al., "In vitro efficacy of approved and experimental antivirals against novel genotypes 3 hepatitis C virus subgenomic replicons", Antiviral Research, (2013), 100(2):439-445.

Zemlicka, "Lipophilic phosporamidates as antiviral pornucleotides", Biochem Biophys Acta, (2002), pp. 276-286.

Zennou, et al., "Combination of two complementary nucleotide analogues, PSI-7977 and PSI-938, effectively clears wild type and NS5b: S282T HCV replicons—Comparison with combinations of other antiviral compounds," Conferences Reports for NATAP, EASL 45th Annual Meeting Apr. 14-18, 2010, Vienna Austria, (http://www.natap.org/2010/EASL/EASL_28.htm).

Zeuzem, et al., "Review article: management of patients with chronic hepatitis C virus infection and 'normal' alanine aminotransferase activity", Aliment Pharmacol & Ther, (2006), 24:1133-1149.

Zhou, et al., "Physical stability of amorphous pharmaceuticals: Importance of configurational thermodynamic quantities and molecular mobility," *J Pharm Sci.*, Aug. 2002;91(8):1863-72.

Zhu, et al, "Virologic Analysis of HGV Genotype 1 Patient Samples from the PROTON Study", Presented at the 47th Annual Meeting of the European Association for the Study of the Liver (Apr. 18-22, 2012), Barcelona, Spain (Poster #1217).

Zhu, et al., "Design and synthesis of HCV agents with sequential triple inhibitory potentials", Bioorg & Med Chem Lett., (2010), 20(17):5212-5213.

Office Action and Search Report for AP Application No. AP/P/2015/008630 dated Jul. 26, 2017 (5 pages).

Office Action for CO Application No. 15-203.177 dated Apr. 11, 2017 (14 pages).

Examination Report for EP Application No. 14704502.5 dated Feb. 17, 2017 (5 pages).

Examination Report for GC Application No. GC 2014-26346 dated Apr. 19, 2017 (3 pages).

Office Action for Israeli Patent Application No. 233416 dated May 22, 2017 (2 pages).

Second Office Action for Mexican Patent Application No. MX/2017/31547 dated May 8, 2017 (14 pages).

Further Examination Report for New Zealand Patent Application No. 625087 dated Mar. 13, 2017 (2 pages).

First Examination Report for New Zealand Patent Application No. 729172 dated Mar. 13, 2017 (2 pages).

Search Report for Panamanian Patent Application No. 90777 dated Feb. 12, 2017 (1 page).

COMBINATION FORMULATION OF TWO ANTIVIRAL COMPOUNDS

CROSS-REFERENCE TO RELATED APPLICATIONS

This application is a continuation of U.S. application Ser. No. 14/868,062, filed Sep. 28, 2015, which is a continuation of U.S. application Ser. No. 14/168,264, filed Jan. 30, 2014, which claims the benefit under 35 U.S.C. § 119(e) to U.S. Provisional Application No. 61/759,320, filed on Jan. 31, 2013, U.S. Provisional Application No. 61/772,292, filed on Mar. 4, 2013, U.S. Provisional Application No. 61/828,899, filed on May 30, 2013, U.S. Provisional Application No. 61/870,729, filed on Aug. 27, 2013, U.S. Provisional Application No. 61/897,793, filed on Oct. 30, 2013, and U.S. Provisional Application No. 61/907,332, filed on Nov. 21, 2013, the entirety of which are all incorporated herein by reference.

BACKGROUND

Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

Ledipasvir is a selective inhibitor of non-structural protein 5A (NS5A), which has been described previously (see, for example, WO 2010/132601). The chemical name of ledipasvir is (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester.

Sofosbuvir (SOF) is a selective inhibitor of non-structural protein 5B (NS5B) (see, for example, WO 2010/132601 and U.S. Pat. No. 7,964,580). The chemical name of sofosbuvir is (S)-isopropyl 2-(((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl) amino) propanoate.

SUMMARY

The present disclosure provides, in some embodiments, a pharmaceutical composition comprising ledipasvir in a substantially amorphous form and sofosbuvir in a substantially crystalline form.

Ledipasvir has the chemical name of (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester, and has the following chemical formula:

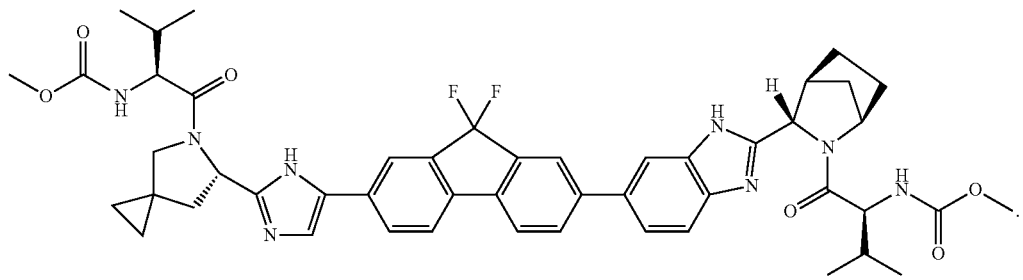

Sofosbuvir (SOF) has the chemical name of (S)-isopropyl 2-(((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino)propanoate and has the following chemical formula:

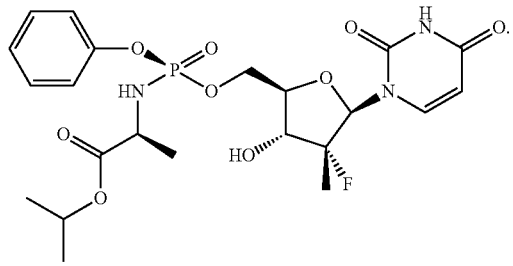 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

In some embodiments, provided is a pharmaceutical composition comprising: a) an effective amount of ledipasvir, wherein ledipasvir is substantially amorphous; and b) an effective amount of sofosbuvir wherein sofosbuvir is substantially crystalline.

Further embodiments of the disclosure relate to pharmaceutical dosage forms and tablets. The disclosure also provides methods for using the combination in the treatment of hepatitis C.

DETAILED DESCRIPTION

1. Definitions

As used in the present specification, the following words and phrases are generally intended to have the meanings as set forth below, except to the extent that the context in which they are used indicates otherwise.

As used herein, the term "about" used in the context of quantitative measurements means the indicated amount ±10%, or alternatively ±5%, or ±1%. For example, with a ±10% range, "about 2:8" can mean 1.8-2.2:7.2-8.8.

The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point).

The term "substantially amorphous" as used herein is intended to mean that greater than 70%; or greater than 75%; or greater than 80%; or greater than 85%; or greater than 90%; or greater than 95%, or greater than 99% of the compound present in a composition is in amorphous form. "Substantially amorphous" can also refer to material which has no more than about 20% crystallinity, or no more than about 10% crystallinity, or no more than about 5% crystallinity, or no more than about 2% crystallinity.

The term "substantially crystalline" as used herein is intended to mean that greater than 70%; or greater than 75%; or greater than 80%; or greater than 85%; or greater than 90%; or greater than 95%, or greater than 99% of the compound present in a composition is in crystalline form. "Substantially crystalline" can also refer to material which has no more than about 20%, or no more than about 10%, or no more than about 5%, or no more than about 2% in the amorphous form.

The term "polymer" refers to a chemical compound or mixture of compounds consisting of repeating structural units created through a process of polymerization. Suitable polymers useful in this invention are described throughout.

The term "polymer matrix" as used herein is defined to mean compositions comprising one or more polymers in which the active agent is dispersed or included within the matrix.

The term "solid dispersion" refers to the dispersion of one or more active agents in a polymer matrix at solid state prepared by a variety of methods, including spray drying, the melting (fusion), solvent, or the melting-solvent method.

Figure 1:
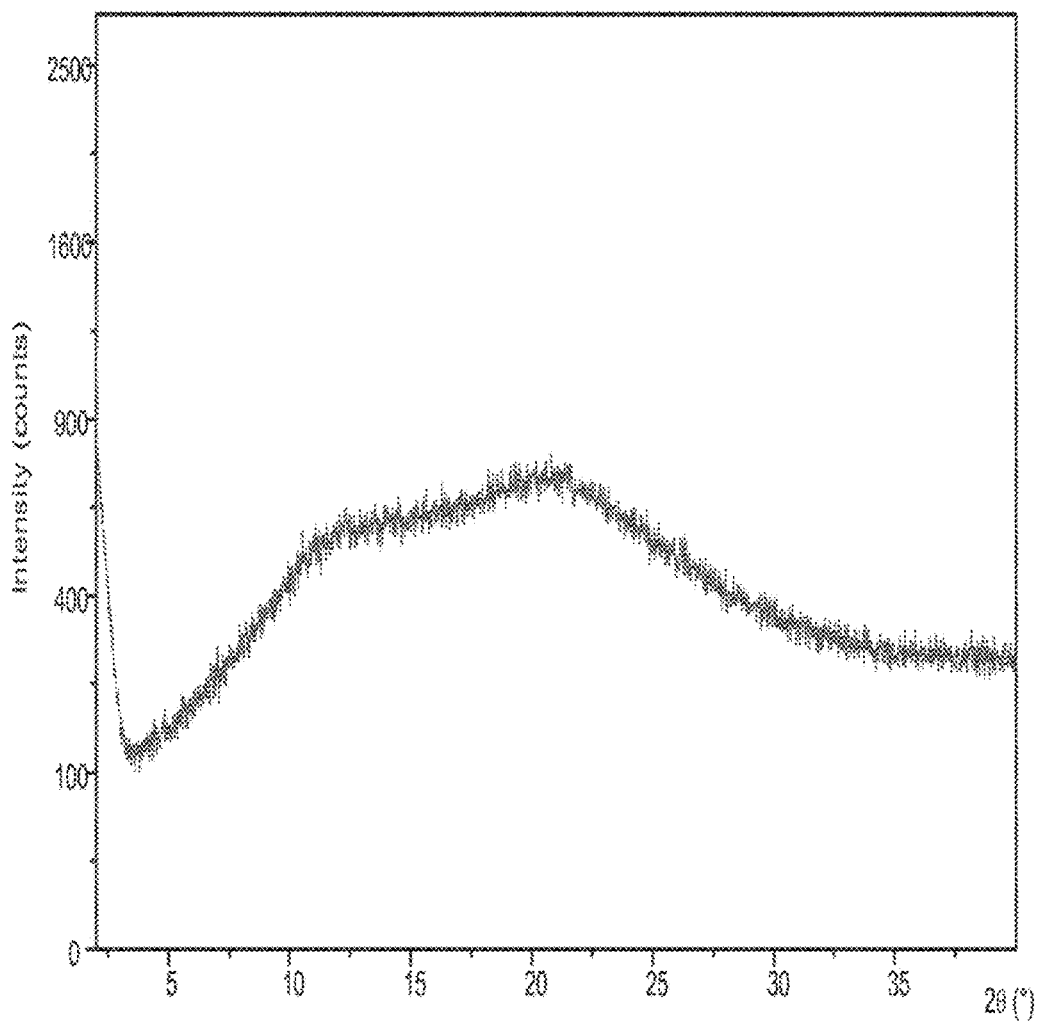
FIG. 1 is a XRPD pattern of the solid dispersion formulation of ledipasvir comprising copovidone in a drug:polymer ratio of 1:1. As shown by the)(RFD, the solid dispersion is in the amorphous state.
Figure 2:
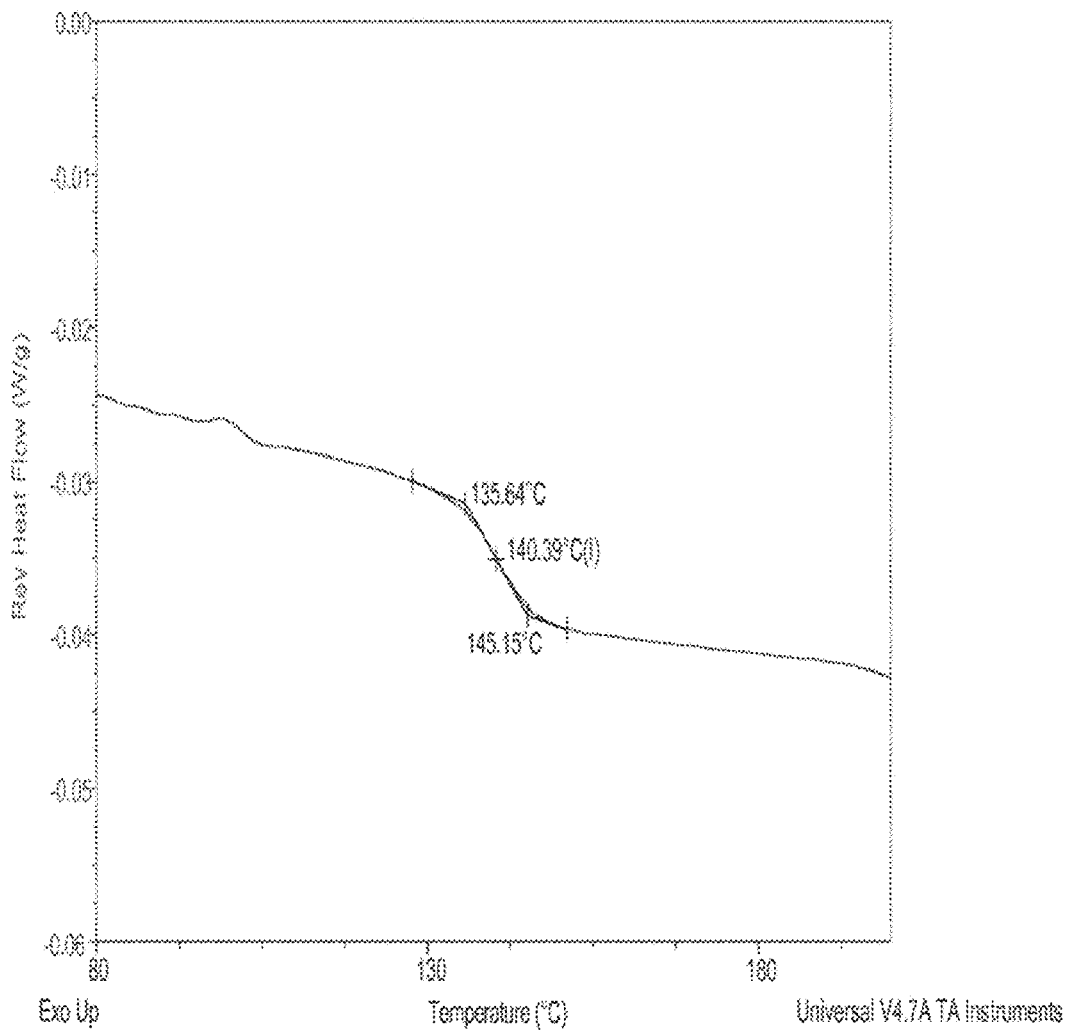
FIG. 2 is a modulated differential scanning calorimetry (DSC) curve of the solid dispersion of ledipasvir comprising copovidone in a drug:polymer ratio of 1:1. The glass transition temperature of the solid dispersion is about 140° C.
Figure 3:
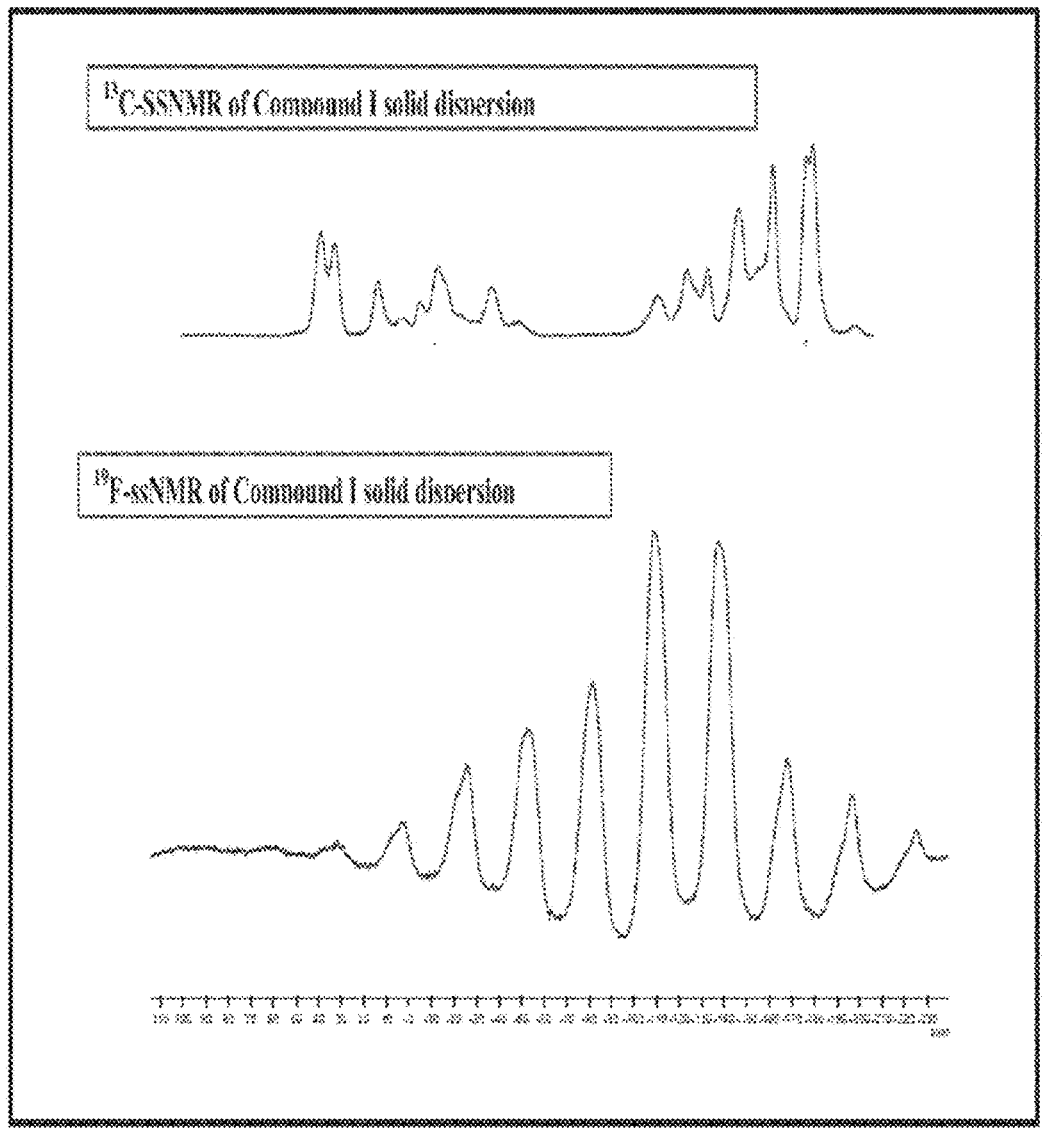
FIG. 3 shows a solid state characterization of the solid dispersion formulation of ledipasvir comprising copovidone in a drug:polymer ratio of 1:1 by solid state nuclear magnetic resonance (SS-NMR).
Figure 4:
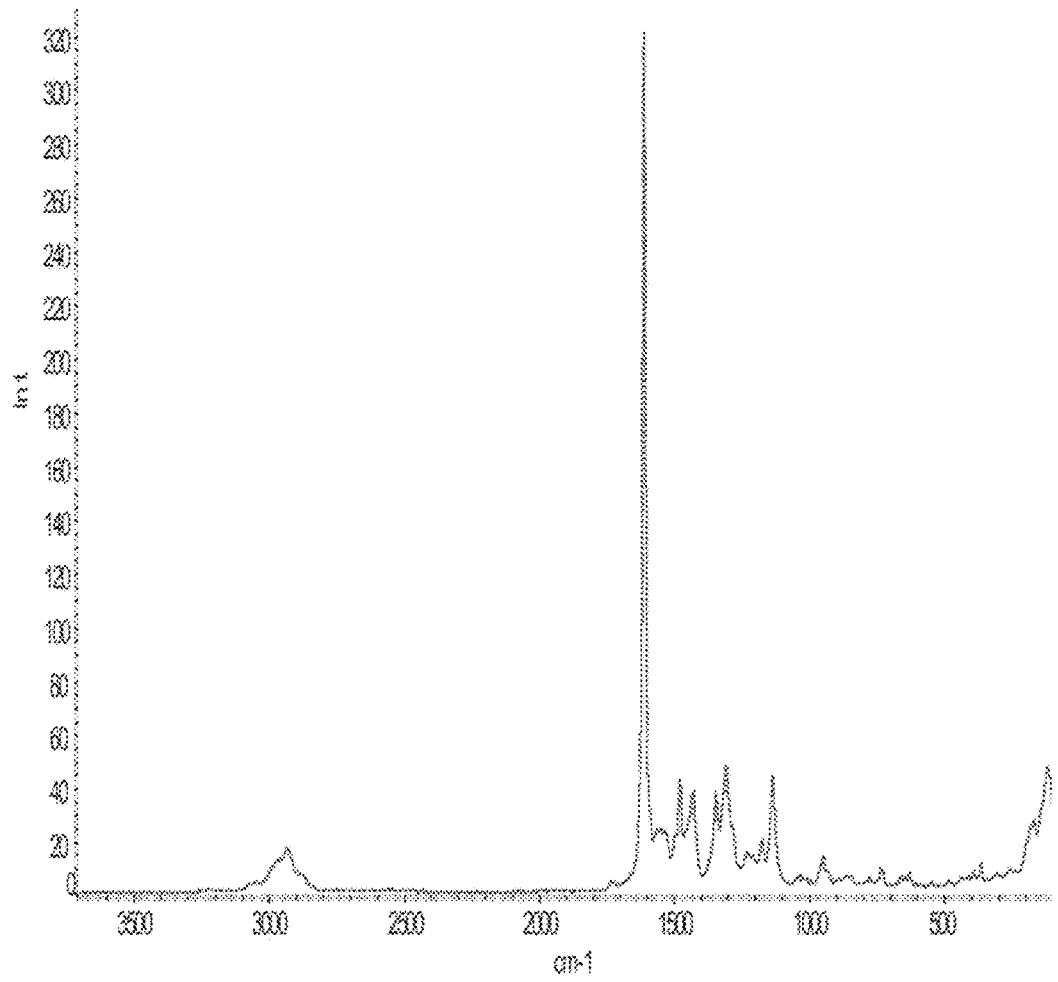
FIG. 4 is a Fourier-transformed Raman spectra of the solid dispersion of ledipasvir comprising copovidone in a drug:polymer ratio of 1:1.

The term "amorphous solid dispersion" as used herein, refers to stable solid dispersions comprising an amorphous active agent and a polymer. By "amorphous active agent," it is meant that the amorphous solid dispersion contains active agent in a substantially amorphous solid state form. In some aspects, as shown by the XRPD in FIG. 1, the solid dispersion is in the amorphous state, and the glass transition temperature of the solid dispersion is about 140° C. (see FIG. 2).

The term "pharmaceutically acceptable" indicates that the material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

The term "pharmaceutically acceptable polymer" refers to a polymer that does not have properties that would cause a reasonably prudent medical practitioner to avoid administration of the material to a patient, taking into consideration the disease or conditions to be treated and the respective route of administration.

The term "carrier" refers to a glidant, diluent, adjuvant, excipient, or vehicle etc with which the compound is administered, without limitation. Examples of carriers are described herein and also in "Remington's Pharmaceutical Sciences" by E. W. Martin.

The term "diluent" refers to chemical compounds that are used to dilute the compound of interest prior to delivery. Diluents can also serve to stabilize compounds. Non-limiting examples of diluents include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "binder" when used herein relates to any pharmaceutically acceptable film which can be used to bind together the active and inert components of the carrier together to maintain cohesive and discrete portions. Non-limiting examples of binders include hydroxypropylcellulose, hydroxypropylmethylcellulose, povidone, copovidone, and ethyl cellulose.

The term "disintegrant" refers to a substance which, upon addition to a solid preparation, facilitates its break-up or disintegration after administration and permits the release of an active ingredient as efficiently as possible to allow for its rapid dissolution. Non-limiting examples of disintegrants include maize starch, sodium starch glycolate, croscarmellose sodium, crospovidone, microcrystalline cellulose, modified corn starch, sodium carboxymethyl starch, povidone, pregelatinized starch, and alginic acid.

The term "lubricant" refers to an excipient which is added to a powder blend to prevent the compacted powder mass from sticking to the equipment during the tabletting or encapsulation process. It aids the ejection of the tablet form the dies, and can improve powder flow. Non-limiting examples of lubricants include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

The term "film coating" refers to a thin, uniform, film on the surface of a substrate (e.g. tablet). Film coatings are particularly useful for protecting the active ingredient from photolytic degradation. Non-limiting examples of film coatings include polyvinylalcohol based, hydroxyethylcellulose, hydroxypropylmethylcellulose, sodium carboxymethylcellulose, polyethylene glycol 4000 and cellulose acetate phthalate film coatings.

The term "glidant" as used herein is intended to mean agents used in tablet and capsule formulations to improve flow-properties during tablet compression and to produce an anti-caking effect. Non-limiting examples of glidants include colloidal silicon dioxide, talc, fumed silica, starch, starch derivatives, and bentonite.

The term "effective amount" refers to an amount that is sufficient to effect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "sustained virologic response" refers to the absence of detectable RNA (or wherein the RNA is below the limit of detection) of a virus (i.e. HCV) in a patient sample (i.e. blood sample) for a specific period of time after discontinuation of a treatment. For example, a SVR at 4 weeks indicates that RNA was not detected or was below the limit of detection in the patient at 4 weeks after discontinuing HCV therapy.

The term "% w/w" as used herein refers to the weight of a component based on the total weight of a composition comprising the component. For example, if component A is present in an amount of 50% w/w in a 100 mg composition, component A is present in an amount of 50 mg.

2. Pharmaceutical Compositions

The pharmaceutical compositions comprise a combination of an effective amount of ledipasvir, wherein ledipasvir is substantially amorphous, and an effective amount of sofosbuvir, wherein sofosbuvir is substantially crystalline.

Such a combination composition, as the experimental examples demonstrate, exhibit unexpected properties. Both sofosbuvir and ledipasvir have previously been demonstrated to act as effective anti-HCV agents. Ledipasvir, when administered alone in a conventional formulation, however, exhibited a negative food effect as evidenced by a roughly 2-fold decrease in exposure when given with a high-fat meal relative to dosing in the fasted state (see, e.g., Tables 10 and 11, Example 3). When ledipasvir is administered in a solid dispersion formulation and in the combination with sofosbuvir, no such negative food effect occurs (Table 12, Example 3).

In the combination composition, ledipasvir is present in a substantially amorphous form. Compared to crystalline agents, amorphous agents are expected to be unstable and have nonlinear solubility and exposure profiles. The data presented herein, however, show that ledipasvir in the combination composition is stable under various conditions, both short-term and long-term, and maintains high and consistent solubility and exposure profiles (Example 6).

Further, according the conventional wisdom, it is not advisable to co-formulate an amorphous agent with a crystalline agent, because the crystals can serve as seeds to induce crystallization of the amorphous agent, leading to instability of the amorphous agent. The current data show that, however, whether co-granulated or co-blended with sofosbuvir in the same layer or integrated as separate layers, ledipasvir stays stable and does not form crystals in the composition (Example 6).

It is also been discovered that, in tablet formations of the combination composition where sofosbuvir and ledipasvir are either co-granulated or co-blended, drug-drug interaction does not occur (Example 7).

A. Ledipasvir

Ledipasvir has previously been described (see, for example, WO 2010/132601) and can be prepared by methods described therein. In one embodiment, the pharmaceutical composition comprises ledipasvir formulated as a solid dispersion dispersed within a polymer matrix formed by a pharmaceutically acceptable polymer. The starting material of the solid dispersion can be a variety of forms of ledipasvir including crystalline forms, amorphous form, salts thereof, solvates thereof and the free base. For example, the acetone solvate, D-tartrate salt, anhydrous crystalline free base, amorphous free base, solvates or desolvates of ledipasvir can be used. Solvates of ledipasvir include, for example, those described in U.S. Publication No. 2013/0324740 (incorporated herein by reference) such as, for example, the monoacetone solvate, diacetone solvate, ethyl acetone solvate, isopropyl acetate solvate, methyl acetate solvate, ethyl formate solvate, acetonitrile solvate, tetrahydrofuran solvate, methyl ethyl ketone solvate, tetrahydrofuran solvate, methyl ethyl ketone solvate, and methyl tert-butyl ether solvate. Particular starting materials contemplated to be useful are the monoacetone solvate, diacetone solvate, anhydrous crystalline free base, D-tartrate salt, anhydrous crystalline free base, and amorphous free base. These forms are characterized and described in U.S. Publication No. 2013/0324496.

After dispersion with the polymer, the solid dispersion is in the amorphous form. FIGS. 1-4 characterize the amorphous solid dispersion comprising ledipasvir. As shown by the XRPD in FIG. 1, the solid dispersion is in the amorphous state, and the glass transition temperature of the solid dispersion is about 140° C.

Various techniques are well known in the art for preparing solid dispersions including, but not limited to melt-extrusion, spray-drying, lyophilization, and solution-evaporation.

Melt-extrusion is the process of embedding a compound in a thermoplastic carrier. The mixture is processed at elevated temperatures and pressures, which disperses the compound in the matrix at a molecular level to form a solid solution. Extruded material can be further processed into a variety of dosage forms, including capsules, tablets and transmucosal systems.

For the solution-evaporation method, the solid dispersion can be prepared by dissolving the compound in a suitable liquid solvent and then incorporating the solution directly into the melt of a polymer, which is then evaporated until a clear, solvent free film is left. The film is further dried to constant weight.

For the lyophilization technique, the compound and carrier can be co-dissolved in a common solvent, frozen and sublimed to obtain a lyophilized molecular dispersion.

For spray dried solid dispersions, the solid dispersion can be made by a) mixing the compound and polymer in a solvent to provide a feed solution; and b) spray drying the feed solution to provide the solid dispersion.

Spray dried solid dispersions of ledipasvir provide improved in vivo and in vitro performance and manufacturability/scalability relative to the other formulation approaches, such as wet and dry granulation formulations. Ledipasvir can be provided either as the free base, D-tartrate salt, crystalline acetone solvate, or other solvate as described herein.

The selection of the polymer for the solid dispersion is based on the stability and physical characteristics of the ledipasvir in the solution. Hypromellose and copovidone solid dispersions both showed adequate stability and physical characteristics. Accordingly, in one embodiment, the polymer used in the solid dispersion is selected from hypromellose and copovidone. Furthermore, the copovidone-based dispersion increased in bioavailability more than the equivalent hypromellose-based formulation (F=30% and 22%, respectively) when prepared at 2:1 API:polymer ratio. Bioavailability of the copovidone-based formulation was further enhanced by increasing the fraction of polymer to a 1:1 ratio, resulting in a bioavailability of 35% in famotidine pretreated dogs.

In one embodiment, the polymer used in the solid dispersion of ledipasvir is hydrophilic. Non-limiting examples of hydrophilic polymers include polysaccharides, polypeptides, cellulose derivatives such as methyl cellulose, sodium carboxymethylcellulose, hydroxyethylcellulose, ethylcellulose, hydroxypropyl methylcellulose acetate-succinate, hydroxypropyl methylcellulose phthalate, cellulose acetate phthalate, hydroxypropylcellulose, povidone, copovidone, hypromellose, pyroxylin, polyethylene oxide, polyvinyl alcohol, and methacrylic acid copolymers.

In a further embodiment, the polymer is non-ionic. Non-ionic polymers showed benefits in screening solubility experiments. Non-limiting examples of non-ionic polymers include hypromellose, copovidone, povidone, methyl cellulose, hydroxyethyl cellulose, hydroxypropyl cellulose, ethylcellulose, pyroxylin, polyethylene oxide, polyvinyl alcohol, polyethylene glycol, and polyvinyl caprolactam-polyvinyl acetate-polyethylene glycol.

In another embodiment, the polymer is ionic. Examples of ionic polymers include hydroxypropyl methylcellulose acetate-succinate, hydroxypropyl methylcellulose phthalate, cellulose acetate phthalate, and methacrylic acid copolymers.

In a further embodiment, the polymer is selected from the group consisting of hypromellose, copovidone, and povidone. Hypromellose and copovidone solid dispersions both showed adequate stability and physical characteristics. A copovidone-based dispersion increased bioavailability more than the equivalent hypromellose-based formulation (F=30% and 22%, respectively) when spray dried at 2:1 ledipasvir:polymer ratio (data not shown). Accordingly, in a specific embodiment, the polymer is copovidone.

In certain embodiments, the weight ratio of ledipasvir to polymer is from about 5:1 to about 1:5. In further embodiments, the weight ratio of ledipasvir to polymer is about 5:1 to about 1:4, or from about 5:1 to about 1:3, or from about 5:1 to about 1:2, or from about 2:1 to about 1:2, or from about 2:1 to about 1:1. In a specific embodiment, the weight ratio of ledipasvir to polymer is about 1:1. In another embodiment, the weight ratio of ledipasvir to polymer is about 2:1. In further embodiments, the weight ratio of ledipasvir to polymer is about 5:1, 1:4, 1:3, or 1:2. Increasing the fraction of polymer to a 1:1 ratio may, in some instances, result in an increased bioavailability. For example, a 1:1 ratio of ledipasvir:copovidone resulted in increased bioavailability (F=35%) in famotidine pretreated dogs.

The solid dispersion comprising ledipasvir may be present in the pharmaceutical composition in a therapeutically effective amount. In some embodiments, the pharmaceutical compositions comprises from about 1% to about 50% w/w of the solid dispersion of ledipasvir. In further embodiments, the composition comprises from about 5% to about 40% w/w, or from about 5% to about 35% w/w, or from about 5% to about 30% w/w, or from about 10% to about 30% w/w, or from about 10% to about 25% w/w, or from about 15% to about 20% w/w of the solid dispersion of ledipasvir. In further embodiments, the pharmaceutical composition comprises about 1% w/w, about 5% w/w, about 10% w/w, about 20% w/w, about 25% w/w, about 30% w/w, about 35% w/w, or about 40% w/w of the solid dispersion of ledipasvir. In a specific embodiment, the pharmaceutical composition comprises about 18% w/w of the solid dispersion of ledipasvir.

Ledipasvir may be present in the pharmaceutical composition in a therapeutically effective amount. In some embodiments, the pharmaceutical compositions comprises from about 1% to about 50% w/w of ledipasvir. In further embodiments, the composition comprises from about 1% to about 40% w/w, or from about 1% to about 30% w/w, or from about 1% to about 20% w/w, or from about 5% to about 15% w/w, or from about 7% to about 12% w/w of ledipasvir. In further embodiments, the pharmaceutical composition comprises about 1% w/w, about 3% w/w, about 5% w/w, about 7% w/w, about 11% w/w, about 13% w/w, about 15% w/w, about 17% w/w, about 20% w/w, about 23% w/w, about 25% w/w, or about 28% w/w, or about 30% w/w of ledipasvir. In a specific embodiment, the pharmaceutical composition comprises about 9% w/w of ledipasvir.

As noted above, after the ledipasvir is mixed with the polymer, the mixture can then be solubilized in a solvent. It is within the skill of those in the art to select an appropriate solvent based on the drug and/or polymer properties such as solubility, glass transition temperature, viscosity, and molecular weight. Acceptable solvents include but are not limited to, water, acetone, methyl acetate, ethyl acetate, chlorinated solvents, ethanol, dichloromethane, and methanol. In one embodiment, the solvent is selected from the group consisting of ethanol, dichloromethane, and methanol. In a further embodiment, the solvent is ethanol or methanol. In a specific embodiment, the solvent is ethanol.

Upon solubilization of the compound and polymer mixture with the solvent, the mixture may then be spray dried. Spray drying is a well known process wherein a liquid feedstock is dispersed into droplets into a drying chamber along with a heated process gas stream to aid in solvent removal and to produce a powder product. Suitable spray drying parameters are known in the art, and it is within the knowledge of a skilled artisan in the field to select appropriate parameters for spray drying. The target feed concentration is generally about 10 to about 50% with a target of about 20% and a viscosity of about 15 to about 300 cP. The inlet temperature of the spray dry apparatus is typically about 50-190° C., while the outlet temperature is about 30-90° C. The two fluid nozzle and hydrolic pressure nozzle can be used to spray dry ledipasvir. The two fluid nozzle gas flow can be about 1-10 kg/hr, the hydrolic pressure nozzle flow can be about 15-300 kg/hr, and the chamber gas flow may be about 25-2500 kg/hr. The spray-dried material typically has particle size ($D_{90}$) under 80 µm. In some instances, a milling step may be used, if desired to further reduce the particle size. Further descriptions of spray drying methods and other techniques for forming amorphous dispersions are provided in U.S. Pat. No. 6,763,607 and U.S. Pat. Pub. No. 2006-0189633, the entirety of each of which is incorporated herein by reference.

Spray drying out of ethanol resulted in high yields (88, 90, 92, 95, 97, 98, 99%) across a wide range of spray-drying outlet temperatures (30-90° C.) with no material accumulation on the spray dry chamber, and the yields obtained from spray drying out of DCM were 60%, 78%, and 44%. Furthermore, ledipasvir demonstrated good chemical stability in the ethanolic feed solution.

B. Sofosbuvir

Sofosbuvir has previously been described in U.S. Pat. No. 7,964,580 and U.S. Publication Nos: 2010/0016251, 2010/0298257, 2011/0251152 and 2012/0107278. Sofosbuvir is provided as substantially crystalline in the pharmaceutical compositions described herein. Examples of preparing crystalline forms of sofosbuvir are disclosed in U.S. Publication Nos: 2010/0298257 and 2011/0251152, both of which are incorporated by reference. Crystalline forms, Forms 1-6, of sofosbuvir are described in U.S. Publication Nos.: 2010/0298257 and 2011/0251152, both of which are incorporated by reference. Forms 1-6 of sofosbuvir have the following characteristic X-ray powder diffraction (XRPD) pattern 2θ-values measured according to the XRPD methods disclosed therein:

(1) 2θ-reflections (°±0.2θ) at about: 7.5, 9.6, and 18.3 (Form 1);
(2) 2θ-reflections (°±0.2θ) at about: 5.0, 7.3, and 18.1 (Form 1);
(3) 2θ-reflections (°±0.2θ) at about: 6.9, 24.7, and 25.1 (Form 2);
(4) 2θ-reflections (°±0.2θ) at about: 19.7, 20.6, and 24.6 (Form 3);
(5) 2θ-reflections (°±0.2θ) at about: 5.0, 6.8, and 24.9 (Form 4);
(6) 2θ-reflections (°±0.2θ) at about: 5.2, 6.6, and 19.1 (Form 5); and
(7) 2θ-reflections (°±0.2θ) at about: 6.1, 20.1, and 20.8 (Form 6).

Form 6, as described in the patent publications above, may be referred to as Form 2, such for example, by the Food and Drug Administration. Forms 1 and 6 are alternatively characterized by the following characteristic XRPD pattern 2θ-values as measured according to the methods disclosed in U.S. Pat. Pub. Nos.: 2010/0298257 and 2011/0251152:

(1) 2θ-reflections (°) at about: 5.0 and 7.3 (Form 1); and
(2) 2θ-reflections (°) at about: 6.1 and 12.7 (Form 6).

In one embodiment, the crystalline sofosbuvir has XRPD 2θ-reflections (°±0.2θ) at about:

(1) 7.5, 9.6, and 18.3; (Form 1A)
(2) 5.0, 7.3, and 18.1; (Form 1B)
(3) 6.9, 24.7, and 25.1; (Form 2)
(4) 19.7, 20.6, and 24.6; (Form 3)
(5) 5.0, 6.8, and 24.9; (Form 4)
(6) 5.2, 6.6, and 19.1; (Form 5) or
(7) 6.1, 20.1, and 20.8; (Form 6).

In certain embodiments, the crystalline sofosbuvir has XRPD 2θ-reflections (°±0.2θ) at about:

(1) 5.2, 7.5, 9.6, 16.7, 18.3, and 22.2 (Form 1);
(2) 5.0, 7.3, 9.4, and 18.1 (Form 1);
(3) 4.9, 6.9, 9.8, 19.8, 20.6, 24.7, 25.1, and 26.1 (Form 2);
(4) 6.9, 9.8, 19.7, 20.6, and 24.6 (Form 3);
(5) 5.0, 6.8, 19.9, 20.6, 20.9, and 24.9 (Form 4);
(6) 5.2, 6.6, 7.1, 15.7, 19.1, and 25.0 (Form 5); or
(7) 6.1, 8.2, 10.4, 12.7, 17.2, 17.7, 18.0, 18.8, 19.4, 19.8, 20.1, 20.8, 21.8, and 23.3 (Form 6).

In a further embodiment, crystalline sofosbuvir has XRPD 2θ-reflections (°±0.2θ) at about: 6.1, 8.2, 10.4, 12.7, 17.2, 17.7, 18.0, 18.8, 19.4, 19.8, 20.1, 20.8, 21.8, and 23.3. In yet a further embodiment, crystalline sofosbuvir has XRPD 2θ-reflections (°±0.2θ) at about: 6.1 and 12.7.

Sofosbuvir may be present in the pharmaceutical composition in a therapeutically effective amount. In some embodiments, the pharmaceutical compositions comprises from about 10% to about 70% w/w of sofosbuvir. In further embodiments, the composition comprises from about 15% to about 65% w/w, or from about 20% to about 60% w/w, or from about 25% to about 55% w/w, or from about 30% to about 50% w/w, or from about 35% to about 45% w/w of sofosbuvir. In further embodiments, the pharmaceutical composition comprises about 10% w/w, about 15% w/w, about 20% w/w, about 25% w/w, about 30% w/w, about 35% w/w, about 45% w/w, about 50% w/w, about 55% w/w, about 60% w/w, about 65% w/w, or about 70% w/w, or about 75% w/w. In a specific embodiment, the pharmaceutical composition comprises about 40% w/w of sofosbuvir.

C. Excipients

The pharmaceutical compositions provided in accordance with the present disclosure are usually administered orally. This disclosure therefore provides pharmaceutical compositions that comprise a solid dispersion comprising ledipasvir as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses by oral administration.

Administration may be via capsule, tablet, or the like. In one embodiment, the ledipasvir is in the form of a tablet. In a further embodiment, the tablet is a compressed tablet. In making the pharmaceutical compositions that include the solid described herein, the active ingredient is usually diluted by an excipient and/or enclosed within such a carrier that can be in the form of a capsule, tablet, sachet, paper or other container. When the excipient serves as a diluent, it can be in the form of a solid, semi-solid or liquid material (as above), which acts as a vehicle, carrier or medium for the active ingredient.

The pharmaceutical composition may be formulated for immediate release or sustained release. A "sustained release formulation" is a formulation which is designed to slowly release a therapeutic agent in the body over an extended period of time, whereas an "immediate release formulation" is an formulation which is designed to quickly release a therapeutic agent in the body over a shortened period of time. In some cases the immediate release formulation may be coated such that the therapeutic agent is only released once it reached the desired target in the body (e.g. the stomach). In a specific embodiment, the pharmaceutical composition is formulated for immediate release.

The pharmaceutical composition may further comprise pharmaceutical excipients such as diluents, binders, fillers, glidants, disintegrants, lubricants, solubilizers, and combinations thereof. Some examples of suitable excipients are described herein. When the pharmaceutical composition is formulated into a tablet, the tablet may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In one embodiment, the pharmaceutical composition comprises a diluent selected from the group consisting of dicalcium phosphate, cellulose, compressible sugars, dibasic calcium phosphate dehydrate, lactose, lactose monohydrate, mannitol, microcrystalline cellulose, starch, tribasic calcium phosphate, and combinations thereof.

In further embodiments, the pharmaceutical composition comprises lactose monohydrate in an amount from about 1 to about 50% w/w, or from about 1 to about 45% w/w, or from about 5 to about 40% w/w, or from about 5 to about 35% w/w, or from about 5 to about 25% w/w, or from about 10 to about 20% w/w. In specific embodiments, the lactose monohydrate is present at about 5% w/w, at about 10% w/w, at about 15% w/w, at about 20% w/w, at about 25% w/w, at about 30% w/w, at about 35% w/w, at about 40% w/w, at about 45% w/w, or at about 50% w/w. In a further specific embodiment, the lactose monohydrate is in an amount of about 16.5% w/w.

In yet further embodiments, the pharmaceutical composition comprises microcrystalline cellulose in an amount from about 1 to about 40% w/w, or from about 1 to about 35% w/w, or from about 1% to about 25% w/w, or from about 5 to about 25% w/w, or from about 10 to about 25% w/w, or from about 15 to about 20% w/w. In specific embodiments, the microcrystalline cellulose is present in an amount of about 5%, or about 10%, or about 15%, or about 20%, or about 25%, or about 30%, or about 35%, or about 40% w/w. In a further specific embodiment, the microcrystalline cellulose is in an amount of about 18% w/w.

In other embodiments, the pharmaceutical composition comprises a disintegrant selected from the group consisting of croscarmellose sodium, crospovidone, microcrystalline cellulose, modified corn starch, povidone, pregelatinized starch, sodium starch glycolate, and combinations thereof.

In certain embodiments, the pharmaceutical composition comprises croscarmellose sodium in an amount from about 1 to about 20% w/w, or from about 1 to about 15% w/w, or from about 1 to about 10% w/w, or from about 1 to about 8% w/w, or from about 2 to about 8% w/w. In specific embodiments, the croscarmellose sodium is present in an amount of about 1%, or about 3%, or about 6%, or about 8%, or about 10%, or about 13%, or about 15% w/w. In a further specific embodiment, the croscarmellose sodium is in an amount of about 5% w/w.

In other embodiments, the pharmaceutical composition comprises a glidant selected from the group consisting of colloidal silicon dioxide, talc, starch, starch derivatives, and combinations thereof.

In further embodiments, the pharmaceutical composition comprises colloidal silicon dioxide in an amount from about 0.1 to about 5% w/w, or from about 0.1 to about 4.5% w/w, or from about 0.1 to about 4% w/w, or from about 0.5 to about 5.0% w/w, or from about 0.5 to about 3% w/w, or from about 0.5 to about 2% w/w, or from about 0.5 to about 1.5% w/w. In specific embodiments, the colloidal silicon dioxide is present in an amount of about 0.1% w/w, 0.5% w/w, 0.75% w/w, 1.25% w/w, 1.5% w/w, or 2% w/w. In a further specific embodiment, the colloidal silicon dioxide is present in an amount of about 1% w/w.

In other embodiments, the pharmaceutical composition comprises a lubricant selected from the group consisting of calcium stearate, magnesium stearate, polyethylene glycol, sodium stearyl fumarate, stearic acid, talc, and combinations thereof.

In further embodiments, the pharmaceutical composition comprises magnesium stearate in an amount from about 0.1 to about 3% w/w, or from about 0.1 to about 2.5% w/w, or from about 0.5 to about 3% w/w, or from about 0.5 to about 2.5% w/w, or from about 0.5 to about 2% w/w, or from about 1 to about 3% w/w, or from about 1 to about 2% w/w. In specific embodiments, the magnesium stearate is present in an amount of about 0.1%, or about 0.5, or about 1%, or about 2%, or about 2.5%, or about 3% w/w. In a further specific embodiment, the magnesium stearate is in an amount of about 1.5% w/w.

In one embodiment, the pharmaceutical composition comprises a) about 30 to about 50% w/w of sofosbuvir and b) about 5 to about 35% w/w of the solid dispersion comprising ledipasvir. In a related embodiment, the composition comprises a) about 40% w/w of sofosbuvir and b) about 18% w/w of the solid dispersion comprising ledipasvir. In yet a further related embodiment, the composition further comprises a) about 5 to about 25% w/w lactose monohydrate, b) about 5 to about 25% w/w microcrystalline cellulose, c) about 1 to about 10% w/w croscarmellose sodium, d) about 0.5 to about 3% w/w colloidal silicon dioxide, and e) about 0.1 to about 3% w/w magnesium stearate. In a further embodiment, the pharmaceutical composition comprises a) about 40% w/w of sofosbuvir, b) about 18% w/w of the solid dispersion comprising ledipasvir, c) about 16.5% w/w lactose monohydrate, d) about 18% w/w microcrystalline cellulose, e) about 5% w/w croscarmellose sodium, f) about 1% w/w colloidal silicon dioxide, and g) about 1.5% w/w magnesium stearate.

3. Pharmaceutical Dosage Forms

The disclosure provides for tablets, pills, and the like, comprising the pharmaceutical compositions or dosage forms described herein. The tablets or pills of the present disclosure may be coated to provide a dosage form affording the advantage of prolonged action or to protect from the acid conditions of the stomach. The tablets may also be formulated for immediate release as previously described. In certain embodiments, the tablet comprises a film coating. A film coating is useful for limiting photolytic degradation. Suitable film coatings are selected by routine screening of commercially available preparations. In one embodiment, the film coating is a polyvinylalcohol-based coating.

The tablets may be formulated into a monolayer or bilayer tablet. Typically, monolayer tablet comprise the active ingredients (i.e., ledipasvir and sofosbuvir) co-mixed in a single uniform layer. For making monolayer tablets, exemplary methods include, but are not limited to coblend (or bi-granulation) and codry granulation. Coblend granulation is a multi-step process consisting of separate dry granulations for each active ingredient with excipients followed by the blending of the two granulations together. Codry granulation consisted of dry granulating both active ingredients and excipients together.

Bilayer tablets comprise the active ingredients (i.e., ledipasvir and sofosbuvir) in separate layers and can be made by making a blend comprising excipients and one active ingredient (i.e., ledipasvir), and making a separate blend comprising the second active ingredient (i.e., sofosbuvir) and excipients. One blend may then be precompressed, and the second blend may then be added on top of the first precompressed blends. The resulting tablet comprises two separate layers, each layer comprising a different active ingredient.

In one embodiment, the tablet comprises a) about 30 to about 50% w/w of sofosbuvir and b) about 10 to about 40% w/w of the solid dispersion comprising ledipasvir. In a related embodiment, the tablet comprises a) about 40% w/w of sofosbuvir and b) about 18% w/w of the solid dispersion comprising ledipasvir. In a further embodiment, the tablet comprises a) about 300 to about 500 mg of sofosbuvir and b) about 50 to about 130 mg of ledipasvir. In a yet further embodiment, the tablet comprises a) about 400 mg of sofosbuvir and b) about 90 mg of ledipasvir. In related embodiment, the tablet further comprises a) about 5 to about 25% w/w lactose monohydrate, b) about 5 to about 25% w/w microcrystalline cellulose, c) about 1 to about 10% w/w croscarmellose sodium, d) about 0.5 to about 3% w/w colloidal silicon dioxide, and e) about 0.1 to about 3% w/w magnesium stearate.

In some embodiments, the pharmaceutical compositions as described herein are formulated in a unit dosage or pharmaceutical dosage form. The term "unit dosage forms" or "pharmaceutical dosage forms" refers to physically discrete units suitable as unitary dosages for human patients and other mammals, each unit containing a predetermined quantity of active material calculated to produce the desired therapeutic effect, in association with a suitable pharmaceutical excipient (e.g., a tablet or capsule). The compounds are generally administered in a pharmaceutically effective amount. In some embodiments, each dosage unit contains from 3 mg to 2 g of ledipasvir. In other embodiments, the pharmaceutical dosage form comprises from about 3 to about 360 mg, or about 10 to about 200 mg, or about 10 to about 50 mg, or about 20 to about 40 mg, or about 25 to about 35 mg, or about 40 to about 140 mg, or about 50 to about 130 mg, or about 60 to about 120 mg, or about 70 to about 110 mg, or about 80 to about 100 mg. In specific embodiments, the pharmaceutical dosage form comprises about 40, or about 45, or about 50, or about 55, or about 60, or about 70, or about 80, or about 100, or about 120, or about 140, or about 160, or about 180, or about 200, or about 220 mg of ledipasvir. In a further specific embodiment, the pharmaceutical dosage form comprises about 90 mg of ledipasvir. In yet a further specific embodiment, the pharmaceutical dosage form comprises about 30 mg of ledipasvir.

In other embodiments, the pharmaceutical dosage form comprises from about 1 mg to about 3 g of sofosbuvir. In other embodiments, the pharmaceutical dosage form comprises from about 1 to about 800 mg, or about 100 to about 700 mg, or about 200 to about 600 mg, or about 300 to about 500 mg, or about 350 to about 450 mg, of sofosbuvir. In specific embodiments, the pharmaceutical dosage form comprises about 50, or about 100, or about 150, or about 200, or about 250, or about 300, or about 350, or about 450, or about 500, or about 550, or about 600, or about 650, or about 700, or about 750, or about 800 mg of sofosbuvir. In a further specific embodiment, the pharmaceutical dosage form comprises about 400 mg of sofosbuvir. It will be understood, however, that the amount of ledipasvir and/or sofosbuvir actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

In a specific embodiment, the pharmaceutical dosage form comprises about 400 mg of sofosbuvir and about 90 mg of ledipasvir.

In one embodiment, the pharmaceutical composition, or alternatively, the pharmaceutical dosage form or tablet comprises about 90 mg of amorphous ledipasvir formulated in a solid dispersion comprising a polymer:ledipasvir ratio of 1:1, about 400 mg crystalline sofosbuvir, lactose monohydrate in an amount from about 5 to about 25% w/w, microcrystalline cellulose in an amount from about 5 to about 25% w/w, croscarmellose sodium in an amount from about 1 to about 10% w/w, colloidal silicon dioxide in an amount from about 0.5 to about 3% w/w, and magnesium stearate in an amount from about 0.1 to about 3% w/w. In one embodiment, the polymer is copovidone.

In further embodiments, the pharmaceutical composition, pharmaceutical dosage form, or tablet as described herein is free of negative drug-drug interactions. In a related embodiment, the pharmaceutical composition, pharmaceutical dosage form, or tablet is free of negative drug-drug interactions with acid suppressive therapies. In a further embodiment, the pharmaceutical composition, pharmaceutical dosage form, or tablet as described herein is administrable without regard to food and with or without regard to the patient being on an acid-suppressive therapy.

4. Methods of Use

The solid dispersions, pharmaceutical compositions, pharmaceutical dosage forms, and tablets of ledipasvir and sofosbuvir as described herein are administered to a patient suffering from hepatitis C virus (HCV) in a daily dose by oral administration. In one embodiment, the patient is human.

Previously, ledipasvir had been demonstrated to have a negative food effect when administered alone. Unexpectedly, the combination treatment of ledipasvir and sofosbuvir does not exhibit a negative food effect. Accordingly, the administration of the pharmaceutical composition comprising sofosbuvir and ledipasvir can be taken without regard to food.

In some embodiments, the combination composition achieved a reduced food effect. In some aspects, the composition achieves a first exposure, when administered to a patient following a meal, that is no more than 25%, or alternatively not more than 20%, 15% or 10%, lower than a second exposure when administered to the patient not following a meal. The exposures can be measured as $C_{max}$, $AUC_{last}$ or $AUC_{inf}$. In some aspects, the administration is carried out within four, three, two or one hours following the meal.

In one embodiment, the solid dispersions, pharmaceutical compositions, pharmaceutical dosage forms, and tablets of ledipasvir and sofosbuvir as described herein are effective in treating one or more of genotype 1 HCV infected patients, genotype 2 HCV infected patients, genotype 3 HCV infected patients, genotype 4 HCV infected patients, genotype 5 HCV infected patients, and/or genotype 6 HCV infected patients. In one embodiment, the solid dispersions, pharmaceutical compositions, pharmaceutical dosage forms, and tablets of ledipasvir and sofosbuvir as described herein are effective in treating genotype 1 HCV infected patients, including genotype 1a and/or genotype 1b. In another embodiment, the solid dispersions, pharmaceutical compositions, pharmaceutical dosage forms, and tablets of ledipasvir and sofosbuvir as described herein are effective in treating genotype 2 HCV infected patients, including genotype 2a, genotype 2b, genotype 2c and/or genotype 2d. In another embodiment, the solid dispersions, pharmaceutical compositions, pharmaceutical dosage forms, and tablets of ledipasvir and sofosbuvir as described herein are effective in treating genotype 3 HCV infected patients, including genotype 3a, genotype 3b, genotype 3c, genotype 3d, genotype 3e and/or genotype 3f. In another embodiment, the solid dispersions, pharmaceutical compositions, pharmaceutical dosage forms, and tablets of ledipasvir and sofosbuvir as described herein are effective in treating genotype 4 HCV infected patients, including genotype 4a, genotype 4b, genotype 4c, genotype 4d, genotype 4e, genotype 4f, genotype 4g, genotype 4h, genotype 4i and/or genotype 4j. In another embodiment, the solid dispersions, pharmaceutical compositions, pharmaceutical dosage forms, and tablets of ledipasvir and sofosbuvir as described herein are effective in treating genotype 5 HCV infected patients, including genotype 5a. In another embodiment, the solid dispersions, pharmaceutical compositions, pharmaceutical dosage forms, and tablets of ledipasvir and sofosbuvir as described herein are effective in treating genotype 6 HCV infected patients, including genotype 6a. In one embodiment, the compositions are pangenotypic, meaning they are useful across all genotypes and drug resistant mutants thereof.

In some embodiments, the pharmaceutical composition, pharmaceutical dosage form, or tablet of ledipasvir and sofosbuvir as described herein is administered, either alone or in combination with one or more therapeutic agent(s) for treating HCV (such as a HCV NS3 protease inhibitor or an inhibitor of HCV NS5B polymerase), for about 24 weeks, for about 16 weeks, or for about 12 weeks, or less. In further embodiments, the pharmaceutical composition, pharmaceutical dosage form, or tablet of ledipasvir and sofosbuvir is administered, either alone or in combination with one or more therapeutic agent(s) for treating HCV (such as a HCV NS3 protease inhibitor or an inhibitor of HCV NS5B polymerase), for about 24 weeks or less, about 22 weeks or less, about 20 weeks or less, about 18 weeks or less, about 16 weeks or less, about 12 weeks or less, about 10 weeks or less, about 8 weeks or less, or about 6 weeks or less or about 4 weeks or less. The pharmaceutical composition, pharmaceutical dosage form, or tablet may be administered once daily, twice daily, once every other day, two times a week, three times a week, four times a week, or five times a week.

In further embodiments, a sustained virologic response is achieved at about 4 weeks, 6 weeks, 8 weeks, 12 weeks, or 16 weeks, or at about 20 weeks, or at about 24 weeks, or at about 4 months, or at about 5 months, or at about 6 months, or at about 1 year, or at about 2 years.

In one embodiment, the daily dose is 90 mg of ledipasvir and 400 mg of sofosbuvir administered in the form of a tablet. In a further embodiment, the daily dose is a tablet comprising a) about 30 to about 50% w/w of sofosbuvir, b) about 10 to about 40% w/w of the solid dispersion comprising ledipasvir, c) about 5 to about 25% w/w lactose monohydrate, d) about 5 to about 25% w/w microcrystalline cellulose, e) about 1 to about 10% w/w croscarmellose sodium, f) about 0.5 to about 3% w/w colloidal silicon dioxide, and g) about 0.1 to about 3% w/w magnesium stearate.

In further embodiments, the patient is also suffering from cirrhosis. In yet a further embodiment, the patient is not suffering from cirrhosis.

5. Combination Therapy

In the methods described herein, the method can further comprise the administration of another therapeutic agent for treating HCV and other conditions such as HIV infections. In one embodiment, non-limiting examples of suitable additional therapeutic agents include one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs or therapeutic agents for treating HCV.

More specifically, the additional therapeutic agent may be selected from the group consisting of:

1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), and belerofon;

2) ribavirin and its analogs, e.g., ribavirin (Rebetol, Copegus), and taribavirin (Viramidine);

3) HCV NS3 protease inhibitors, e.g., boceprevir (SCH-503034, SCH-7), telaprevir (VX-950), TMC435350, BI-1335, BI-1230, MK-7009, VBY-376, VX-500, GS-9256, GS-9451, BMS-605339, PHX-1766, AS-101, YH-5258, YH5530, YH5531, ABT-450, ACH-1625, ITMN-191, MK5172, MK6325, and MK2748;

4) alpha-glucosidase 1 inhibitors, e.g., celgosivir (MX-3253), Miglitol, and UT-231B;

5) hepatoprotectants, e.g., emericasan (IDN-6556), ME-3738, GS-9450 (LB-84451), silibilin, and MitoQ;

6) nucleoside or nucleotide inhibitors of HCV NS5B polymerase, e.g., R1626, R7128 (R4048), IDX184, IDX-102, BCX-4678, valopicitabine (NM-283), MK-0608, and INX-189 (now BMS986094);

7) non-nucleoside inhibitors of HCV NS5B polymerase, e.g., PF-868554, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, ABT-072, ABT-333, GS-9669, PSI-7792, and GS-9190;

8) HCV NS5A inhibitors, e.g., AZD-2836 (A-831), BMS-790052, ACH-3102, ACH-2928, MK8325, MK4882, MK8742, PSI-461, IDX719, ABT-267, and A-689;

9) TLR-7 agonists, e.g., imiquimod, 852A, GS-9524, ANA-773, ANA-975, AZD-8848 (DSP-3025), and SM-360320;

10) cyclophillin inhibitors, e.g., DEBIO-025, SCY-635, and NIM811;

11) HCV IRES inhibitors, e.g., MCI-067;

12) pharmacokinetic enhancers, e.g., BAS-100, SPI-452, PF-4194477, TMC-41629, GS-9350, GS-9585, and roxythromycin; and 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, and VX-497 (merimepodib).

More specifically, the additional therapeutic agent may be combined with one or more compounds selected from the group consisting of non-nucleoside inhibitors of HCV NS5B polymerase (ABT-072 and ABT-333), HCV NS5A inhibitors (ACH-3102 and ACH-2928) and HCV NS3 protease inhibitors(ABT-450 and ACH-125).

In another embodiment, the therapeutic agent used in combination with the pharmaceutical compositions as described herein can be any agent having a therapeutic effect when used in combination with the pharmaceutical compositions as described herein. For example, the therapeutic agent used in combination with the pharmaceutical compositions as described herein can be interferons, ribavirin analogs, NS3 protease inhibitors, NS5B polymerase inhibitors, alpha-glucosidase 1 inhibitors, hepatoprotectants, non-nucleoside inhibitors of HCV, and other drugs for treating HCV.

In another embodiment, the additional therapeutic agent used in combination with the pharmaceutical compositions as described herein is a cyclophillin inhibitor, including for example, a cyclophilin inhibitor disclosed in WO2013/185093. Non-limiting examples include one or more compounds selected from the group consisting of:

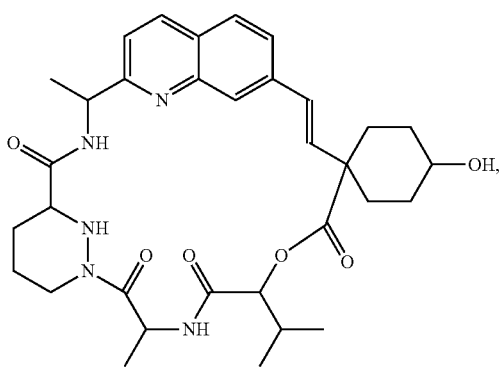

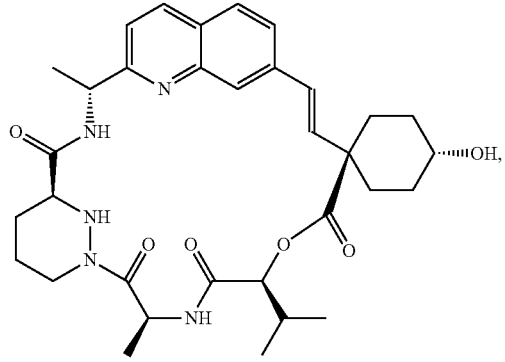

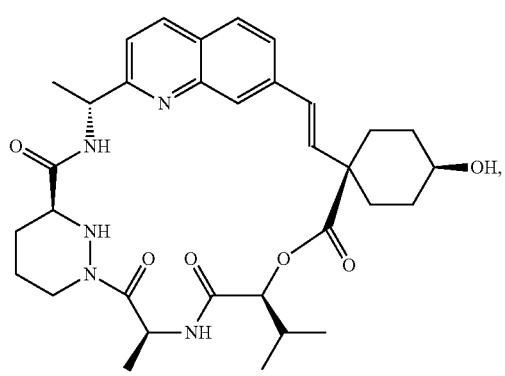

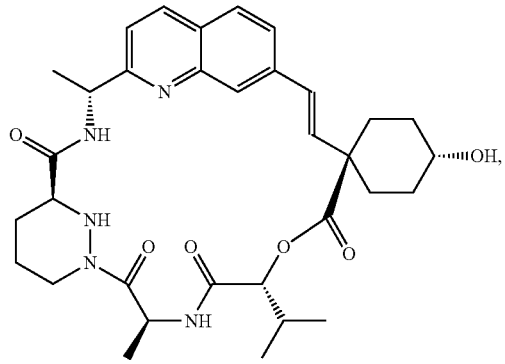

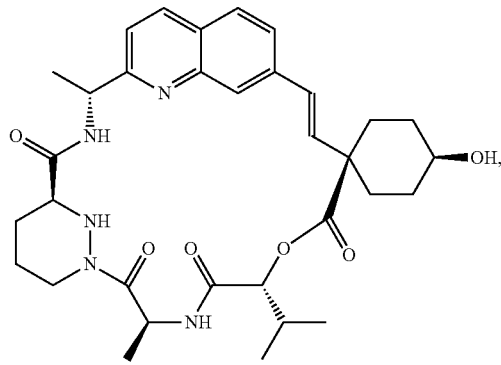

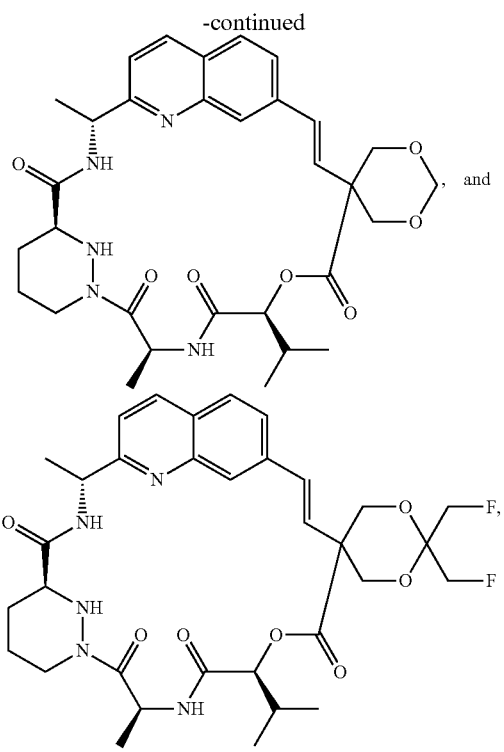

and stereoisomers and mixtures of stereoisomers thereof.

In another embodiment, the additional therapeutic agent used in combination with the pharmaceutical compositions as described herein is a non-nucleoside inhibitor of HCV NS5B polymerase. A non-limiting example includes Compound E (as described below).

Examples of additional anti-HCV agents which can be combined with the compositions provided herein include, without limitation, the following:

A. interferons, for example, pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), or belerofon, IFN alpha-2b XL, rIFN-alpha 2a, consensus IFN alpha, infergen, rebif, pegylated IFN-beta, oral interferon alpha, feron, reaferon, intermax alpha, r-IFN-beta, and infergen+actimmuneribavirin and ribavirin analogs, e.g., rebetol, copegus, VX-497, and viramidine (taribavirin);

B. NS5A inhibitors, for example, Compound B (described below), Compound C (described below), ABT-267, Compound D (described below), JNJ-47910382, daclatasvir (BMS-790052), ABT-267, MK-8742, EDP-239, IDX-719, PPI-668, GSK-2336805, ACH-3102, A-831, A-689, AZD-2836 (A-831), AZD-7295 (A-689), and BMS-790052;

C. NS5B polymerase inhibitors, for example, Compound E (described below), Compound F (described below), ABT-333, Compound G (described below), ABT-072, Compound H (described below), tegobuvir (GS-9190), GS-9669, TMC647055, setrobuvir (ANA-598), filibuvir (PF-868554), VX-222, IDX-375, IDX-184, IDX-102, BI-207127, valopicitabine (NM-283), PSI-6130 (R1656), PSI-7851, BCX-4678, nesbuvir (HCV-796), BILB 1941, MK-0608, NM-107, R7128, VCH-759, GSK625433, XTL-2125, VCH-916, JTK-652, MK-3281, VBY-708, A848837, GL59728, A-63890, A-48773, A-48547, BC-2329, BMS-791325, and BILB-1941;

D. NS3 protease inhibitors, for example, Compound I, Compound J, Compound K, ABT-450, Compound L (described below), simeprevir (TMC-435), boceprevir (SCH-503034), narlaprevir (SCH-900518), vaniprevir (MK-7009), MK-5172, danoprevir (ITMN-191), sovaprevir (ACH-1625), neceprevir (ACH-2684), Telaprevir (VX-950), VX-813, VX-500, faldaprevir (BI-201335), asunaprevir (BMS-650032), BMS-605339, VBY-376, PHX-1766, YH5531, BILN-2065, and BILN-2061;

E. alpha-glucosidase 1 inhibitors, for example, celgosivir (MX-3253), Miglitol, and UT-231B;

F. hepatoprotectants, e.g., IDN-6556, ME 3738, MitoQ, and LB-84451;

G. non-nucleoside inhibitors of HCV, e.g., benzimidazole derivatives, benzo-1,2,4-thiadiazine derivatives, and phenylalanine derivatives; and H. other anti-HCV agents, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811.

Compound B is an NS5A inhibitor and is represented by the following chemical structure:

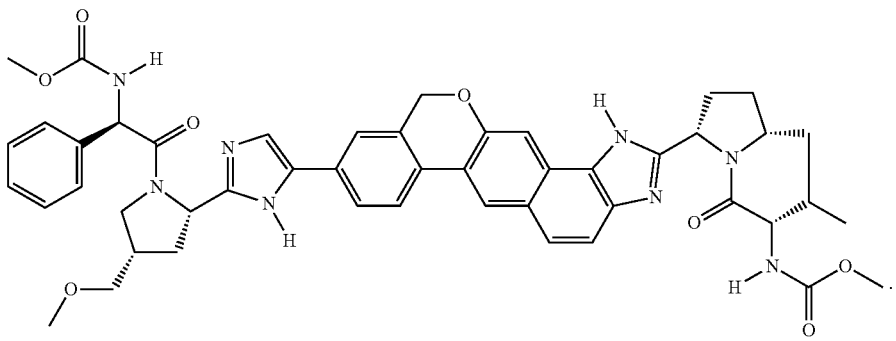

Compound C is an NS5A inhibitor and is represented by the following chemical structure:

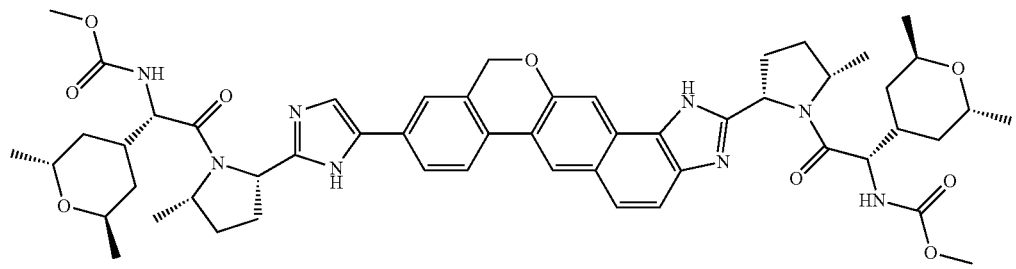

Compound D is an NS5A inhibitor and is represented by the following chemical structure:

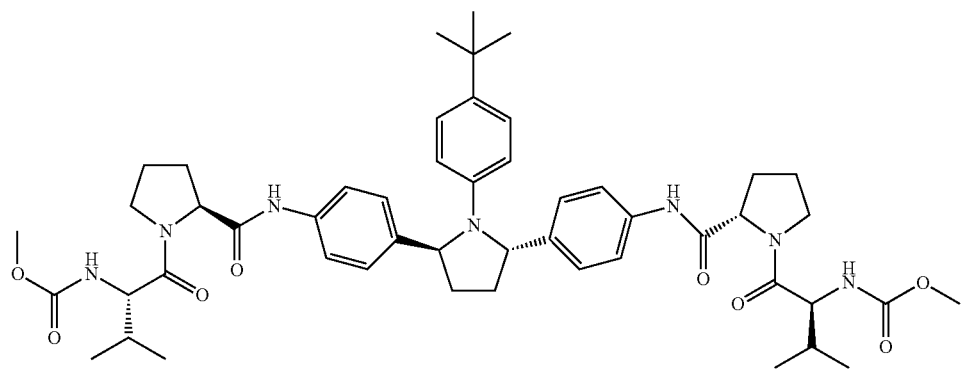

See U.S. Publication No. 2013/0102525 and references cited therein.

Compound E is an NS5B Thumb II polymerase inhibitor and is represented by the following chemical structure:

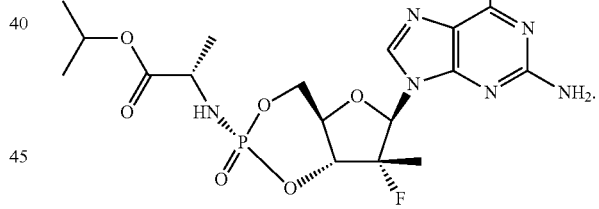

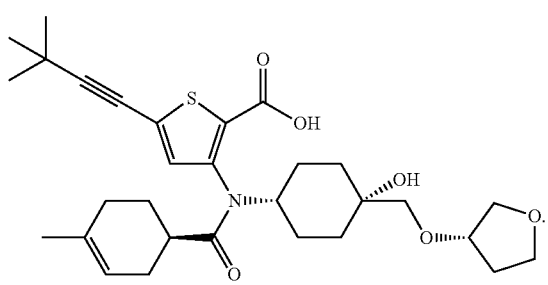 [SMILES: CC1=CC[C@H](C(=O)N(c2cc(C#CC(C)(C)C)sc2C(=O)O)[C@H]2CC[C@](O)(CO[C@H]3CCOC3)CC2)CC1]

Compound F is a nucleotide inhibitor prodrug designed to inhibit replication of viral RNA by the HCV NS5B polymerase, and is represented by the following chemical structure:

Compound G is an HCV polymerase inhibitor and is represented by the following structure:

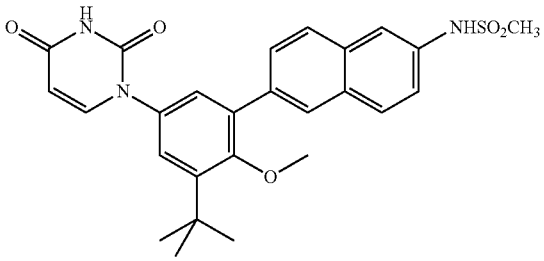

See U.S. Publication No. 2013/0102525 and references therein.

Compound H is an HCV polymerase inhibitor and is represented by the following structure:

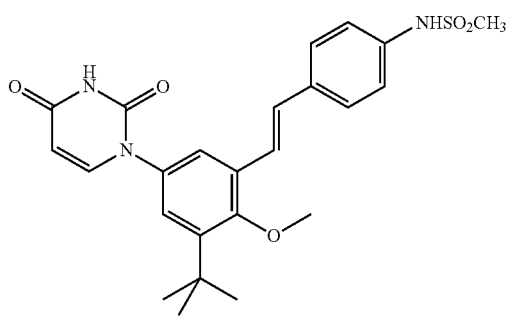

See U.S. Publication No. 2013/0102525 and references therein.

Compound I is an HCV protease inhibitor and is represented by the following chemical structure:

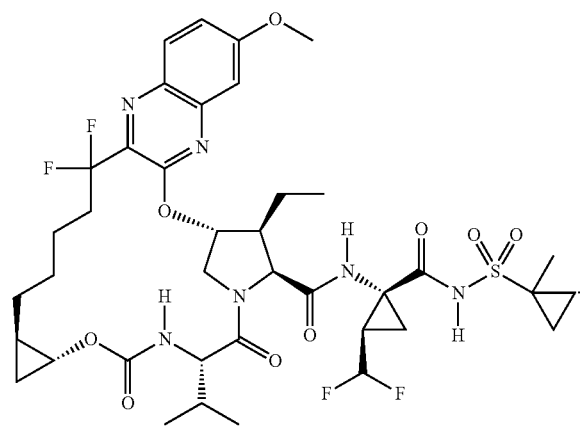 [SMILES: CC[C@@H]1[C@@H]2CN(C(=O)[C@H](C(C)C)NC(=O)O[C@@H]3C[C@H]3CCCCC(F)(F)c3nc4ccc(OC)cc4nc3O2)[C@@H]1C(=O)N[C@]1(C(=O)NS(=O)(=O)C2(C)CC2)C[C@H]1C(F)F]

See U.S. Publication No. 2014/0017198 and references therein.

Compound J is an HCV protease inhibitor and is represented by the following chemical structure:

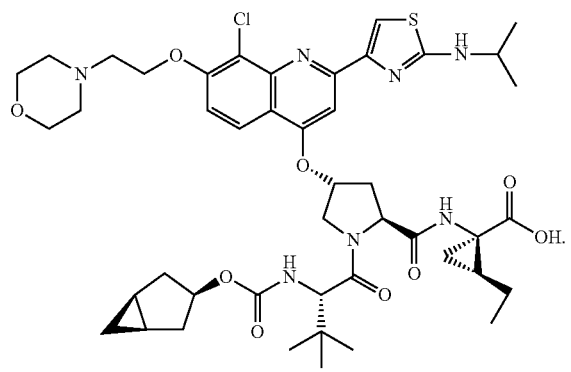

See U.S. Pat. No. 8,178,491 and references therein.

Compound K is an HCV protease inhibitor and is represented by the following chemical structure:

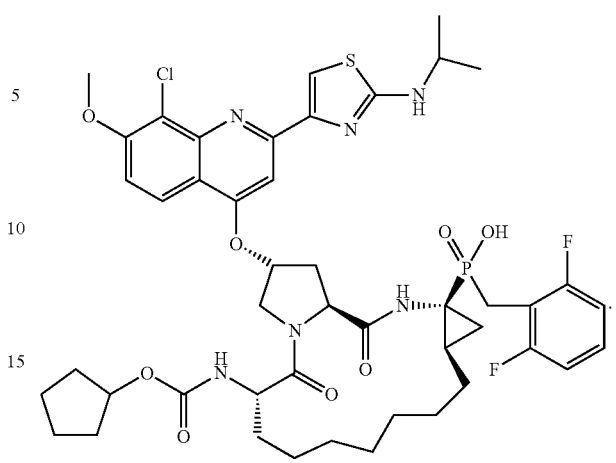

Compound L is an HCV protease inhibitor and is represented by the following chemical structure:

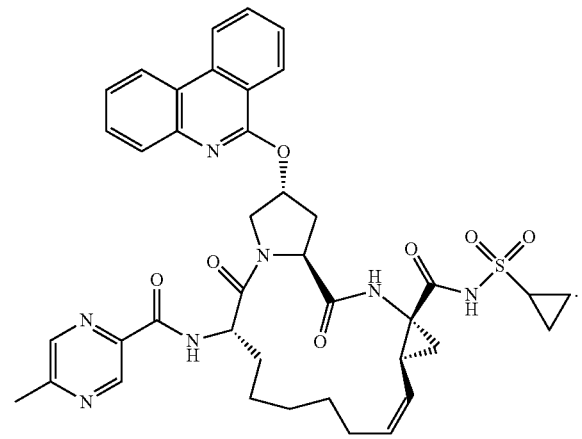 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccccc45)CN3C2=O)cn1]

See U.S. Publication No. 2013/0102525 and references therein.

In one embodiment, the additional therapeutic agent used in combination with the pharmaceutical compositions as described herein is a HCV NS3 protease inhibitor. Non-limiting examples include one or more compounds selected from the group consisting of:

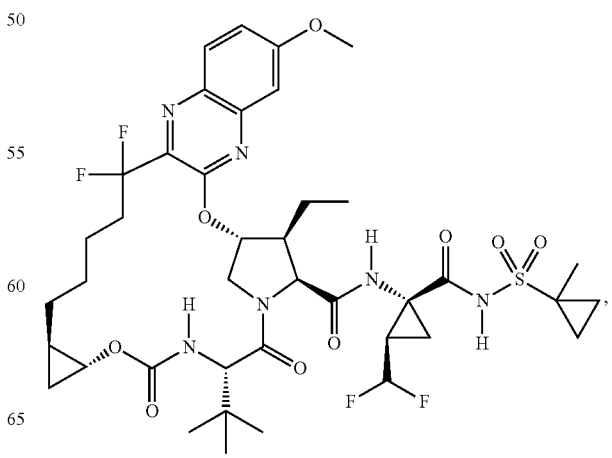

-continued

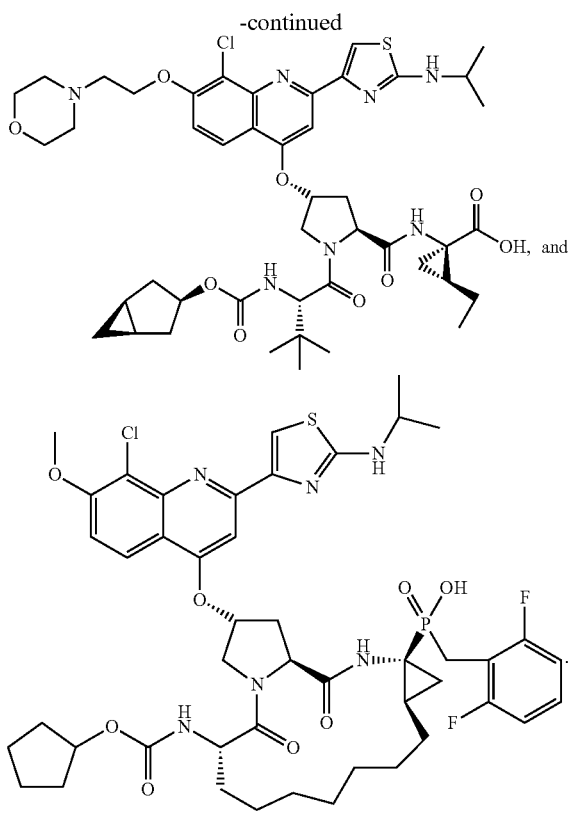

In another embodiment, the present application is provided a method of treating hepatitis C in a human patient in need thereof comprising administering to the patient a therapeutically effective amount of a pharmaceutical composition as described herein and an additional therapeutic selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, levovirin, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811 and a pharmaceutically acceptable carrier or excipient.

In yet another embodiment, the present application provides a combination pharmaceutical agent comprising:

a) a first pharmaceutical composition comprising an effective amount of wherein ledipasvir is substantially amorphous; and an effective amount of sofosbuvir wherein sofosbuvir is substantially crystalline as described herein and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

The additional therapeutic agent may be one that treats other conditions such as HIV infections. Accordingly, the additional therapeutic agent may be a compound useful in treating HIV, for example HIV protease inhibiting compounds, non-nucleoside inhibitors of HIV reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, the additional therapeutic agent may be selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, levovirin, VX-497, and viramidine (taribavirin)

13) NS5a inhibitors, e.g., A-831, A-689, and BMS-790052,

14) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating Hepatitis C, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 20) pharmacokinetic enhancers, e.g., BAS-100 and SPI452, 20) RNAse H inhibitors, e.g., ODN-93 and ODN-112, and 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

In one embodiment, the additional therapeutic agent is ribavirin. Accordingly, methods described herein include a method of treating hepatitis C in a human patient in need thereof comprising administering to the patient a therapeutically effective amount of ribavirin and a therapeutically effective amount of a pharmaceutical composition, pharmaceutical dosage form, or tablet as described herein. In a further embodiment, the ribavirin and pharmaceutical composition, pharmaceutical dosage form, or tablet comprising sofosbuvir and ledipasvir is administered for about 12 weeks or less. In further embodiments, the ribavirin and pharmaceutical composition, pharmaceutical dosage form, or tablet comprising sofosbuvir and ledipasvir is administered for about 8 weeks or less, for about 6 weeks or less, or for about 4 weeks or less.

It is contemplated that the additional therapeutic agent will be administered in a manner that is known in the art and the dosage may be selected by someone of skill in the art. For example, the additional agent may be administered in a dose from about 0.01 milligrams to about 2 grams per day.

EXAMPLES

In the following examples and throughout this disclosure, abbreviations as used herein have respective meanings as follows:

| | |
|---|---|
| ACN | Acetonitrile |
| AE | Adverse Event |
| API | Active Pharmaceutical Ingredient |
| AUC | Area Under the Curve |
| $AUC_{inf}$ | Area under the concentration versus time curve extrapolated to infinite time, calculated as AUC0-last + (Clast/λz) |
| $AUC_{last}$ | Area under the concentration versus time curve from time zero to the last quantifiable concentration |
| BMI | Body Mass Indec |
| BT | Breakthrough Rate |
| CI | Confidence Interval |
| CL/F | Apparent oral clearance after administration of the drug: CL/F = Dose/AUC |
| $C_{last}$ | Last observed quantifiable concentration of the drug |
| cm | Centimeter |
| $C_{max}$ | Maximum Concentration |
| cP | Centipoise |
| cP | Centipoise |
| CV | Coefficient of Variation |
| $D_{90}$ | Particle Size |
| DCF | Drug Content Factor |
| DCF | Drug Content Factor |
| DCM | Dichloromethane |
| dL | Deciliter |
| DRM | Drug Related Material |
| DSC | Differential Scanning Calorimetry |
| $E_{max}$ | Maximum Effect |
| F % | Percent Bioavailability |
| FaSSIF | Fasted State Simulated Intestinal Fluids |
| FB | Free Base |
| FDC | Fixed-Dose Combination |
| FeSSIF | Fed State Simulated Intestinal Fluid |
| FT | Fourier Transform |
| g | Gram |
| GLSM | Geometric Least Squares Mean |
| GMR | Geometric Mean Ratio |
| GT | Genotype |
| h or hr | Hour |
| HCV | Hepatitis C virus |
| HDPE | High Density Polyethylene |
| HPC | Hydroxypropylcellulose |
| HPLC | High-performance Liquid Chromatography |
| HPMC | Hydroxymethylcellulose |
| ICH | International Conference on Harmonisation; Impurities guidelines |
| IFN | Interferon |
| IU | International Unit |
| KF | Karl Fischer |
| kg | Kilogram |
| L | Liter |
| LCT | Long Chain Triglycerides |
| LDV | Compound I, GS-5885, Ledipasvir |
| LLOD | Lower limit of detection |
| LLOQ | Lower Limit of Quantification |
| LOD | Limit of Detection |
| M | Molar |
| mg | Milligram |
| min | Minute |
| mL | Milliliter |
| mm | Millimeter |
| mM | Millimolar |
| N | Population Size |
| n | Number of Patients |
| ng | Nanogram |
| nM | Nanomolar |
| nm | Nanometer |
| ° C. | Degrees Celsius |
| PD | Pharmacodynamic(s) |
| PEG or PG | Polyethylene Glycol |
| P-gp or Pgp | P-glycoprotein |
| PI | Protease-Inhibitor |
| PK | Pharmacokinetic |
| PLS | Partial Least Squares |
| PPI | Proton-Pump Inhibitors |
| PS | Particle Size |
| PVP | Povidone |
| PVP/VA | Copovidone |
| QS | Quantum Satis |

| | -continued |
|---|---|
| RAV | Resistance Associated Variants |
| RBV | Ribavirin |
| RH | Relative Humidity |
| RNA | Ribonucleic Acid |
| RSD | Relative Standard Deviation |
| RT | Room Temperature |
| $S_0$ | Intrinsic Solubility |
| SAE | Serious Adverse Event |
| SCT | Short Chain Triglycerides |
| SIBLM | Simulated Intestinal Bile Salt and Lecithin Mixture |
| SIF | Simulated Intestinal Fluids |
| SLS | Sodium Lauryl Sulfate |
| SOF | Sofosbuvir (GS-7977, formerly PSI-7977) |
| SS-NMR | Solid State Nuclear Magnetic Resonance |
| SVR | Sustained Virologic Response |
| t | Time |
| $t_{1/2}$ | Half-life (h) |
| TFA | Trifluoroacetic acid |
| $T_{max}$ | Time (observed time point) of $C_{max}$ |
| UPLC | Ultra Performance Liquid Chromatography |
| Upper Resp Tract Infx | Upper Respiratory Tract Infection |
| USP | Uniform Standards and Procedures |
| UV | Ultraviolet |
| VL | Viral Load |
| vRVR | Very Rapid Viral Response |
| $V_z/F$ | Apparent volume of distribution |
| wt or w | Weight |
| XRPD | Xray Powder Diffraction |
| μg | Microgram |
| μL | Microliter |
| μm | Micrometer |

Example 1

Synthesis of Amorphous Ledipasvir

Methods for making various forms of ledipasvir may be found in U.S. Publication Nos. 2013/0324740, and 2013/0324496. Both of these applications are incorporated herein by reference. Following is a method for isolating amorphous free base of ledipasvir.

Combine ledipasvir acetone solvate (191.4 g) and acetonitrile (1356 g) in a reaction vessel and mix contents until a solution is achieved. Add this ledipasvir in acetonitrile solution slowly to another reaction vessel containing vigorously agitated water (7870 g). Agitate contents at about 23° C. for about 30 minutes. Filter the contents and dry at about 40-45° C. until constant weight is achieved to afford ledipasvir amorphous solid (146.4 g, 82% yield).

Example 2

Tablet Preparation and Formulation

A. Dose Selection of Tablets
i. Sofosbuvir

The sofosbuvir dose selected for the tablet formulation is 400 mg once daily. Support for the 400 mg sofosbuvir dose can be derived from $E_{max}$ PK/PD modeling with early virological and human exposure data which also supports the selection of a 400 mg sofosbuvir dose over others tested.

The mean sofosbuvir major metabolite $AUC_{tau}$ for the 400 mg sofosbuvir dose is associated with approximately 77% of the maximal HCV RNA change from baseline achievable as determined by this model, a value which is on the cusp of the plateau of the exposure-response sigmoidal curve. In a sigmoidal $E_{max}$ model, there is a relatively linear exposure-response relationship in the 20 to 80% maximal effect range. Therefore, given that sofosbuvir exposure with 200 mg tablets appears dose-proportional with single doses up to 1200 mg, doses below 400 mg are expected to yield considerable reductions in the magnitude of HCV RNA change from baseline. Similarly, in order to improve upon an efficacy prediction of 77% in the plateau of the exposure-response curve, substantial increases in exposure (and hence dose) would be needed for an appreciable increase in antiviral effect.

The sofosbuvir dose of 400 mg once daily was associated with higher SVR rates in genotype 1 HCV infected patients as compared to the 200 mg once daily dose when given in conjunction with additional HCV therapeutics for 24 weeks. Safety and tolerability appeared similar across both dose levels. In addition, when sofosbuvir 400 mg once daily plus other HCV therapeutics were given to genotype 2 or 3 HCV infected patients, 100% SVR24 was observed.

ii. Ledipasvir

The maximum median HCV RNA log 10 reduction was 3 or greater for all cohorts dosed with ≥3 mg of ledipasvir. An $E_{max}$ PK/PD model indicates that the exposures achieved following administration of the 30 mg dose provides >95% of maximal antiviral response in genotype 1a HCV infected patients. It was also observed that 30 mg or greater of ledipasvir likely provided coverage of some drug related mutations that doses less than 30 mg did not, based on an analysis of NS5A mutants that arose in response to exposure to ledipasvir. Therefore, 30 mg and 90 mg of ledipasvir were selected as the dose for the formulations described herein.

Further studies suggest that, when ledipasvir is administered in combination with other therapeutic agents, the breakthrough (BT) rate (number of patients with HCV RNA>lower limit of quantification (LLOQ) after having achieved vRVR/total number of patients who achieved vRVR), is higher with doses of 30 mg (BT=33%, 11/33; 30 mg ledipasvir), than with doses of 90 mg (BT=12%, 9/74; 90 mg ledipasvir). Therefore, the 90 mg dose of ledipasvir may confer a greater antiviral coverage that prevents viral breakthrough.

B. Solid Dispersion Comprising Ledipasvir

To make the tablets comprising the combination of sofosbuvir and ledipasvir as described herein, a solid dispersion comprising ledipasvir was co-formulated with crystalline sofosbuvir. The starting material of the solid dispersion can be a variety of forms of ledipasvir including crystalline forms, amorphous form, salts thereof, solvates and free base, as described herein. Because of the high solubility in organic solvents and excipients and the ability to isolate the ledipasvir free base crystalline acetone solvate, this form was used in the amorphous solid dispersion of ledipasvir.

The spray dried solid dispersion approach achieved the most desirable characteristics relative to the other formulation approaches, which included improved in vivo and in vitro performance and manufacturability/scalability.

The spray dry feed solution was prepared by solubilizing ledipasvir acetone solvate and polymer in the feed solvent. Aggressive mixing or homogenization was used to avoid clumping of the composition.

Different polymers were tested for preferred characteristics in the solid dispersions. Non-ionic polymers such as hypromellose and copovidone solid dispersions both showed adequate stability and physical characteristics.

The feed solution was initially evaluated for appropriate solvent with regard to solubility, stability, and viscosity. Ethanol, methanol, and dichloromethane (DCM) all demonstrated excellent solubility (ledipasvir solubility>500 mg/mL). Ethanolic and DCM-based feed stocks were assessed for preparation ease and spray dried at a range of inlet and outlet temperatures to assess the robustness of the spray dry process. Both solvents gave rapid dissolution of ledipasvir and copovidone.

Spray drying out of ethanol resulted in high yields (88, 90, 92, 94, 95, 97, 98, 99%) across a wide range of spray-drying outlet temperatures (49-70° C.) with no material accumulation on the spray dry chamber. Spray drying out of DCM resulted in yields of 60%, 78%, and 44%. Overall, the ledipasvir Solid Dispersion (50% w/w) in a ledipasvir to copovidone ratio of 1:1 demonstrated good chemical stability in the ethanolic feed solution.

An ethanolic solution of 10% ledipasvir acetone solvate and 10% copovidone was prepared using homogenization. Viscosity of ethanolic solutions of ledipasvir:copovidone were low, measured through 30% solids content (~65 cP).

Spray drying was conducted using two fluid nozzle or a hydrolytic pressure nozzle. Table 1 presents the spray dry process parameters evaluated at 100 g-4000 g of total feed solution using the Anhydro MS35 spray dryer and Table 2 shows the spray dry process parameters using the hydrolytic pressure nozzle. Particle size data suggested sufficiently large particle size (10-14 μm mean PS) and was minimally affected by using higher spray rates or a larger diameter spray nozzle. Nozzle gas flow was not modulated to increase particle size.

TABLE 1

Ledipasvir Spray Dry Parameters on Anhydro MS35 Spray Dryer Using a Two Fluid Nozzle

| Parameter | Trial 1 | Trial 2 | Trial 3 | Trial 4 |
|---|---|---|---|---|
| Batch Size (g) | 100 | 250 | 250 | 4000 |
| Solids % | 20 | 20 | 20 | 20 |
| Feed Rate (mL/min) | 30 | 40 | 40 | 40 |
| Spray Nozzle (mm) | 1.0 | 1.0 | 1.2 | 1.2 |
| Nozzle Gas Flow (kg/hr) | 6.0 | 6.0 | 6.0 | 6.0 |
| Chamber Gas Flow (kg/hr) | 35.0 | 35.0 | 35.0 | 35.0 |
| Inlet Temp (° C.) | 125 | 165 | 165 | 165 |
| Outlet Temp (° C.) | 70 | 73 | 72 | 76 |
| PS $d_{10}/d_{50}/d_{90}$/mean (μm) | 4/9/18/10 | 5/10/20/12 | 5/10/19/11 | 6/12/22/14 |
| Post Spray LOD (%) | 5.56 | 4.86 | 4.29 | 3.42 |

TABLE 2

Example of Ledipasvir Spray Dry Parameters Using a Hydrolyic Pressure Nozzle

| Parameter | Trial 1 |
|---|---|
| Batch Size (kg) | 200 |
| Solids % | 20 |
| Feed Rate (kg/hr) | 178 |
| Pressure Feed (bar) | 52 |
| Inlet Temp (° C.) | 158 |
| Outlet Temp (° C.) | 65 |
| PS $d_{10}/d_{50}/d_{90}$/mean (μm) | 3/14/34 |
| Post Spray LOD (%) | 0.6 |

Organic volatile impurities, including the spray dry solvent ethanol and residual acetone from ledipasvir acetone solvate are rapidly removed during secondary drying at 60° C. Smaller scale production can be tray dried. On larger scale batches, a double cone dryer or an agitated dryer can be used. Loss on drying (LOD) was proportionately slower and is attributable to water, which was later confirmed by Karl Fischer titration.

Residual ethanol was reduced below ICH guidelines of 0.5% w/w by 6 hours of drying (or 8 hours for larger scale). Ethanol content upon completion of drying was 0.08% w/w, and residual acetone was 0.002%, indicating that the secondary drying process is adequate for removal of residual solvent.

C. Tablet Preparation i. Monolayer Tablet

Ledipasvir:copovidone solid dispersion (1:1) was made by dissolving ledipasvir and copovidone into ethanol, and then spray drying the mixture. The spray dried ledipasvir:copovidone solid dispersion is further dried in a secondary dryer. The amorphous solid dispersion comprising ledipasvir was blended with sofosbuvir and excipients and milled to facilitate mixing and blend uniformity. Either a coblend or codry granulation process can be used. Coblend granulation is a multi-step process consisting of separate dry granulations for each active ingredient with excipients followed by the blending of the two granulations together. Codry granulation consisted of dry granulating both active ingredients and excipients together. The coblend and codry processes demonstrated comparable physical and chemical tablet properties. Exemplary coblend and codry formulations are provided in Table 3 and Table 4 shown below.

TABLE 3

Representative Example Composition of Sofosbuvir/Ledipasvir Codry (Co-granulated) Tablets at Various Fill Weights

| Intra-granular | % w/w Tablet | | | |
|---|---|---|---|---|
| Sofosbuvir | 50.00 | 40.00 | 36.36 | 33.33 |
| Ledipasvir:Copovidone Solid Dispersion (1:1) | 22.50 | 18.00 | 16.36 | 15.00 |
| Lactose Monohydrate | 6.67 | 16.33 | 23.19 | 26.11 |
| Microcrystalline cellulose | 3.33 | 8.17 | 11.60 | 13.05 |
| Croscarmellose Sodium | 2.50 | 2.50 | 2.50 | 2.50 |
| Silicon Dioxide | 1.00 | 1.00 | 1.00 | 1.00 |
| Magnesium stearate | 0.75 | 0.75 | 0.75 | 0.75 |
| Extra-granular | | | | |
| Microcrystalline cellulose | 10.00 | 10.00 | 5.00 | 5.00 |
| Croscarmellose Sodium | 2.50 | 2.50 | 2.50 | 2.50 |
| Magnesium stearate | 0.75 | 0.75 | 0.75 | 0.75 |
| Fill wt (mg) | 800 | 1000 | 1100 | 1200 |

TABLE 4

Representative Example Composition of Sofosbuvir/Ledipasvir Coblend (Bi-granulated) Tablets

| | Composition | % w/w Intra-granular Blend | % w/w Tablet | mg/Tablet |
|---|---|---|---|---|
| Sofosbuvir Intra-granular Blend | Sofosbuvir | 80 | 40 | 400 |
| | Microcrystalline cellulose | 6 | 3 | 30 |
| | Lactose Monohydrate | 6 | 3 | 30 |
| | Croscarmellose Sodium | 4 | 2 | 20 |
| | Silicon Dioxide | 3 | 1.5 | 15 |
| | Magnesium stearate | 1 | 0.5 | 5 |
| | Intra-granular Subtotal | 100 | 50 | 500 |
| Ledipasvir Intra-granular Blend | Ledipasvir:Copovidone Solid Dispersion | 42.4 | 18 | 180 |
| | Microcrystalline cellulose | 43.5 | 18.5 | 185 |

TABLE 4-continued

Representative Example Composition of Sofosbuvir/Ledipasvir Coblend (Bi-granulated) Tablets

|  | Composition | % w/w Intra-granular Blend | % w/w Tablet | mg/Tablet |
|---|---|---|---|---|
|  | Croscarmellose Sodium | 9.4 | 4 | 40 |
|  | Silicon Dioxide | 3.5 | 1.5 | 15 |
|  | Magnesium stearate | 1.2 | 0.5 | 5 |
|  | Intra-granular Subtotal | 100 | 42.5 | 425 |
| Extra-granular | Microcrystalline cellulose | — | 5 | 50 |
|  | Croscarmellose Sodium | — | 2 | 20 |
|  | Magnesium stearate | — | 0.5 | 5 |
|  | Total | — | 100 | 1000 |
| Coating | Film Coat | — | 3 | 30 |
|  | Purified water | — | — | — |

The granules were then mixed with a lubricant prior to tablet compression. The total resulting core tablet weight was 1000 mg.

Film-coating of the tablets is provided to reduce photolytic degradation. Tablets were coated to a target 3% weight gain. The film-coating material was a polyvinylalcohol-based coating. Exemplary tablet formulation is provided in Table 5.

TABLE 5

Representative Example of the Composition of Tablets Comprising the Solid Dispersion of Ledipasvir and Sofosbuvir

| Ingredient | % w/w | Component Weight (mg/tablet) |
|---|---|---|
| Sofosbuvir | 40.00 | 400 |
| Ledipasvir Solid Dispersion | 18.00 | 180.0 |
| Lactose Monohydrate | 16.50 | 165.0 |
| Microcrystalline Cellulose | 18.00 | 180.0 |
| Croscarmellose Sodium | 5.00 | 50.0 |
| Colloidal Silicon Dioxide | 1.00 | 10.0 |
| Magnesium Stearate | 1.50 | 15 |
| Total Tablet Core Weight | 100.0 | 1000.0 |
| Film coating | 3.00 | 30.0 |
| Purified Water | — | — |
| Total Coated Tablet Weight |  | 1030.0 | ii. Bilayer Tablet

Tablets comprising the co-formulation of a solid dispersion comprising ledipasvir and crystalline sofosbuvir can also be made as a bilayer tablet wherein each active ingredient is in a separate layer. To make the bilayer tablet, a ledipasvir:copovidone (1:1) solid dispersion is made by dissolving ledipasvir and copovidone into ethanol, and then spray drying the mixture. The spray dried ledipasvir:copovidone solid dispersion is further dried in a secondary dryer. Next, the spray dried ledipasvir:copovidone solid dispersion is then blended with excipients. The mixture is milled and then blended with lubricant prior to dry granulation. The ledipasvir granules are blended with extragranular lubricant. Separately, the sofosbuvir drug substance is blended with excipients, and then the mixture is milled and then blended with lubricant prior to dry granulation. The sofosbuvir granules are then blended with extragranular lubricant. Finally, the sofosbuvir powder blend and ledipasvir powder blend are compressed into bilayer tablet cores. The bilayer tablet cores are then film-coated prior to packaging. A representative example composition of a bilayer tablet comprising the solid dispersion of ledipasvir and sofosbuvir is shown in Table 6. In this table, the solid dispersion comprises ledipasvir:copovidone in a 1:1 ratio.

TABLE 6

Representative Example of Composition of Bilayer Tablets Comprising the Solid Dispersion of Ledipasvir and Sofosbuvir

| Ingredient | % w/w | Component Weight (mg/tablet) |
|---|---|---|
| Layer 1 | | |
| Sofosbuvir | 33.34 | 400.0 |
| Lactose Monohydrate | 5.66 | 68.0 |
| Microcrystalline Cellulose | 7.50 | 90.0 |
| Croscarmellose Sodium | 2.00 | 24.0 |
| Colloidal Silicon Dioxide | 0.50 | 50.0 |
| Magnesium Stearate | 1.00 | 12.0 |
| Layer 2 | | |
| Ledipasvir Solid Dispersion | 15.00 | 180.0 |
| Lactose Monohydrate | 15.00 | 180.0 |
| Microcrystalline Cellulose | 17.00 | 204.0 |
| Croscarmellose Sodium | 2.50 | 30.0 |
| Magnesium Stearate | 0.50 | 6.0 |
| Total Tablet Core | 100.00 | 1200 |

Example 3

PK, Stability and Dissolution Properties of Ledipasvir Single-Agent Tablets and Ledipasvir/Sofosbuvir Tablets and Reduction of Food-Effect and Effects of Gastric Acid Suppressants A. Ledipasvir Single-Agent Tablets Bioavailability A series of in vivo experiments were conducted to evaluate the potential benefit of the solid dispersion approach relative to conventional formulations, as well as to optimize the solid dispersion by identifying the most beneficial polymer type and relative polymer concentration within the dispersion.

Equivalent bioavailability was achieved between formulations comprising the free base amorphous form (4% w/w, 10 mg amorphous free base tablet) and formulations comprising the D-tartrate salt of ledipasvir (5.85% w/w, 10 mg D-tartrate salt tablet), both using conventional formulations, in the pentagastrin pretreated dog model, as shown in Table 7. Pentagastrin is a synthetic polypeptide that stimulates the secretion of gastric acid, pepsin, and intrinsic factor.

TABLE 7

Mean (RSD) Pharmacokinetic Parameters of Ledipasvir Following Oral Administration of Tablets, 25 mg, in Beagle Dogs (n = 6)

| Drug Substance Form | Pretreatment | $C_{max}$ (nM) | $AUC_{0-24}$ (nM * hr) | F (%) |
|---|---|---|---|---|
| Amorphous Free base | Pentagastrin | 743 (17) | 8028 (22) | 71 |
| Crystalline D-tartrate Salt | Pentagastrin | 665 (38) | 7623 (44) | 67 |

Because these formulations displayed similar PK properties and the isolation properties of the D-tartrate salt were preferable to the free base amorphous form, the crystalline D-tartrate salt formulation was chosen to compare to the amorphous solid dispersion compositions. For these studies, 30 mg tablets comprising the crystalline D-tartrate salt of ledipasvir and 30 mg or 90 mg tablets comprising the amorphous solid dispersion of ledipasvir were used. Dog pharmacokinetic results for select immediate release ledipasvir tablets comprising ledipasvir solid dispersions are shown in Table 8.

TABLE 8

Mean (RSD) Pharmacokinetic Parameters of Ledipasvir after Oral Administration of Ledipasvir Tablets, Fasted Beagle Dogs (n = 6)

| Polymer | Ledipasvir: polymer Ratio | Dose (mg) | Pretreatment | $C_{max}$ (nM) | $AUC_{0-24}$ (nM*hr) | F (%) |
|---|---|---|---|---|---|---|
| Crystalline D-tartrate Ledipasvir Tablets | N/A | 30 | Pentagastrin | 665 (38) | 7623 (44) | 67 |
| | | | Famotidine | 154 (44) | 1038 (41) | 9 |
| | | 90 | Pentagastrin | 1831 (28) | 18086 (36) | 54 |
| | | | Famotidine | 349 (37) | 3322 (40) | 10 |
| Amorphous Solid Dispersion Ledipasvir Tablet: HPMC | 2:1 | 30 | Famotidine | 251 (51) | 2553 (54) | 22 |
| Amorphous Solid Dispersion Ledipasvir Tablet: Copovidone | 2:1 | 30 | Famotidine | 369 (26) | 3383 (36) | 30 |
| | 1:1 | | Pentagastrin | 983 (22) | 10541 (24) | 93 |
| | 1:1 | | Famotidine | 393 (30) | 3930 (20) | 35 |
| | 1:1 | 90 | Pentagastrin | 1644 (38) | 20908 (41) | 62 |
| | 1:1 | | Famotidine | 740 (24) | 7722 (28) | 23 |

Compared to the crystalline D-tartrate ledipasvir formulations, the amorphous solid dispersion tablets displayed higher bioavailability with lower variability. In pentagastrin pretreated animals, an approximate 40% increase in exposure and a 2-fold decrease in variability were noted. More importantly in famotidine pretreated animals, up to a 3.5-fold increase in bioavailability was observed compared to the D-tartrate salt tablet formulations.

A copovidone-based dispersion increased bioavailability more than the equivalent hypromellose-based formulation (F=30% and 22%, respectively) when spray dried at 2:1 API:polymer ratio. Bioavailability of the copovidone-based formulation was further enhanced by increasing the fraction of polymer to a 1:1 ratio, resulting in a bioavailability of 35% in famotidine pretreated dogs.

Because of the improved in vivo performance and acceptable stability and physical properties, a 1:1 mixture of ledipasvir:copovidone was chosen as the spray-dried material.

Formulations comprising the amorphous solid dispersions proved to be advantageous over formulations comprising either the amorphous free base or the D-tartrate salt. It was observed that the bioavailability of amorphous free base formulations was similar to D-tartrate salt formulations. Additional data showed a decrease in bioavailability when ledipasvir was dosed with gastric acid suppressing agents (famotidine), indicating an unfavorable drug-drug interaction in free base amorphous and D-tartrate salt formulations of ledipasvir. A solid dispersion using spray drying with a hydrophilic polymer was identified to have acceptable stability, physical characteristics, and in vivo performance. A rapidly disintegrating tablet was developed using a dry granulation process and commonly used excipients. A bioavailability study comparing formulations comprising the D-tartrate salt with formulations comprising the amorphous solid dispersion showed improved biopharmaceutical performance and overcame much of the negative drug-drug interactions with acid suppressive therapies seen in the D-tartrate salt formulations.

B. Ledipasvir+Sofosbuvir Tablets Bioavailability

PK results for the combination of sofosbuvir with ledipasvir (wherein the ledipasvir is in solid dispersion with copovidone in a 1:1) are shown in Table 9, and demonstrate lack of a significant interaction between sofosbuvir and ledipasvir.

TABLE 9

Pharmacokinetic Data for Sofosbuvir and Ledipasvir on Administration of Sofosbuvir and Ledipasvir Alone or in Combination

| Mean (% CV) | Sofosbuvir alone | Sofosbuvir + Ledipasvir | % GMR (90% CI) |
|---|---|---|---|
| Sofosbuvir (n = 17) | | | |
| $AUC_{inf}$ (ng · hr/mL) | 794 (36.4) | 1750 (27.8) | 229 (191, 276) |
| $AUC_{last}$ (ng · hr/mL) | 788 (36.6) | 1740 (27.8) | 230 (191, 277) |
| $C_{max}$ (ng/mL) | 929 (52.3) | 1870 (27.9) | 221 (176, 278) |
| Metabolite I (n = 17) | | | |
| $AUC_{inf}$ (ng · hr/mL) | 1110 (31.6) | 1950 (22.8) | 182 (157, 210) |
| $AUC_{last}$ (ng · hr/mL) | 1060 (32.7) | 1890 (22.8) | 179 (155, 207) |
| $C_{max}$ (ng/mL) | 312 (38.7) | 553 (26.6) | 182 (154, 216) |
| Metabolite II (n = 17) | | | |
| $AUC_{inf}$ (ng · hr/mL) | 10900 (17.5) | 13000 (16.7) | 119 (113, 125) |
| $AUC_{last}$ (ng · hr/mL) | 10200 (17.9) | 12100 (15.5) | 119 (113, 126) |
| $C_{max}$ (ng/mL) | 1060 (17.3) | 864 (20.1) | 81.2 (76.9, 85.8) |
| Ledipasvir (n = 17) | | | |
| Mean (% CV) | Ledipasvir alone | Sofosbuvir + Ledipasvir | % GMR (90% CI) |
| $AUC_{inf}$ (ng · hr/mL) | 11900 (26.2) | 11400 (27.0) | 95.7 (92.1, 99.5) |
| $AUC_{last}$ (ng · hr/mL) | 755 (24.7) | 734 (27.0) | 96.5 (89.9, 104) |
| $C_{max}$ (ng/mL) | 375 (28.8) | 360 (31.2) | 95.5 (91.9, 99.1) |

Sofosbuvir plasma exposure was increased by ~2.3-fold by ledipasvir. The effect of ledipasvir on sofosbuvir is likely due to inhibition of P-gp, of which Sofosbuvir is a known substrate. The increase in sofosbuvir was not considered significant due to its very low and transient exposure relative to total drug related material (DRM) exposure (DRM, calculated as the sum of the AUCs for each of the analytes, corrected for molecular weight). Based on this calculation, the AUC of sofosbuvir with ledipasvir is only ~5.7% of DRM AUC. The exposure of metabolite II, the major circulating sofosbuvir metabolite, was not impacted by the administration of ledipasvir, and demonstrates the lack of significant interaction between sofosbuvir and ledipasvir.

C. Reduction of Food Effect in Solid Dispersions of Ledipasvir and Ledipasvir/Sofosbuvir Tablets Ledipasvir alone in a conventional formulation (not the solid dispersion) has been demonstrated to have a negative food effect. Table 10 summarizes PK parameters of ledipasvir following a single dose of ledipasvir, 30 mg, under fasted and fed conditions. The ledipasvir PK profile was altered in the presence of food. Specifically, the high-fat meal appeared to delay ledipasvir absorption, prolong $T_{max}$ (median $T_{max}$ of 8 hours), and decreased ledipasvir plasma exposure (approximately 45% decrease each in mean $C_{max}$, $AUC_{last}$, and $AUC_{inf}$ respectively).

TABLE 10

Plasma Ledipasvir PK Parameters Following Single-dose Administration of Ledipasvir by Concomitant Food Intake Status

| | Mean (% CV) | |
| --- | --- | --- |
| PK Parameter | Ledipasvir 30 mg (N = 8) | Ledipasvir 30 mg Fed (N = 8) |
| $C_{max}$ (ng/mL) | 73.1 (50.8) | 36.5 (22.6) |
| $T_{max}$ (h) | 6.00 (5.00, 6.00) | 8.00 (7.00, 8.00) |
| $AUC_{last}$ (ng · h/mL) | 1988.2 (58.2) | 996.5 (21.6) |
| $AUC_{inf}$ (ng · h/mL) | 2415.9 (60.3) | 1175.0 (25.3) |
| t½ (h) | 39.82 (33.15, 41.65) | 36.83 (22.19, 49.08) |
| CL/F (mL/h) | 17,034.5 (58.6) | 26,917.9 (23.6) |
| $V_z/F$ (mL) | 876,546.3 (44.2) | 1,386,469 (24.9) |
| $C_{last}$ (ng/mL) | 6.8 (68.0) | 3.1 (42.2) |

Table 11 presents the ratio of the GLSMs (ledipasvir 30 mg under fasted conditions/ledipasvir 30 mg under fed conditions) for each of the primary PK parameters.

TABLE 11

Statistical Evaluations of Ledipasvir PK Parameters for Food Effect

| | Geometric Least Squares Mean (GLSM) | | | |
| --- | --- | --- | --- | --- |
| | Ledipasvir 30 mg Fed (N = 8) | Ledipasvir 30 mg Fasted (N = 8) | GLSM Ratio (Fed/Fasted) % | 90% Confidence Interval |
| $C_{max}$ (ng/mL) | 35.87 | 65.33 | 54.90 | 39.10, 77.08 |
| $AUC_{last}$ (ng · hr/mL) | 977.76 | 1724.28 | 56.71 | 38.87, 82.73 |
| $AUC_{inf}$ (ng · hr/mL) | 1143.64 | 2058.78 | 55.55 | 36.88, 83.67 |

Similar median half-lives of ledipasvir were observed independent of administration under fasted or fed conditions ($t_{1/2}$ of 39.82 hours under fasted conditions vs 36.83 hours under fed conditions) indicating that food decreased the bioavailability of ledipasvir by reducing its solubility and/or absorption.

Because ledipasvir has been demonstrated to have a negative food effect, the composition comprising both sofosbuvir and ledipasvir (as solid dispersion in copovidone (1:1)) was tested for a food effect. These results are shown in Table 12. Food slowed the rate of absorption of sofosbuvir (median $T_{max}$: 1.00 vs 2.00 hours) with only modest alteration in the bioavailability, as evidenced by increases of 2-fold or less in sofosbuvir and sofosbuvir metabolite I plasma exposure. For sofosbuvir metabolite II, an approximately 20-30% lower $C_{max}$ was observed upon sofosbuvir administration with food with no change in AUC. The % GMR and associated 90% CI (fed/fasted treatments) for AUC of sofosbuvir metabolite II were within the equivalence bounds of 70% to 143%. Since the decrease in sofosbuvir metabolite II $C_{max}$ was modest and the AUC parameters met the equivalence criteria, the effect of food on sofosbuvir metabolite II was not considered significant.

Similar ledipasvir plasma exposures (AUC and $C_{max}$) were achieved upon administration of ledipasvir under fasted or fed conditions. The % GMR and associated 90% CIs (fed/fasted treatments) were within the equivalence bounds of 70-143%. While a "negative" food effect was previously observed on ledipasvir when administered alone (as the amorphous free base, not solid dispersion), the pharmacokinetics of ledipasvir (amorphous solid dispersion; copovidone (1:1)) administered in combination with sofosbuvir does not appear to be altered by food. As such, the combination of sofosbuvir and ledipasvir may be administered without regard to food.

TABLE 12

Pharmacokinetic Data for Sofosbuvir, Sofosbuvir Metabolites I and II, and Ledipasvir on Administration of Sofosbuvir/Ledipasvir Tablets Fasted or with a Moderate-Fat Meal or with a High-Calorie/High Fat Meal

| | Sofosbuvir (n = 29) | | |
| --- | --- | --- | --- |
| Mean (% CV) | Sofosbuvir/Ledipasvir Tablet Fasted | Sofosbuvir/Ledipasvir Tablet Moderate-Fat Meal | % GMR (90% CI) [Moderate-Fat/Fasted] |
| $AUC_{inf}$ (ng · hr/mL) | 1520 (39.5) | 2860 (33.4) | 195 (176, 216) |
| $AUC_{last}$ (ng · hr/mL) | 1520 (39.7) | 2850 (33.5) | 195 (176, 216) |
| $C_{max}$ (ng/mL) | 1240 (49.6) | 1520 (39.8) | 126 (109, 147) |

TABLE 12-continued

Pharmacokinetic Data for Sofosbuvir, Sofosbuvir Metabolites I and II, and Ledipasvir on Administration of Sofosbuvir/Ledipasvir Tablets Fasted or with a Moderate-Fat Meal or with a High-Calorie/High Fat Meal

|  | Sofosbuvir/Ledipasvir Tablet Fasted | Sofosbuvir/Ledipasvir Tablet High-Calorie/High-Fat Meal | GMR (90% CI) [High-Fat/Fasted] |
|---|---|---|---|
| $AUC_{inf}$ (ng · hr/mL) | 1520 (39.5) | 2570 (34.0) | 179 (162, 198) |
| $AUC_{last}$ (ng · hr/mL) | 1520 (39.7) | 2550 (34.6) | 178 (161, 198) |
| $C_{max}$ (ng/mL) | 1240 (49.6) | 1350 (42.5) | 115 (99.0, 134) |

Sofosbuvir Metabolite I (n = 29)

| Mean (% CV) | Sofosbuvir/Ledipasvir Tablet Fasted | Sofosbuvir/Ledipasvir Tablet Moderate-Fat Meal | % GMR (90% CI) [Moderate-Fat/Fasted] |
|---|---|---|---|
| $AUC_{inf}$ (ng · hr/mL) | 1520 (42.0) | 2520 (21.4) | 177 (163, 192) |
| $AUC_{last}$ (ng · hr/mL) | 1470 (43.3) | 2460 (21.8) | 180 (164, 196) |
| $C_{max}$ (ng/mL) | 352 (42.7) | 495 (22.2) | 151 (136, 167) |

|  | Sofosbuvir/Ledipasvir Tablet Fasted | Sofosbuvir/Ledipasvir Tablet High-Calorie/High-Fat Meal | GMR (90% CI) [High-Fat/Fasted] |
|---|---|---|---|
| $AUC_{inf}$ (ng · hr/mL) | 1520 (42.0) | 2550 (22.2) | 181 (166, 196) |
| $AUC_{last}$ (ng · hr/mL) | 1470 (43.3) | 2500 (22.5) | 184 (168, 201) |
| $C_{max}$ (ng/mL) | 352 (42.7) | 501 (26.8) | 154 (139, 171) |

Sofosbuvir Metabolite II (n = 29)

| Mean (% CV) | Sofosbuvir/Ledipasvir Tablet Fasted | Sofosbuvir/Ledipasvir Tablet Moderate-Fat Meal | % GMR (90% CI) [Moderate-Fat/Fasted] |
|---|---|---|---|
| $AUC_{inf}$ (ng · hr/mL) | 11800 (23.0) | 13800 (17.7) | 117 (112, 123) |
| $AUC_{last}$ (ng · hr/mL) | 11300 (23.4) | 12900 (18.2) | 114 (108, 121) |
| $C_{max}$ (ng/mL) | 865 (26.6) | 700 (19.5) | 81.5 (75.6, 87.9) |

|  | Sofosbuvir/Ledipasvir Tablet Fasted | Sofosbuvir/Ledipasvir Tablet High-Calorie/High-Fat Meal | GMR (90% CI) [High-Fat/Fasted] |
|---|---|---|---|
| $AUC_{inf}$ (ng · hr/mL) | 11800 (23.0) | 12900 (18.5) | 112 (107, 118) |
| $AUC_{last}$ (ng · hr/mL) | 11300 (23.4) | 12100 (20.1) | 110 (103, 116) |
| $C_{max}$ (ng/mL) | 865 (26.6) | 600 (22.9) | 70.2 (65.0, 75.8) |

Ledipasvir (n = 29)

| Mean (% CV) | Sofosbuvir/Ledipasvir Tablet Fasted | Sofosbuvir/Ledipasvir Tablet Moderate-Fat Meal | % GMR (90% CI) [Moderate-Fat/Fasted] |
|---|---|---|---|
| $AUC_{inf}$ (ng · hr/mL) | 10600 (57.2) | 10600 (35.6) | 115 (99.4, 134) |
| $AUC_{last}$ (ng · hr/mL) | 8600 (53.8) | 8650 (32.1) | 114 (98.0, 133) |
| $C_{max}$ (ng/mL) | 324 (44.8) | 319 (24.8) | 109 (93.5, 126) |

|  | Sofosbuvir/Ledipasvir Tablet Fasted | Sofosbuvir/Ledipasvir Tablet High-Calorie/High-Fat Meal | GMR (90% CI) [High-Fat/Fasted] |
|---|---|---|---|
| $AUC_{inf}$ (ng · hr/mL) | 10600 (57.2) | 9220 (36.1) | 103 (88.5, 119) |
| $AUC_{last}$ (ng · hr/mL) | 8600 (53.8) | 7550 (33.9) | 104 (88.8, 121) |
| $C_{max}$ (ng/mL) | 324 (44.8) | 255 (25.9) | 88.2 (75.8, 103) |

D. Reduction of Effects of Gastric Acid Suppressants in Ledipasvir/Sofosbuvir Tablets Ledipasvir, 30 mg, alone in both a conventional formulation (as the D-tartrate salt) and as the solid dispersion has been demonstrated to have a decrease in bioavailability when administered with some gastric acid suppressants; most significantly, proton-pump inhibitors (PPI's, e.g., omeprazole), but also including histamine-2 antagonists (H2RA's, e.g., famotidine, data not included). Table 12A summarizes PK parameters of ledipasvir following administration of ledipasvir conventional single agent tablets, 30 mg, ledipasvir tablets as solid dispersion (ledipasvir:copovidone 1:1), 30 mg, and sofosbuvir/ledipasvir FDC tablets (90 mg of ledipasvir solid dispersion comprising copovidone 1:1) with and without omeprazole. The bioavailability of ledipasvir as single agent tablets was reduced approximately 2-fold when administered with omeprazole; however, administration of ledipasvir as part of the sofosbuvir/ledipasvir FDC tablet with omeprazole resulted in no significant decrease in ledipasvir exposure (AUC and Cmax) compared to sofosbuvir/ledipasvir FDC tablet administration in absence of omeprazole.

TABLE 12A

Pharmacokinetic Data for Ledipasvir on Administration of Ledipasvir Single Agent Tablets or Sofosbuvir/Ledipasvir Tablets with and without Omeprazole

| Mean (% CV) | Ledipasvir alone | Ledipasvir + Omeprazole | % GMR (90% CI) |
|---|---|---|---|
| Ledipasvir, Conventional Formulation (N = 10) | | | |
| $AUC_{tau}$ (ng · hr/mL) | 1640 (18.5) | 865 (37.7) | 50.7 (43.4, 59.3) |
| $C_{max}$ (ng/mL) | 99.0 (20.1) | 51.2 (39.2) | 49.7 (41.7, 59.1) |
| $C_{tau}$ (ng/mL) | 52.2 (22.1) | 28.3 (36.0) | 52.4 (44.3, 61.9) |
| Ledipasvir, Solid Dispersion (N = 17) | | | |
| $AUC_{inf}$ (ng · hr/mL) | 2140 (38.8) | 1300 (50.7) | 58.5 (48.3, 70.8) |
| $AUC_{last}$ (ng · hr/mL) | 1850 (33.5) | 1070 (45.5) | 56.3 (46.4, 68.3) |
| $C_{max}$ (ng/mL) | 64.8 (32.9) | 36.2 (55.9) | 52.2 (41.4, 65.9) |
| Ledipasvir, SOF/LDV FDC (N = 16) | | | |
| Mean (% CV) | SOF/LDV FDC Alone | SOF/LDV FDC + Omeprazole | % GMR (90% CI) |
| $AUC_{inf}$ (ng · hr/mL) | 7990 (66.2) | 6660 (51.8) | 96.0 (66.5, 139) |
| $AUC_{last}$ (ng · hr/mL) | 7160 (65.8) | 5700 (51.8) | 92.5 (64.8, 132) |
| $C_{max}$ (ng/mL) | 242 (68.6) | 176 (51.1) | 89.1 (60.9, 130) |

E. Dissolution of Ledipasvir/Sofosbuvir Tablets

Figure 5:
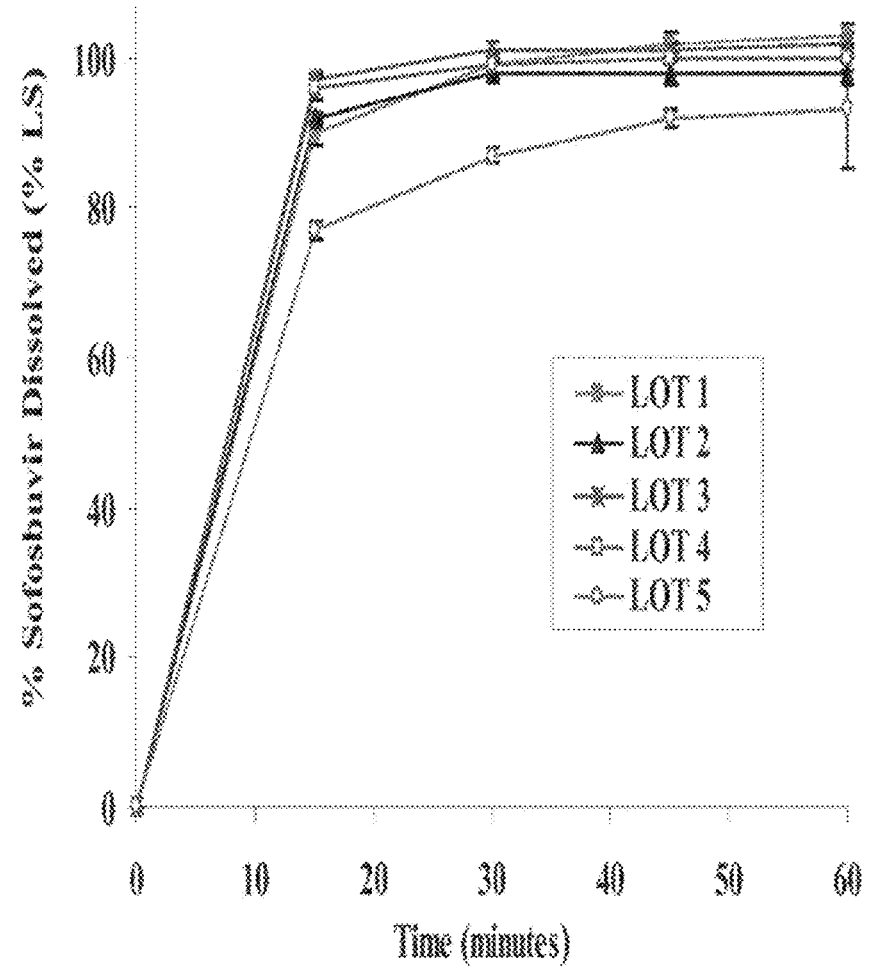
FIG. 5 shows the dissolution of sofosbuvir in the sofosbuvir (400 mg)/ledipasvir (90 mg) combination described in Example 7.
Figure 6:
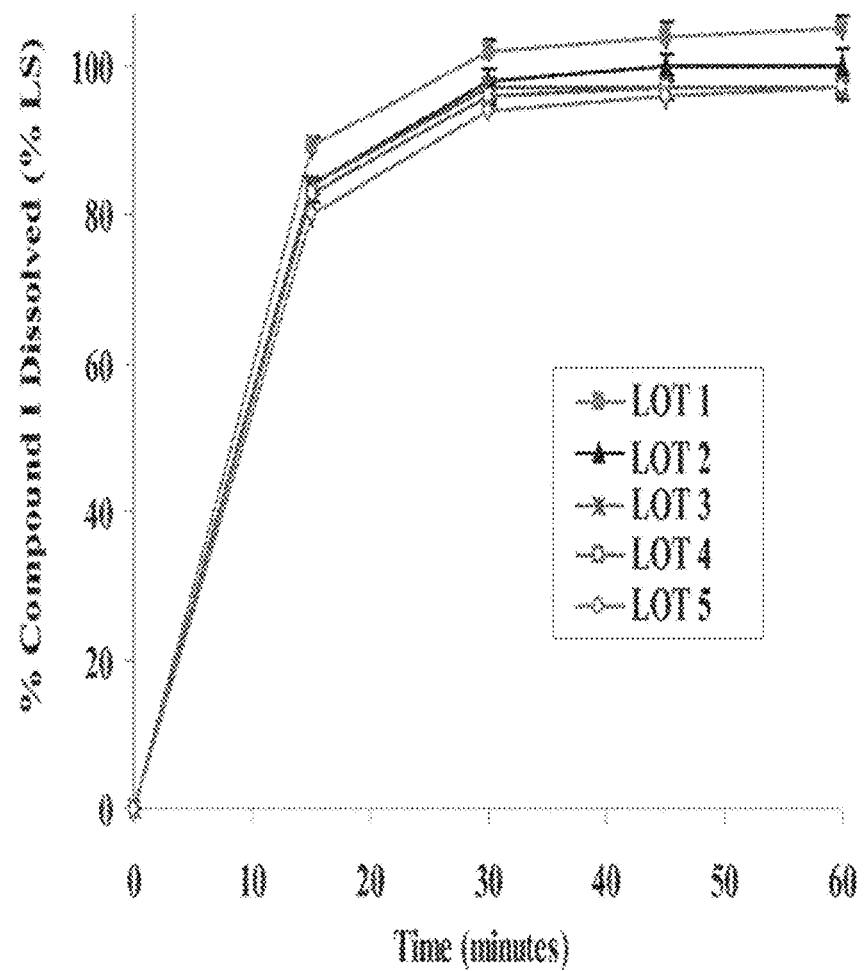
FIG. 6 shows the dissolution of ledipasvir in the sofosbuvir (400 mg)/ledipasvir (90 mg) combination formulation described in Example 3.

Dissolution studies were conducted comparing the sofosbuvir 400 mg/ledipasvir 90 mg tablets (ledipasvir:copovidone (1:1). The sofosbuvir/ledipasvir tablets (LOT 1-5) display greater than 85% sofosbuvir (FIG. 5) and ledipasvir (FIG. 6) dissolved in 30 minutes for both tablet formulations. These results are shown in FIGS. 5 and 6.

Example 4

Stability of Sofosbuvir/Ledipasvir Co-Formulation

The compatibility of sofosbuvir anhydrous crystalline drug substance was evaluated with the ledipasvir:copovidone solid dispersion. A blend of the sofosbuvir and ledipasvir:copovidone (1:1) solid dispersion was prepared at a ratio representative of the final 400 mg sofosbuvir/90 mg ledipasvir tablets. The blend was compressed into pellets and placed in stability chambers at 40° C./75% RH and 60° C./ambient humidity and tested after two and four weeks of storage in open glass vials. The results summarized in Table 13 show that no degradation was observed for either sofosbuvir or ledipasvir, demonstrating the chemical compatibility of sofosbuvir and the ledipasvir:copovidone solid dispersion with each other.

TABLE 13

Strength and Impurity Content of Sofosbuvir and Ledipasvir:Copovidone Solid Dispersion Blend Stored at 40° C./75% RH and 60° C.

| | | Ledipasvir | | Sofosbuvir | |
|---|---|---|---|---|---|
| Condition | Time (weeks) | Strength (%) | Total Impurity Content (%) | Strength (%) | Total Impurity Content (%) |
| 45° C./75% RH | 0 | 98.8 | 0.0 | 102.9 | 0.4 |
| | 2 | 96.9 | 0.0 | 101.6 | 0.3 |
| | 4 | 97.1 | 0.0 | 100.5 | 0.2 |
| 60° C. | 0 | 98.8 | 0.0 | 102.9 | 0.4 |
| | 1 | 99.2 | 0.0 | 102.4 | 0.3 |
| | 2 | 99.6 | 0.0 | 103.2 | 0.3 |
| | 4 | 98.9 | 0.0 | 102.8 | 0.2 |

Example 5

Efficacy of Sofosbuvir/Ledipasvir/Ribavirin Treatment in Patients with HCV Infections Patients with HCV infections were treated with either the combination of sofosbuvir, ledipasvir, and ribavirin or the combination of sofosbuvir and ribavirin. Patients used in the study included those that were treatment naïve, i.e. had not previously been treated for HCV and those that were null responders, i.e. had previously been treated for HCV but failed to respond to the treatment. Standard doses (90 mg of ledipasvir, 400 mg of sofosbuvir, and 1000 mg of ribavirin, for example) were given of each drug to the patients for a duration of 12 weeks. Throughout treatment, HCV RNA was measured, and the Sustained Virologic Response (SVR) was measured after treatment was discontinued. By four weeks of treatment, almost all patients had achieved an HCV RNA measurement below the limit of detection (LOD of 15 IU/mL), and by the end of treatment, 100% of patients achieved an HCV RNA level below the LOD (Table 14).

TABLE 14

Patients with HCV RNA below the limit of detection over time.

| | Sofosbuvir + Ribavirin | | Sofosbuvir + Ribavirin + Ledipasvir | |
|---|---|---|---|---|
| | Treatment-naïve (n = 25) | Null responder (n = 10) | Treatment-naïve (n = 25) | Null responder (n = 9) |
| Week 1 | 32% | 10% | 44% | 0% |
| Week 2 | 68% | 70% | 88% | 44% |
| Week 4 | 100% | 100% | 100% | 89% |
| End of Treatment | 100% | 100% | 100% | 100% |

Surprisingly, 100% of patients receiving the combination of sofosbuvir, ledipasvir, and ribavirin achieved a sustained virologic response at four and twelve weeks post treatment. In contrast, only 88% of treatment naïve and 10% of null responder patients treated with the combination of sofosbuvir and ribavirin achieved a SVR at four weeks post treatment, and only 84% of treatment naïve and 10% of null responder patients treated with the combination of sofosbuvir and ribavirin achieved SVR at twelve weeks post treatment (Table 15).

TABLE 15

Sustained Virologic Response

|  | Sofosbuvir + Ribavirin | | Sofosbuvir + Ribavirin + Ledipasvir | |
| --- | --- | --- | --- | --- |
|  | Treatment-naïve (n = 25) | Null responder (n = 10) | Treatment-naïve (n = 25) | Null responder (n = 9) |
| SVR4 | 88% | 10% | 100% | 100% |
| SVR12 | 84% | 10% | 100% | 100% |

Figure 7:
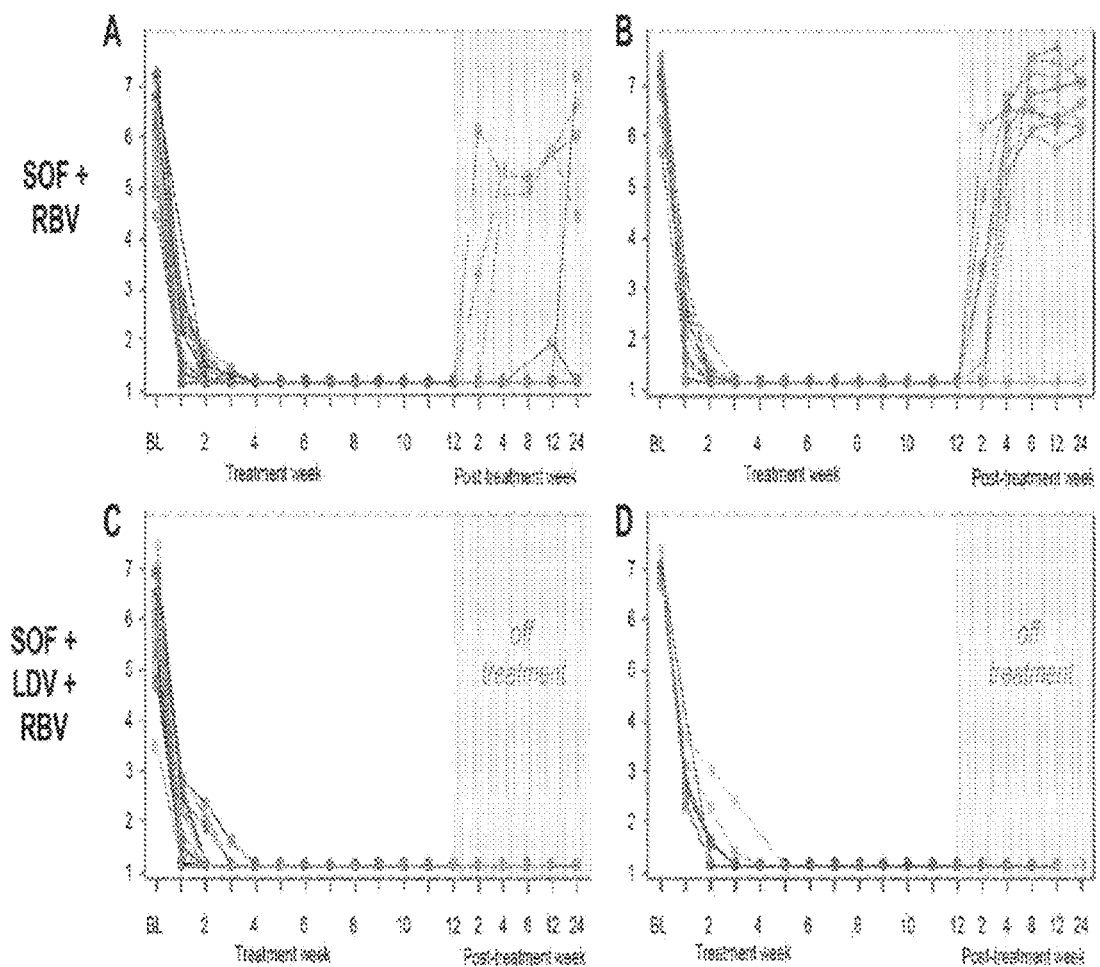
FIG. 7, with panels A-D, shows the HCV RNA levels during 12 weeks of treatment and 24 weeks post-treatment for treatment naïve (FIG. 7, panel A) or null responder (FIG. 7, panel B) patients treated with sofosbuvir (SOF) and ribavirin (RBV) and for treatment naïve (FIG. 7, panel C) or null responder (FIG. 7, panel D) patients treated with sofosbuvir (SOF), ledipasvir and ribavirin (RBV). This data and experimental method are further described in Example 5.

These results are graphically depicted FIG. 7, panels A-D and demonstrate that the addition of ledipasvir in the treatment regimen gave 100% SVR at weeks 4 and 12. Example 9, below, shows similar results are obtained with treatment regimens of less than twelve weeks (i.e. treatment regimens of about 8 or 6 weeks), and that similar results are obtained with treatment regimens of sofosbuvir and ledipasvir without the addition of ribavirin.

Example 6

Stability of SOF 400 mg/Ledipasvir 90 mg Fixed-Dose Combination Tablets

This example summarizes the physicochemical stability of packaged Sofosbuvir (SOF) 400 mg/ledipasvir 90 mg blue film-coated fixed-dose combination (FDC) tablets at 25° C./60% relative humidity (RH) and 40° C./75% RH as a function of desiccant. The ledipasvir portion of the table comprised ledipasvir:copovidone in a 1:1 ratio. In addition the chemical and physical stability of SOF/ledipasvir FDC tablets were evaluated at 40° C./75% RH under open condition for up to 4 weeks.

The physico-chemical properties that were evaluated included appearance, potency, degradant formation, dissolution rate and water content. Physical stability of the tablets in the absence of desiccant was evaluated after 24 weeks using FT-Raman spectroscopy and modulated differential scanning calorimetry (mDSC).

SOF 400 mg/ledipasvir 90 mg blue film-coated FDC tablets exhibited satisfactory stability at 25° C./60% RH and 40° C./75% RH for up to 24 weeks in the presence of 0, 1, and 3 g of desiccant. No significant changes were observed in potency, impurity content or dissolution rate. However, a ledipasvir photodegradant was present at 0.1% for all conditions. FT-Raman analysis for the tablets stored in the absence of desiccant showed no detectable crystallization after 24-weeks.

Methods and Materials

Materials

Table 16 lists the physicochemical properties for SOF drug substance and ledipasvir solid dispersion used to produce tablets. The quantities of SOF drug substance and ledipasvir solid dispersion were adjusted based on their respective drug content factor (DCF) with concomitant adjustment in the quantity of lactose monohydrate. The DCF used for SOF and ledipasvir solid dispersion powder, 50% w/w were 0.997 and 0.497 (0.994 when adjusted for the amount of copovidone), respectively.

TABLE 16

Physicochemical Properties of SOF Drug Substance and Ledipasvir Solid Dispersion, 50% w/w, Bulk Powder Used to Produce SOF 400 mg/Ledipasvir 90 mg Film-Coated FDC Tablets

| Active Ingredient | Crystal Form | Assay by HPLC (%) | Impurities (%) | Drug Content Factor | Water Content by Karl Fischer (%) | Particle Size ($\mu$m) | | |
| --- | --- | --- | --- | --- | --- | --- | --- | --- |
| | | | | | | $d_{10}$ | $d_{50}$ | $d_{90}$ |
| SOF | Anhydrous Form II | 99.8 | 0.1 | 0.996 | 0.1 | 3 | 10 | 29 |
| Ledipasvir Solid Dispersion, 50% w/w, Bulk Powder | Amorphous | 49.7 | 0.2 | 0.497 | 1.09 | 5 | 22 | 44 |

Equipment

The primary equipment used to manufacture SOF 400 mg/Ledipasvir 90 mg film-coated FDC tablets included an 12 qt. V-Blender, a screening mill (Comil 197S, Quadro, Waterloo, Canada) equipped with a 0.094 in grated screen, a roller compactor/granulator (MiniPactor, Gerteis, Jona, Switzerland) equipped equipped with a 1.0 mm milling screen and a smooth/smooth roller configuration, a 12-station instrumented rotary tablet press (XM-12, Korsch, Berlin, Germany), and a tablet coater (LabCoat, O'Hara Technologies Inc., Ontario, Canada). The diamond-shaped tablet tooling (Elizabeth Carbide Die Co., Inc., McKeesport, Pa., USA) consisted of diamond, standard concave D-type punches with dimensions of 0.7650 in ×0.4014 in (19.43 mm×10.20 mm). A 15 inch perforated pan film coater was used to coat the tablet cores.

Container Closure

Sofosbuvir/Ledipasvir FDC tablets are packaged in 100 mL white, high density polyethylene (HDPE) bottles. Each bottle contained 30 tablets and 0, 1 or 3 g silica gel desiccant canister or sachet and polyester packing material. Each bottle was enclosed with a white, continuous thread, child-resistant screw cap with an induction-sealed, aluminum-faced liner.

A selected number of bottles were left open and packaged without desiccant to evaluate the physical and chemical stability at 40° C./75% RH under accelerated heat and humidity conditions.

General Study Design

The solid state and chemical stability of the packaged lot were evaluated in the following configurations:

1) At 25° C./60% RH and 40° C./75% RH as a function of desiccant. The samples were stored under closed condition for a minimum of 24 weeks.

2) At 40° C./75% RH under open condition for up to 4 weeks.

Samples were pulled at predetermined time points. Chemical stability testing for appearance, potency, degradant formation, dissolution rate and water content was conducted. Additional physical stability assays to monitor potential crystallization and phase separation were conducted.

Physical Stability Evaluation

Physical stability tests included appearance and FT-Raman. The visual inspection was performed on stressed film-coated tablets to identify changes in tablet color and coating integrity. FT-Raman spectroscopy was used to detect potential crystalline ledipasvir (Form III) in the film-coated tablets.

Tablets were visually inspected for changes in appearance at all time points and storage conditions. In contrast, FT-Raman was only performed on tablets with 0 g desiccant at 24 weeks (25° C./60% RH and 40° C./75% RH).

Appearance

At all time points tablets were examined for physical integrity (i.e. color, shape, coating integrity and debossing).

FT-Raman

FT-Raman experiments were conducted. The 24-week SOF/ledipasvir film-coated FDC tablets stored in closed containers at 25° C./60% RH and 40° C./75% RH were analyzed using FT-Raman spectroscopy to detect the formation of crystalline ledipasvir (Form III). Briefly, the coating from the tablets was carefully removed using an Xacto™ knife followed by grinding of the tablet in a mortar and pestle. Tablet powder was then packed into cups and spectra were collected using a backscattering geometry.

Chemical Stability Evaluation

Chemical stability assays included measuring water content by Karl Fischer (KF), potency, formation of impurity/degradation products and dissolution rate were conduced.

KF Water Content

The water content was reported for SOF 400 mg/ledipasvir 90 mg film-coated FDC tablets following USP <921>.

Potency and Impurity/Degradant Formation by UPLC

The potency and degradation product formation of SOF/ledipasvir film-coated FDC tablets were evaluated by analysis of composite sample solution of 10 tablets according to STM-2542 [5]. The reference standard concentration for SOF and ledipasvir is 2.0 mg/mL and 0.45 mg/mL, respectively. The strength and degradation product content of SOF and ledipasvir was determined by UPLC using external reference standard and area normalization at wavelengths of 262 nm and 325 nm, respectively.

Dissolution Methodology

Dissolution testing was performed on SOF/ledipasvir film-coated FDC tablets. A USP type 2 dissolution apparatus with 900 mL of dissolution medium and a paddle speed of 75 rpm was used. The medium was 1.5% polysorbate 80 in 10 mM potassium phosphate buffer at pH 6.0 and the temperature was maintained at 37° C. for the duration of the assay. The extent of SOF and ledipasvir released as a function of time was monitored by UPLC using area normalization and an external reference standard at a wavelength of 250 nm.

Results

A. Physical Stability

A1. Appearance

Samples at all stability conditions and desiccant levels were visually inspected for all time points and found to resemble blue, diamond-shaped film-coated tablets.

A2. FT-Raman

The FT-Raman analysis was performed on powder extracted from tablets stored in the absence of desiccant after 24 weeks. Calculations of % crystallinity using the PLS model did not show signs of crystalline ledipasvir (Form III) above the LOD of 3% at either storage condition. This was consistent with the original sample (t=0) in which ledipasvir (Form III) was also below the LOD. Spectra from selected samples were included in a chart, from 1577 cm' to 1514 $cm^{-1}$ with the baselines artificially adjusted for clarity. This region is in one of the four spectral regions used to estimate the % ledipasvir (Form III) in tablets by PLS model.

The top two spectra (used as standards in the PLS model), in the chart, were from tablets spiked with 10% w/w and 3% w/w, of crystalline ledipasvir (Form III). The next two spectra represent stressed tablets stored for 24 weeks at 40° C./75% RH and 25° C./60% RH. The last spectrum represents the initial time point (t=0). Ledipasvir (Form III) has a distinct peak at 1552 $cm^{-1}$, which can clearly be seen in the spiked tablets with increasing intensity from 3% to 10%. The intensity in this region for the stressed samples stored for 24 weeks does not increase from the t=0 sample, indicating no change in crystallinity. Ledipasvir (Form III) in the t=0 sample and the 24 week samples is below that present in the tablets spiked with 3% Form III ledipasvir, the current limit of detection for this analytical technique.

B. Chemical Stability

B.1 KF Water Content

The water content of stressed samples stored for 4 weeks under open condition increased from 2.28% to 5.23%. The amount of water content of stressed samples stored at 25° C./60% RH decreased to 1.91%, 1.58%, and 1.65% for tablets with no desiccant, with 1 g desiccant, and 3 g desiccant, respectively. At 40° C./75% RH, the amount of water content decreased to 2.03%, 1.79%, and 1.46% for tablets without desiccant, with 1 g desiccant, and 3 g desiccant, respectively.

B.2 Potency and Impurity/Degradation Product Formation

The potency and impurity/degradation content for SOF 400 mg/ledipasvir 90 mg film-coated FDC tablets were determined at 25° C./60% RH and 40° C./75% RH. Representative chromatograms of stability samples stored at 40° C./75% RH were obtained. The data showed that SOF and ledipasvir remained chemically stable in SOF 400 mg/ledipasvir 90 mg film-coated FDC tablets stored for 24 weeks at 25° C./60% RH and 40° C./75% RH. The label strength for SOF and ledipasvir remains unchanged at 25° C./60% RH and 40° C./75% RH.

Dissolution

The dissolution profiles of SOF and ledipasvir in SOF 400 mg/ledipasvir 90 mg film-coated FDC tablets were obtained. At the 24 week time point, the tablets ranged between 99% and 100% dissolution at 45 minutes for SOF, and between 99% and 98% for ledipasvir at both 25° C./60% RH and 40° C./75% RH for all desiccant levels tested.

From the foregoing, this example shows that SOF 400 mg/ledipasvir 90 mg Film-Coated FDC tablets exhibited satisfactory stability at 25° C./60% RH and 40° C./75% RH for up to 24 weeks in the presence of 0, 1, and 3 g of desiccant. In addition, crystalline ledipasvir (Form III) was not detected by FT-Raman analysis after 24 weeks of storage.

Example 7

Formulation Development of a Fixed Dose Combination (FDC) Tablet SOF 400 mg/Ledipasvir 90 mg This example shows the development of a SOF 400 mg/ledipasvir 90 mg fixed dose combination (FDC) tablet comprising ledipasvir:copovidone (1:1). There were expected difficulties with such a development, one of which was the expected poor powder flow and the other relates to non-homogenous blend, given the existing formulations of each individual agent.

Three tablet formulations were tested, including (1) a monolayer co-granulated tablet formulation, (2) a monolayer co-blended tablet formulation and (3) a bilayer tablet formulation. In all of these formulations, SOF was in anhydrous crystalline form II and ledipasvir was in amorphous solid dispersion (ledipasvir:copovidone (1:1)).

Formulation (1) is typically associated with the highest risk of drug-drug interaction but is the most cost-effective during manufacturing. The bilayer formuation of (3), by constrast, is perceived to have the lowest drug-drug interaction risk.

Figure 8:
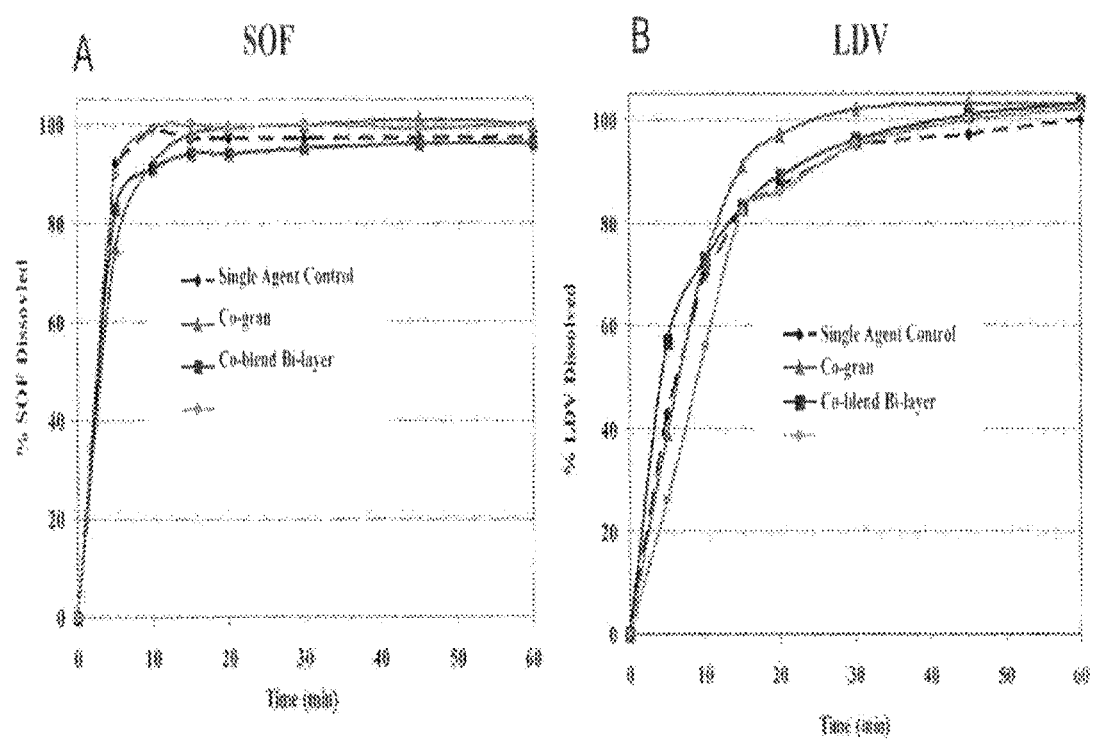
FIG. 8, with panels A-B, presents charts to show that all three formulations had comparable dissolution performance, similar to that of the single-agent controls. This is more thoroughly described in Example 7.

The dissolution performance of the formulations were tested in a dissolution media that included 10 mM phosphate buffer at pH 6.0 (1.5% Tween® 80). As shown in FIG. 8, panels A-B, all three formulations had comparable dissolution performance, similar to that of the single-agent controls.

The pharmacokinetic (PK) performance of each formulation was also tested. Plasma Concentration of SOF/ledipasvir after oral administration of SOF/ledipasvir FDC and control tablets in fasted dogs (100 mg/22.5 mg fixed/dog). Table 17 below shows the PK results.

TABLE 17

Phamacokinetic performance of the forumations in famotidine pretreated dogs

| Total Tablet weight/ Formulation | Treatment | SOF | | Ledipasvir | |
|---|---|---|---|---|---|
| | | $AUC_{0-t}$ (ng*hr/mL) | $C_{max}$ (ng/mL) | $AUC_{0-last}$ (ng*hr/mL) | $C_{max}$ (ng/mL) |
| Control SOF tablet + Ledipasvir SD tablet | Famotidine | 314 ± 207 | 503 ± 363 | 3260 ± 1312 | 345 ± 132 |
| Monolayer, Co-granulated | Famotidine | 501 ± 249 | 729 ± 434 | 3236 ± 730 | 333 ± 56 |
| Monolayer, Co-blended | Famotidine | 483 ± 406 | 652 ± 527 | 4208 ± 2216 | 444 ± 215 |
| Bilayer | Famotidine | 283 ± 193 | 288 ± 201 | 4,712 ± 2,270 | 421.7 ± 203.7 |

Based on these results, the monolayer co-granulated tablet was selected for further analysis. The composition of this formulation is provided in Table 18.

TABLE 18

Composition of SOF 400 mg/Ledipasvir 90 mg FDC Tablets

| Composition | % w/w |
|---|---|
| Intra-granular | |
| SOF | 40.00% |
| Ledipasvir SD | 18.00% |
| Lactose Fast Flow 316 | 16.50% |
| MCC 101 | 8.00% |
| Croscarmellose | 2.50% |
| Silicon Dioxide | 1.00% |
| Magnesium Stearate | 0.75% |
| Extragranular | |
| MCC 101 | 10.00% |
| Croscarmellose | 2.50% |
| Magnesium stearate | 0.75% |
| Total Fill weight Core Tablet (mg) | 1000 |
| Coating | |
| Opadry II Orange 85F13912 | 3.0% |
| Water | QS |

A bioavailability clinical study was carried out with this formulation, with single agent tablets as control, in 24 healthy patients under fasted conditions. The results are shown in Table 19.

TABLE 19

Bioavailability of SOF/Ledipasvir fixed dose combination and single agent tablets

| | | Formulation | | | |
|---|---|---|---|---|---|
| | | SOF | | Ledipasvir | |
| Total Tablet weight | Dose (mg) | $AUC_{inf}$ (ng*hr/mL) | $C_{max}$ (ng/mL) | $AUC_{inf}$ (ng*hr/mL) | $C_{max}$ (ng/mL) |
| Signle Agent Control SOF tablet + Ledipasvir SD tablet | SOF 400 mg Ledipasvir 90 mg | 11900 (23.5) | 764 (27.3) | 9620 (45.6) | 314 (40.5) |
| SOF/Ledipasvir FDC Tablet | | 12500 (23.1) | 784 (36.2) | 9570 (46.6) | 314 (45.2) |

These results, therefore, show that SOF/ledipasvir fixed dose combination (co-granulated) and single agent tablets are bioequivalent.

Example 8

Solubility Studies for Amorphous Ledipasvir

This example examines the physicochemical properties different ledipasvir forms, including amorphous and crystalline free base, solvates, and salts, with respect to solubility.

A. Materials and Methods pH-Solubility Profile

The aqueous solubility of ledipasvir amorphous free base was determined across the pH range of 1 to 10. Excess solid ledipasvir was added to a range of pH-adjusted aqueous solutions (titrated with HCl or NaOH) and stirred for 48 hours at room temperature. The suspensions were then filtered through regenerated cellulose syringe filters. The pH value of the supernatant was measured, and the supernatant was diluted as appropriate with 50:50 $H_2O$+0.1% TFA:ACN and assayed for ledipasvir content by the HPLC-UV method.

Solubility in Simulated Intestinal Media

Solubility of ledipasvir amorphous free base was assessed in three types of simulated intestinal fluids at pH 6.5 or pH 5.0; and simulated intestinal bile salt and lecithin mixture (SIBLM), pH 6.4. Excess solid ledipasvir was added to the respective SIFs and stirred for 48 hours at room temperature. The resulting suspensions were then filtered through regenerated cellulose syringe filters. The supernatant was diluted as appropriate with 50:50 $H_2O$+0.1% TFA:ACN and assayed for ledipasvir content by the HPLC-UV method.

Excipient Solubility

Solubility of ledipasvir amorphous free base and ledipasvir crystalline D-tartrate was measured in a wide range of pharmaceutically acceptable solvents, including cosolvents, surfactants, fatty acids, triglycerides, or blends thereof. Material was weighed into scintillation vials and stirred for up to 48 hours at room temperature. In many cases, solubility was higher than the amount of solid used in the sample, thus many results are reported as 'greater than' or 'greater than or equal to' if the concentration was not quantitatively determined by HPLC-UV.

Additionally, aqueous solubility was measured as a function of time in the presence of 0.1% w/w surfactants and polymers in pH 2 (50 mM citrate) and pH 5 (50 mM citrate). ledipasvir crystalline forms (acetone solvate Form II; anhydrous FB Form III; D-tartrate) and amorphous form were evaluated to identify differences in dissolution behavior. Excess solid was added to aqueous buffered solutions; samples were withdrawn at predetermined intervals (2, 5, 8, 10, 15, 20, 30, 45, 60 minutes, and 24 hours), filtered through regenerated cellulose filters, and diluted for concentration measurement by the HPLC-UV method.

B. Results

Solubility and Dissolution Rate

Figure 9:
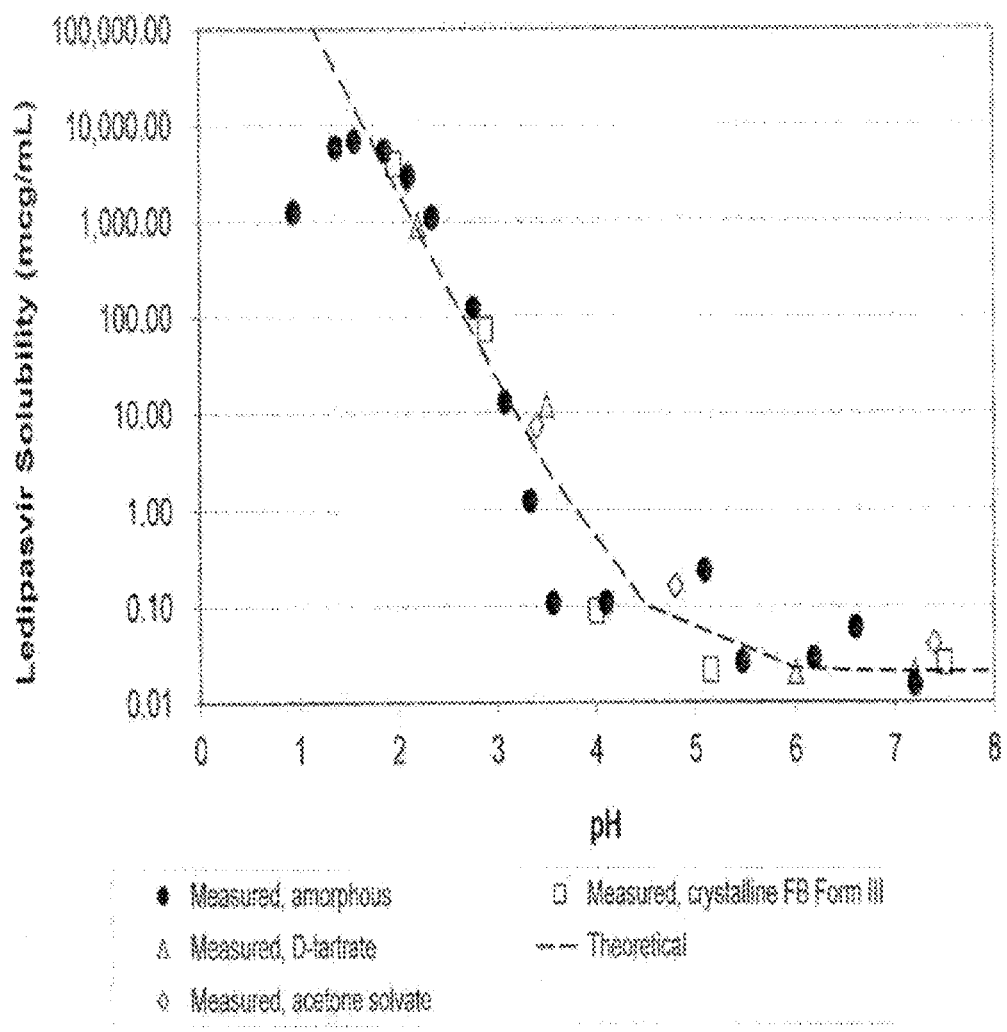
FIG. 9 presents the pH-solubility profile of ledipasvir at room temperature (RT). The line is the nonlinear least-square regression fit using equation $S_T = S_0[(1+10^{(pKa1-pH)} + 10^{(pKa1+pKa2-2 \cdot pH)})]$ with an intrinsic solubility ($S_0$) of 0.04 μg/mL and a weakly basic pKa1 and pKa2 values of 5.0 and 4.0, respectively. This is more thoroughly described in Example 8.

The pH-solubility profiles of all available ledipasvir forms were determined at room temperature and are graphically shown in FIG. 9. The flat portion of the solubility profile (pH>5) represents the intrinsic aqueous solubility of the free base. The aqueous solubility of ledipasvir significantly increases as the pH of the solution is lowered below the $pK_a$ of the ionizable groups. All forms lose crystallinity, reverting to the amorphous free base in aqueous solution, and thus show similar aqueous solubility properties at steady-state. However, dissolution properties are form dependent and are described in further detail below.

Ledipasvir Amorphous Free Base

The intrinsic solubility of ledipasvir amorphous free base (FB) is approximately 0.04 μg/mL. Under acidic conditions, the solubility increases to 1 mg/mL at pH 2.3, and peaks at about 7 mg/mL at pH 1.6, as shown in Table 20 and FIG. 9. Solubility of ledipasvir in simulated intestinal fluids is governed by both the pH of the medium and the presence of bile salts and lecithin. In fasted state simulated intestinal fluids (FaSSIF) at pH 6.5 and room temperature, the solubility is 0.025 mg/mL, and this is increased approximately 10-fold to 0.232 mg/mL in simulated bile and lecithin mixture (SIBLM, pH 6.5) due to the increased concentration of bile salts and lecithin. A similar solubility enhancement to 0.230 mg/mL is observed in fed state simulated intestinal fluid (FeSSIF, pH 5), containing lower bile salt and lecithin mixtures than SIBLM. The solubility increase in this mixture is predominantly attributed to the ionization sate of the molecule at pH 5.

TABLE 20

Solubility of Ledipasvir amorphous free base as a function of pH at room temperature

| Aqueous Media | Solubility (mg/mL) |
|---|---|
| Aqueous, pH 1.6 (HCl) | 6.855 |
| Aqueous, pH 2.3 (HCl) | 1.096 |
| Aqueous, pH 3.1 (HCl) | 0.0132 |
| Aqueous, pH 4.1 (HCl) | 0.00011 |
| Aqueous, pH 5.5 (HCl) | 0.00003 |
| Aqueous, pH 6.2 (unaltered) | 0.00003 |
| Aqueous, pH 7.2 (NaOH) | 0.00001 |
| FaSSIF[1] pH = 6.5 | 0.025 |

TABLE 20-continued

Solubility of Ledipasvir amorphous free base as a function of pH at room temperature

| Aqueous Media | Solubility (mg/mL) |
|---|---|
| FeSSIF[2] pH = 5.0 | 0.230 |
| SIBLM[3] pH = 6.4 | 0.232 |

[1]FaSSIF is water with 3 mM sodium taurocholate and 0.75 mM lecithin, pH adjusted to 6.5 with phosphate buffer, ionic strength adjusted to 0.15M with NaCl.
[2]FeSSIF is water with 15 mM sodium taurocholate and 3.75 mM lecithin, pH adjusted to 6.5 with phosphate buffer, ionic strength adjusted to 0.15M with NaCl.
[3]SIBLM is water with 30 mM sodium glycocholate, 30 mM sodium glycochenodesoxycholate, 15 mM sodium glycodesoxycholate, 10 mM sodium taurocholate, 10 mM sodium taurochenodesoxycholate, 5 mM sodium taurodesoxycholate, 50 mM sodium chloride, and 11 mM lecithin, pH adjusted to 6.4 with phosphate buffer, ionic strength adjusted to 0.15M with NaCl.

The dissolution rate of ledipasvir amorphous free base at pH 3 and 6 was also tested. At pH 3, the dissolution of the amorphous free base form is faster than that of the crystalline free base and acetone solvate forms. However, at pH 6, all free base forms show similar dissolution rate profiles.

As shown in Table 21, ledipasvir amorphous free base is freely soluble (>500 mg/mL) in ethanol and other organic solvents such as propylene glycol and PEG 400. Its solubility is greater than 200 mg/mL in surfactants (e.g., polysorbate 80, Cremophor EL, Labrasol) and lipid blends. Its solubility in oleic and octanoic acids is greater than 500 mg/mL. Solubility of ledipasvir in short-chain triglycerides (SCTs, tributyrin) is limited to 20 mg/mL, and decreases to less than 1 mg/mL in long-chain triglycerides (LCTs, soybean oil). It has a solubility of 25 mg/mL in the vehicle chosen for toxicological studies: 45% propylene glycol, 15% caprylocaproyl macrogol-8 glycerides (Solutol HS)15®, and 40% water (pH 2.5 by HCl).

TABLE 21

Solubility of Ledipasvir free base forms and Ledipasvir D-tartrate in organic solvents and excipients at room temperature

| | Solubility (mg/mL) | | | |
|---|---|---|---|---|
| | Amorphous Free Base (Ledipasvir) | Crystalline Acetone Solvate (Ledipasvir-03) | Anhydrous Crystalline Free Base (Ledipasvir Form III) | Crystalline D-tartrate Salt (Ledipasvir-02) |
| Acetone | 5 | 5 | — | <1 |
| Acetonitrile | >500 | — | — | 12 |
| Methanol | >500 | >500 | — | 23 |
| 95% Methanol + 5% water | — | — | — | 19 |
| Ethanol | >500 | >500 | >500 | 4 |
| 95% Ethanol + 5% water | — | — | — | 5 |
| PEG 400 | >500 | >500 | >500 | 4 |
| Propylene glycol | >500 | >500 | >500 | 6 |
| Octanoic acid | >500 | >500 | — | <1 |
| Oleic acid | >500 | >500 | >500 | <1 |
| Polyoxyl 35 Castor Oil (Cremophor EL) | >200 | — | — | — |
| Polysorbate 80 (Tween 80) | >200 | >200 | >200 | 3 |
| Caprylocaproyl macrogolglycerides (Labrasol) | >300 | >300 | >300 | 3 |

TABLE 21-continued

Solubility of Ledipasvir free base forms and Ledipasvir D-tartrate in organic solvents and excipients at room temperature

| | Solubility (mg/mL) | | | |
|---|---|---|---|---|
| | Amorphous Free Base (Ledipasvir) | Crystalline Acetone Solvate (Ledipasvir-03) | Anhydrous Crystalline Free Base (Ledipasvir Form III) | Crystalline D-tartrate Salt (Ledipasvir-02) |
| Tributyrin | 9 | — | — | — |
| Soybean oil | 2 | 2 | 2 | — |
| RSSEDDS[1] | >500 | — | — | 10 |

[1]RSSEDDS: 10% Ethanol, 10% PG, 40% Solutol HS-15, 40% Labrasol

Dilute nonionic surfactants generally increase ledipasvir solubility at both pH 2 and 5, as presented in Table 22. Similar effects were observed with nonionic polymers, though to a lesser extent. Sodium lauryl sulfate (SLS), an anionic surfactant, improves the solubility of ledipasvir at pH 5. However, a significant decrease in solubility is noted in presence of SLS under acidic conditions (pH 2). This observation is consistent with weakly basic compounds that have low intrinsic aqueous solubility, presumably forming an insoluble estolate salt.

TABLE 22

Solubility of Ledipasvir amorphous free base in surfactant or polymeric excipients (0.1% w/w) diluted into aqueous media at pH 2 and 5 at room temperature

| Excipient (0.1% w/w in aqueous media) | Solubility (mg/mL) | |
|---|---|---|
| | pH 2 | pH 5 |
| No excipient | 4.94 | 0.0001 |
| Sodium lauryl sulfate | 0.05 | 0.243 |
| Labrasol | 7.44 | — |
| Cremophor EL | 9.11 | 0.0699 |
| Polysorbate 80 | 9.27 | 0.0624 |
| Poloxamer 188 | 7.19 | 0.0005 |
| HPC (hydroxypropylcellulose) | 4.67 | 0.0001 |
| HPMC (hydroxymethylcellulose) | 5.27 | 0.0003 |
| PVP (povidone) | 5.47 | 0.0004 |
| PVP/VA (copovidone) | 6.73 | 0.0010 |

Ledipasvir Crystalline Acetone Solvate (Ledipasvir-03)

The ledipasvir acetone solvate (ledipasvir-03) showed similar steady-state solubility as the other forms. Ledipasvir-03 has the slowest dissolution of all forms tested. Its dissolution at pH 6 was indistinguishable from that of other forms due to poor intrinsic solubility (<0.1 μg/mL).

Ledipasvir-03 is soluble in many organic solvents and pharmaceutically acceptable solvents, and the solubilities are comparable to those listed for ledipasvir amorphous free base, as also shown in Table 21.

Ledipasvir Crystalline Free Base (Form III)

Ledipasvir crystalline free base Form III showed similar steady-state solubility as the other forms (FIG. 9). This form dissolves more slowly than the amorphous free base, but faster than ledipasvir-03. Dissolution at pH 6 was indistinguishable from that of the other forms due to poor intrinsic solubility (<0.1 μg/mL). Solubility in a wider range of organic vehicles has not been explored, though is anticipated to be similar to other free base forms.

Ledipasvir Crystalline D-Tartrate Salt (Ledipasvir-02)

Ledipasvir crystalline D-tartrate salt (ledipasvir-02) showed similar steady-state solubility as the other forms (FIG. 9). Dissolution behavior ledipasvir-02 is improved relative to all free base forms. At pH 3, ledipasvir-02 shows a roughly 5- to 10-fold faster initial dissolution rate than the free base forms, and roughly doubled the amount of ledipasvir in solution through 60 minutes compared to the amorphous form. At pH 6, the increased dissolution rate was also apparent. However, rapid dissociation of the salt at this pH resulted in equivalent solubility values to other forms within minutes.

Ledipasvir-02 is not soluble in various organic media, as shown in Table 21. Maximal solubility of ledipasvir-02 in any organic vehicle is 20 mg/mL in methanol; this limits the use of ledipasvir-02 in solubilized formulations or processes that require solubilization in organic media.

Ledipasvir has low aqueous solubility and high permeability, and is considered a BCS Class 2 compound. The data presented in this example indicate that in water, all forms of ledipasvir: the amorphous free base, crystalline free base acetone solvate (ledipasvir-03), crystalline anhydrous free base (Form III), and crystalline D-tartrate salt (ledipasvir-02), convert to the amorphous free base, and have similar aqueous solubility at steady state. The aqueous solubility of ledipasvir is less than 0.1 µg/mL in its neutral form (pH>5), but substantially increases under acidic conditions due to protonation of two basic moieties. The aqueous dissolution rate of ledipasvir amorphous free base is faster than that of crystalline free base forms. However, all free base forms have slower dissolution rates than the crystalline D-tartrate salt (ledipasvir-02). Ledipasvir-02 also shows improved wetting in aqueous media. ledipasvir free base forms, crystalline and amorphous, are highly soluble in a range of cosolvents and surfactants. In contrast, ledipasvir-02 is poorly soluble in organic excipients, and this property potentially limits its utility.

Ledipasvir amorphous free base was used in Phase 1 clinical studies, but drug substance manufacturing was identified as a critical limitation of the form. Ledipasvir crystalline D-tartrate salt (ledipasvir-02) was then identified as part of a more extensive salt and form screen and was used in Phase 2, however, poor solubility in organic excipients limits its utility in non-conventional formulations. Crystalline ledipasvir acetone solvate (ledipasvir-03) is used to develop a spray dried dispersion formulation to support future clinical studies due to its solubility in organic solvents and excipients relative to crystalline ledipasvir D-tartrate salt and improved manufacturability over the other free base forms.

Example 9

Efficacy of a Fixed Dose Combination of Sofosbuvir and Ledipasvir with and without Ribavirin in Patients with HCV Infections Patients with HCV infections were treated with the fixed dose combination of sofosbuvir and ledipasvir, with and without ribavirin. Patients used in the studies include those that were treatment naïve (non-cirrhotic), i.e. had not previously been treated for HCV, and those that were prior protease-inhibitor (PI) failures and null responders (with and without cirrhosis), i.e. had previously been treated for HCV but failed to respond to the treatment. The treatment naïve pateints were treated for 6, 8, and 12 weeks and the null responders were treated for 12 weeks.

Study 1

Figure 10:
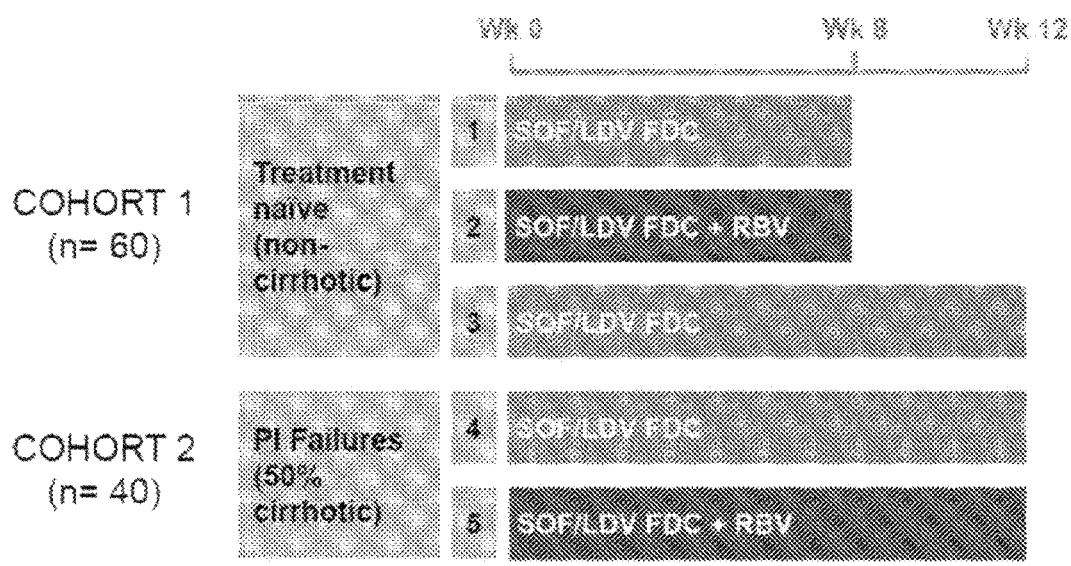
FIG. 10 shows the study design for treatment naïve (non-cirrhotic) and for null responders (50% cirrhotic) for patients treated with a fixed dose combination of sofosbuvir (SOF) and ledipasvir, with and without ribavirin (RBV) for 8 and 12 weeks. The data and experimental method are described in Example 9.

Cohort 1 of study 1 included treatment-naïve, Genotype-1 patients without cirrhosis. The patients were randomized 1:1:1 into three groups to receive 1) SOF/ledipasvir fixed dose combination for 8 weeks, 2) SOF/ledipasvir fixed dose combination with ribavirin for 8 weeks, or 3) SOF/ledipasvir fixed dose combination for 12 weeks (FIG. 10).

Cohort 2 of study 1 included Protease-Inhibitor treatment-experienced, Genotype-1 patients (Prior Protease-Inhibitor treatment failures, 50% of whom had compensated cirrhosis). The pateints were randomized to receive 12 weeks of: 1) SOF/ledipasvir fixed dose combination or 2) SOF/ledipasvir fixed dose combination with ribavirin (FIG. 10). In Cohort 2, the patients must not have discontinued prior therapy due to an adverse event.

In study 1, there was a broad inclusion criteria, namely, there was no upper limit to age or BMI. Platelets were $\geq 50,000/mm^3$. The demographics of study 1 are shown in Table 23, below.

TABLE 23

| Demographics | |
|---|---|
| | SOF/Ledipasvir fixed dose combination ± ribavirin |
| | (Cohort 1 and 2) N = 100 |
| Mean age, y (range) | 50 (21-73) |
| Male, n (%) | 66 (66) |
| Black, n (%) | 9 (9) |
| Hispanic, n (%) | 40 (40) |
| Mean BMI, kg/m² (range) | 29.9 (18-48) |
| IL28B CC, n (%) | 15 (15) |
| GT 1a, n (%) | 87 (87) |
| Mean baseline HCV RNA, log$_{10}$ IU/mL (range) | 6.1 (3.7-7.2) |
| | Cohort 2 (N = 40) |
| Cirrhosis, n (%) | 22/40 (55) |
| Mean Platelet Count (×10³/µL) | 107 |
| Mean Albumin (g/dL) | 3.8 |

Of 100 patients enrolled in study 1, 97% achieved sustained viral response. Of the failures, two patients relapsed (one from Group 1 (i.e., SOF/Ledipasvir×8 Weeks) and one from Group 4 (i.e., SOF/ledipasvir×12 Weeks), and one patient was lost to follow up from Group 3 (i.e., SOF/ledipasvir×12 Weeks). However, the patient lost to follow up had achieved SVR at week 8 and declined further return visits.

Figure 11:
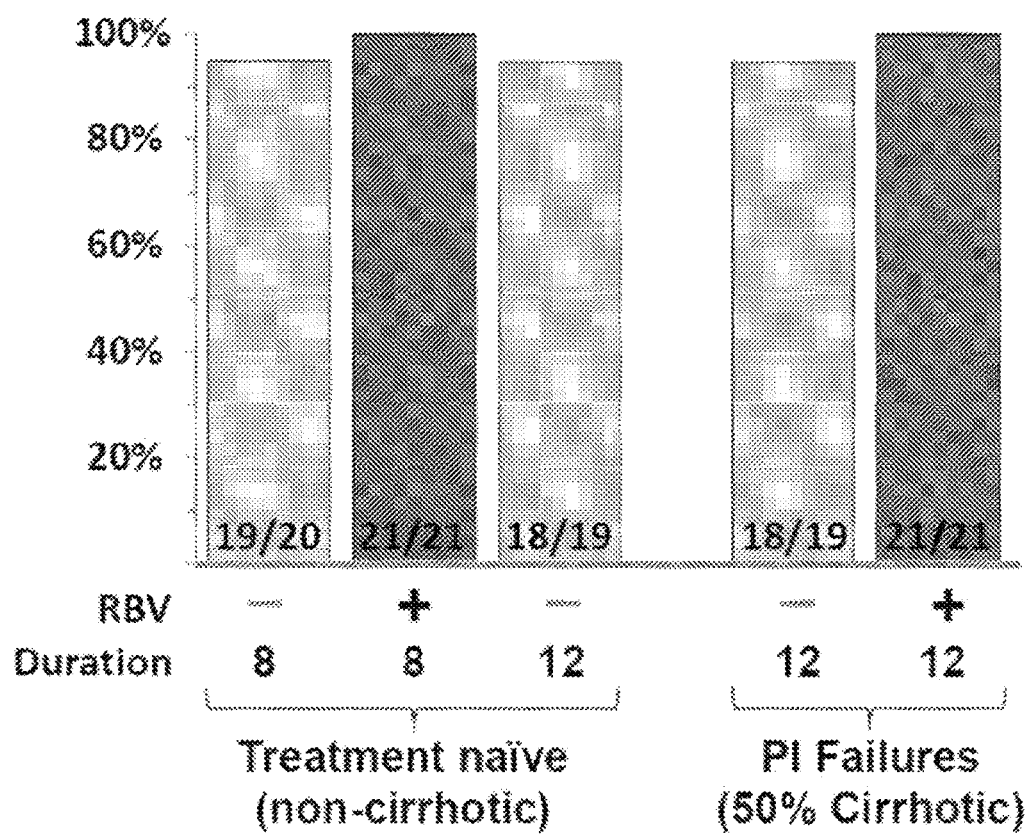
FIG. 11 shows the results for treatment naïve (non-cirrhotic) and for null responders (50% cirrhotic) for patients treated with a fixed dose combination of sofosbuvir (SOF) and ledipasvir, with and without ribavirin (RBV) for 8 and 12 weeks. This data and experimental method are further described in Example 9.

In Cohort 1 of study 1 (i.e. Treatment Naïve, Non-Cirrhotic Patients), 58 out of the 60 patients treated for 8 or 12 Weeks achieved SVR. In corhort 2 of study 1 (i.e. Treatment Experienced, PI failure Patients), 39 out of the 40 patients treated for 12 Weeks achieved SVR12. 21 out of the 21 patients with cirrhosis achieved SVR12 (FIG. 11).

In study 1, seven out of the nine patients with NS5A Resistance Associated Variants (RAVs) achieved sustained viral response. In addition, all patients with NS3/4A Resistance Associated Variants achieved sustained viral response. Interestingly, S282T mutation and multiple NS5A RAVs were detected at relapse in the patient who failed from the Group 1 (Table 24). The safety summary and a breakdown of the adverse effects are shown in Tables 25 and 26, respectively.

TABLE 24

Resistance analysis

| | SOF/Ledipasvir fixed dose combination ± ribavirin |
|---|---|
| NS5A RAVs, n % | 9/100 (9) |
| NS3/4A RAVs, n % | 29/40 (73)* |

*number of patients in Cohort 2 with prior exposure to a protease inhibitor

TABLE 25

Safety Summary

| | Patients, n (%) | SOF/Ledipasvir fixed dose combination N = 58 | SOF/Ledipasvir fixed dose combination + ribavirin N = 42 |
|---|---|---|---|
| Overall safety | AEs | 24 (41%) | 24 (57%) |
| | Grade 3-4 AEs | 0 | 6 (14%) |
| | Serious AEs | 2* (3%) | 2** (5%) |
| | Treatment discontinuation due to AEs | 0 | 0 |
| Laboratory abnormalities | Grade 3-4 laboratory abnormality | 4 (7%) | 6 (14%) |
| | Hemoglobin <10 g/dL | 0 | 8 (19%) |
| | Hemoglobin <8.5 g/dL | 0 | 2 (5%) |

*peptic ulcer, spinal compression fracture
**delerium, suicidal ideation

TABLE 26

Adverse Events (≥5% of patients overall)

| Preferred term, n (%) | SOF/Ledipasvir fixed dose combination N = 58 | SOF/Ledipasvir fixed dose combination + ribavirin N = 42 |
|---|---|---|
| Any adverse event | 24 (41%) | 24 (57%) |
| Nausea | 3 (5%) | 6 (14%) |
| Anemia | 0 | 8 (19%) |
| Upper Resp Tract Infx | 4 (7%) | 4 (10%) |
| Headache | 3 (5%) | 4 (10%) |

Study 2

In study 2, the treatment-naïve patients received SOF/ledipasvir fixed dose combination with ribavirin and prior null responders, all of whom had cirrhosis, were randomized to receive twelve weeks of: 1) SOF/ledipasvir fixed dose combination or 2) SOF/ledipasvir fixed dose combination with ribavirin.

Results

Of the 144 patients treated in both studies 1 and 2, 136 out of 144 (94%) achieved SVR at four weeks post treatment. Of the 85 treatment-naïve patients in these two studies, three of 25 patients failed to achieve SVR after 6 weeks of SOF/ledipasvir fixed dose combination with ribavirin therapy, whereas 100% (60/60) patients achieved SVR after 8 or 12 weeks of SOF/ledipasvir fixed dose combination with and without ribavirin therapy. Of the 59 treatment-experienced patients in these two studies, three cirrhotic patients relapsed after receiving 12 weeks of SOF/ledipasvir fixed dose combination without ribavirin. Conversely, no virologic failures were observed in the SOF/ledipasvir fixed dose combination with ribavirin treatment groups, but two patients in these groups were lost to follow-up. SOF/ledipasvir fixed dose combination with and without ribavirin was well tolerated, with few SAEs and minimal adverse events.

Conclusion

SOF/ledipasvir fixed dose combination +/−ribavirin may be given for as little as 8 weeks to treatment-naïve non-cirrhotic patients. Treatment-experienced patients, even those with cirrhosis, achieved high SVR rates with 12 weeks of the of SOF/ledipasvir fixed dose combination with and without ribavirin therapy.

Example 10

Efficacy of Multiple Anti-HCV Combination Therapy in Chronically Infected Hepatitis C Patients To evaluate the safety, tolerability, and efficacy of 4 to 12 weeks of SOF with ledipasvir, alone or in combination with Compound E and/or Compound J in patients with HCV, patients with HCV will be dosed as shown in Table 27.

TABLE 27

Dosing

| Group | Treatment | Dosing | Patient description |
|---|---|---|---|
| Group A | 12 weeks of SOF/ledipasvir | SOF with ledipasvir (400 mg/90 mg respectively once a day in a fixed dose combination) administered orally for 12 weeks | Patients (n = 20) monoinfected with HCV genotype 1 who are HCV treatment naïve |
| Group B | 6 weeks of SOF/ledipasvir/Compound E | SOF with ledipasvir (400 mg/90 mg respectively once a day in a fixed dose combination) in combination with Compound E (500 mg once daily) for 6 weeks | Patients (n = 20) monoinfected with HCV genotype 1 who are HCV treatment naïve |
| Group C | 6 weeks of SOF/ledipasvir/Compound J | SOF with ledipasvir (400 mg/90 mg respectively once a day in a fixed dose combination) in combination with Compound J (80 mg once daily) for 6 weeks. | Patients (n = 20) monoinfected with HCV genotype 1 who are HCV treatment naïve |

TABLE 27-continued

Dosing

| Group | Treatment | Dosing | Patient description |
|---|---|---|---|
| Group D | 12 weeks of SOF/ledipasvir | SOF with ledipasvir (400 mg/90 mg respectively once a day in a fixed dose combination) administered orally for 12 weeks | Patients (n = up to 25) monoinfected with HCV genotype 1 who were previously treated in Group B, C, F, G or H of this study or a similar study |
| Group E | 12 weeks of SOF/ledipasvir | SOF with ledipasvir (400 mg/90 mg respectively once a day in a fixed dose combination) administered orally for 12 weeks | Patients (n = 20) monoinfected with HCV genotype 4 who are HCV treatment naïve or treatment experienced |
| Group F | 6 weeks of SOF/ledipasvir/ Compound J | SOF with ledipasvir (400 mg/90 mg respectively once a day in a fixed dose combination) in combination with Compound J (80 mg once daily) for 6 weeks. | Patients (n = 50) monoinfected with HCV genotype 1 with advanced liver disease who are HCV treatment naïve (n = 25) or treatment experienced (n = 25) |
| Group G | 4 weeks of SOF/ledipasvir/ Compound J | SOF with ledipasvir (400 mg/90 mg respectively once a day in a fixed dose combination) in combination with Compound J (80 mg once daily) for 4 weeks | Patients (n = 25) monoinfected with HCV genotype 1 who are HCV treatment naïve, Stage 0-2 liver disease |
| Group H | 4 weeks of SOF/ledipasvir/ Compound J/Compound E | SOF with ledipasvir (400 mg/90 mg respectively once a day in a fixed dose combination) in combination with Compound J (80 mg once daily) and Compound E (250 mg once daily) for 4 weeks | Patients (n = 25) monoinfected with HCV genotype 1 who are HCV treatment naïve, Stage 0-2 liver disease |

The primary analysis set for safety analyses will include patients who received at least one dose of study drug. On treatment data will be analyzed and defined as data collected from the first dose of study drug through the date of last dose of study drug plus 30 days. Patients who receive study drug other than that to which they were assigned will be analyzed according to the study drug received.

The analysis set for antiviral activity analyses will include patients who were enrolled into the study and received at least one dose of study drug.

The pharmacokinetic analysis set will include all patients who are enrolled and have received at least one dose of study medication.

The patient will be started on study treatment after confirming eligibility on Day 0 and after being informed fully about the remainder of the study, and then signing the specific consent for the treatment group (if not done previously). Blood will be drawn for HCV viral loads, study drug levels, lipid levels for research if not already drawn during screening, immunologic studies, and for storage prior to dosing as part of the screening consent. A pregnancy test will be done for females with childbearing potential and the pregnancy test must be negative on Day 0 prior to dosing with study drugs. Patients may be asked to fill out a baseline adherence questionnaire and an electronic pill bottle cap, which records pill bottle openings will be placed on all study drug bottles. Assistance will be provided filling out the questionnaire as needed. Patients on Arms B and H, will also be provided with a diary at Day 0, Week 2, Week 4 (Arm B only) on which to record gastrointestinal side effects.

On arrival at the clinic for scheduled study visits, patients will have their vital signs obtained, females will undergo a pregnancy test (if appropriate per schedule and of childbearing potential), clinical laboratories drawn, and a review of the study restrictions.

At each scheduled study visit (does not include Day 1, 3, 5, 10, Week 2, Week 3, Week 6 (not applicable for arm F, G or H) or post-treatment week 2 and 8 which are for lab collection only), patients will be asked about their state of health and use of any concomitant medication since the previous study visit. They will also be questioned about adverse events and their adherence with study restrictions. Vital signs, weight and examination will be performed as per the study flow. A complete list of study procedures and lab tests to be performed is in the Schedule of Tests, below. In addition, patients may be seen at unscheduled visits for a grade 3 or 4 adverse event or any unexpected adverse event or potential toxicity.

Patients may be asked to fill out a follow-up adherence questionnaire and pill bottle openings may be recorded from the electronic bottle cap at Day 7 (Group A), Week 4 (Group A), Week 6 (Groups B and C), Week 8 (Group A), and Week 12 (Group A). Assistance will be provided filling out the questionnaire as needed.

Patients in Groups B and H will be asked to bring their side-effect diaries to visits on Week 2, 4, 6 (B only).

Some of the visits have a small amount of flexibility regarding when they need to occur. Visits occurring during the interval when the patient is receiving study drug have limited flexibility since they occur so frequently, so a visit skipped during this period may be considered a missed visit. The window period for visit schedules is as shown in Table 28.

QD) under fed conditions. Preliminary PK results for the combination of sofosbuvir with Compound E are presented in Table 29 and demonstrate lack of a clinically significant interaction between sofosbuvir and Compound E.

TABLE 28

Window Period for Visit Schedule

For 12 week regimen, Group A:

| Days 0, 1, 3 (no window) | Days 5, 7, 10, 14 (+/−2 days) | Weeks 3, 4, 6 (+/−3 days) | Weeks 8, 12 (+/−5 days) Optional Week 12 Research Liver Biopsy (+/−14 days) |
|---|---|---|---|

For 6 week regimens, Groups B & C:

| Days 0, 1, 3 (no window) | Days 5, 7, 10, 14 (+/−2 days) | Weeks 3, 4, 6 (+/−3 days) Optional Week 6 Research Liver Biopsy (+/−14 days) |
|---|---|---|

For 12 week regimens, Groups D and E:

| Day 0 (no window) | Week 4 (+/−3 days) | Weeks 8, 12 (+/−7 days) |
|---|---|---|

For 6 week regimen, Group F:

| Day 0 (no window) | Weeks 2, 4 (+/−3 days) | Week 6 (+/−5 days) Optional Week 6 Research Liver Biopsy (+/−14 days) |
|---|---|---|

For 4 week regimen, Group G or H:

| Day 0 (no window) | Day 7 (+/−2 days) Group H only | Weeks 2, 4 (+/−3 days) Optional Week 4 Research Liver Biopsy (+/−14 days) |
|---|---|---|

During the four week visit, HCV RNA may be obtained to determine if virologic-response based treatment stopping criteria have been met. Patients who fail to achieve >2log10 HCV RNA drop at this time (unless >2log drop would be below LLOQ) should be discontinued from therapy unless a review by the PI/LAI/Sponsor Medical Monitor determines otherwise (see 9.3.1).

At the end of treatment duration as determined by the study group, patients may discontinue dosing of SOF and ledipasvir, Compound E, and/or Compound J. In addition, if a patient's participation terminates prior to completion of pre-specified study drug duration, the End of Treatment assessments may be performed at any end-of-treatment visit. An optional research liver biopsy for research purposes may be performed at this time in up to 10 patients in each study group. The additional liver biopsy data will serve to explore hepatic HCV RNA sequence analysis. If patients are undergoing the optional research liver biopsy, they may have safety labs completed prior to the procedure and imaging as medically indicated. Patients who have a HCV VL<LLOQ may receive education about how to prevent re-infection with HCV.

All patients may be assessed for sustained virologic response at the 12 Weeks Post End of Treatment visit. Patients who have HCV VL<LLOD may be provided with education about how to prevent re-infection with HCV.

After discontinuation of the study drug, patients may be followed at 2, 4, 8, 12, 24, 36, and 48 weeks post-end of treatment. A serum pregnancy test may be done with each visit, as appropriate. Week 2 and 8 Post-End of Treatment may include only collection of labs.

Subjects (n=18) received single doses of sofosbuvir (400 mg) alone or in combination with Compound E (500 mg

TABLE 29

Pharmacokinetic Data for SOF, Compound E, and ledipasvir alone and upon co-administration SOF (n = 18)

| Mean (% CV) | SOF alone | | % GMR (90% CI) |
|---|---|---|---|
| | | SOF + Compound E | |
| $AUC_{inf}$ (ng · hr/ml) | 921 (61.2) | 1150 (40.2) SOF + Compound E + ledipasvir | 135 (116, 159) |
| $AUC_{last}$ (ng · hr/ml) | 908 (62.2) | 2560 (42.9) SOF + Compound E | 297 (253, 348) |
| | | 1140 (41.4) SOF + Compound E + ledipasvir | 135 (115, 159) |
| $C_{max}$ (ng/ml) | 515 (78.3) | 2550 (43.1) SOF + Compound E | 301 (255, 354) |
| | | 587 (51.1) SOF + Compound E + ledipasvir | 130 (97.1, 175) |
| | | 1260 (55.1) | 283 (219.366) |

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

We claim:

1. A fixed dose combination tablet comprising:
   a) from about 10% to about 25% w/w of a solid dispersion comprising ledipasvir dispersed within a polymer matrix formed by copovidone, wherein the weight ratio of ledipasvir to copovidone in the solid dispersion is about 1:1 and greater than 70% of the ledipasvir is amorphous;
   b) from about 35% to about 45% w/w of sofosbuvir wherein greater than 70% of the sofosbuvir is crystalline and the crystalline sofosbuvir has XRPD 2θ-reflections (° ±0.2θ) at about: 6.1, 12.7, 20.1 and 20.8;
   c) from about 5.0% to about 25% w/w of lactose monohydrate;
   d) from about 5.0% to about 25% w/w of microcrystalline cellulose;
   e) from about 1.0% to about 10% w/w of croscarmellose sodium;
   f) from about 0.5% to about 3% w/w of colloidal silicon dioxide; and
   g) from about 0.1% to about 3% w/w of magnesium stearate.

2. The fixed dose combination tablet of claim 1, which comprises
   a) about 40% w/w of sofosbuvir and
   b) about 18% w/w of the solid dispersion comprising ledipasvir.

3. The fixed dose combination tablet of claim 1, which comprises about 90 mg of ledipasvir and about 400 mg of sofosbuvir.

4. The fixed dose combination tablet of claim 3, which comprises:
   (c) about 165 mg of lactose monohydrate;
   (d) about 180 mg of microcrystalline cellulose;
   (e) about 50 mg of croscarmellose sodium;
   (f) about 10 mg of colloidal silicon dioxide; and
   (g) about 15 mg of magnesium stearate.

5. The fixed dose combination tablet of claim 3 comprising a film coating.

6. A method of treating a patient infected with hepatitis C virus comprising administering to the patient a therapeutically effective amount of a fixed dose combination tablet of claim 1.

7. The method of claim 6, wherein the fixed dose combination tablet is administered for about 24 weeks or less.

8. The method of claim 6, wherein the fixed dose combination tablet is administered for about 12 weeks or less.

9. The method of claim 6, wherein the fixed dose combination tablet is administered for about 8 weeks or less.

10. The method of claim 6, wherein the fixed dose combination tablet is administered for about 6 weeks or less.

11. The method of claim 6, wherein the fixed dose combination tablet is administered once daily for about 12 weeks or less and wherein the hepatitis C virus is genotype 1, 2, 3, 4, 5, or 6.

12. The method of claim 11, wherein the hepatitis C virus is genotype 1a or 1b.

13. The method of claim 6, wherein the fixed dose combination tablet is administered once daily for about 8 weeks or less and wherein the hepatitis C virus is genotype 1, 2, 3, 4, 5, or 6.

14. The method of claim 6, wherein the fixed dose combination tablet is administered once daily for about 6 weeks or less and wherein the hepatitis C virus is genotype 1, 2, 3, 4, 5, or 6.

15. A fixed dose combination tablet comprising:
   a) about 18% w/w of a solid dispersion comprising ledipasvir dispersed within a polymer matrix formed by copovidone, wherein the weight ratio of ledipasvir to copovidone in the solid dispersion is about 1:1 and wherein greater than 70% of the ledipasvir is amorphous;
   b) about 40% w/w of sofosbuvir, wherein greater than 70% of the sofosbuvir is crystalline, wherein the crystalline sofosbuvir has XRPD 2θ-reflections (° ±0.2θ) at about: 6.1, 12.7, 20.1 and 20.8;
   c) about 16.5% w/w of lactose monohydrate;
   d) about 18.0% w/w of microcrystalline cellulose;
   e) about 5.0% w/w of croscarmellose sodium;
   f) about 1.0% w/w of colloidal silicon dioxide; and
   g) about 1.5% w/w of magnesium stearate.

16. A fixed dose combination tablet comprising:
   a) about 180 mg of a solid dispersion comprising ledipasvir dispersed within a polymer matrix formed by copovidone, wherein the weight ratio of ledipasvir to copovidone in the solid dispersion is about 1:1 and wherein greater than 70% of the ledipasvir is amorphous;
   b) about 400 mg of sofosbuvir, greater than 70% of the wherein sofosbuvir is crystalline, wherein the crystalline sofosbuvir has XRPD 2θ-reflections (° ±0.2θ) at about: 6.1, 12.7, 20.1 and 20.8;
   c) about 165 mg of lactose monohydrate;
   d) about 180 mg of microcrystalline cellulose;
   e) about 50 mg of croscarmellose sodium;
   f) about 10 mg of colloidal silicon dioxide; and
   g) about 15 mg of magnesium stearate.

* * * * *

UNITED STATES PATENT AND TRADEMARK OFFICE
CERTIFICATE OF CORRECTION

PATENT NO. : 10,039,779 B2
APPLICATION NO. : 15/393847
DATED : August 7, 2018
INVENTOR(S) : Ben Chal et al.

Page 1 of 1

It is certified that error appears in the above-identified patent and that said Letters Patent is hereby corrected as shown below:

In the Claims

In Claim 16, Column 62, Lines 49-51 please replace the following:
"b) about 400 mg of sofosbuvir, greater than 70% of the
wherein sofosbuvir is crystalline, wherein the crystal-
line"

With:
-- b) about 400 mg of sofosbuvir, wherein greater than 70% of the
sofosbuvir is crystalline, wherein the crystal-
line --

Signed and Sealed this
Thirtieth Day of October, 2018

Andrei Iancu
*Director of the United States Patent and Trademark Office*